(12) United States Patent
Lund et al.

(10) Patent No.: US 7,659,077 B2
(45) Date of Patent: Feb. 9, 2010

(54) METHODS UTILIZING TARGET GENES RELATED TO IMMUNE-MEDIATED DISEASES

(76) Inventors: Riikka Lund, Mestarinkatu 5 as 22, FI-20810 Turku (FI); Zhi Chen, 4901 Battery La., Apt. 201, Bethesda, MD (US) 20814; Riitta Lahesmaa, Hevosenkenkä 14, FI-20880 Turku (FI)

( * ) Notice: Subject to any disclaimer, the term of this patent is extended or adjusted under 35 U.S.C. 154(b) by 0 days.

(21) Appl. No.: 10/549,204

(22) PCT Filed: Mar. 17, 2004

(86) PCT No.: PCT/FI2004/000155

§ 371 (c)(1), (2), (4) Date: Jun. 28, 2006

(87) PCT Pub. No.: WO2004/083366

PCT Pub. Date: Sep. 30, 2004

(65) Prior Publication Data

US 2006/0280684 A1 Dec. 14, 2006

Related U.S. Application Data

(60) Provisional application No. 60/455,529, filed on Mar. 17, 2003.

(51) Int. Cl.
*G01N 33/53* (2006.01)
*G01N 33/567* (2006.01)

(52) U.S. Cl. .................. 435/7.1; 435/7.24; 435/91.2

(58) Field of Classification Search .................. None
See application file for complete search history.

(56) References Cited

U.S. PATENT DOCUMENTS 6,414,117 B1 7/2002 Levinson

FOREIGN PATENT DOCUMENTS

| WO | WO-99/57130 A1 | 11/1999 |
| WO | WO-01/88199 A2 | 11/2001 |
| WO | WO 0188199 | * 11/2001 |
| WO | WO-02/28999 A2 | 4/2002 |

OTHER PUBLICATIONS

Salvi H. et al., British Journal of haematology, 2002, 118, 1065-1070.
Bellucci R. et al., Blood, vol. 98, nr. 11 part 1, Nov. 2001, p. 405a.
Hamalainen H et al., Genome Biol. 2001; 2(7).
Chen Z et al., Journal of interferon and cytokine research, vol. 22 supplement 1, 2002.

* cited by examiner

*Primary Examiner*—Prema Mertz
(74) *Attorney, Agent, or Firm*—Birch, Stewart, Kolasch & Birch, LLP

(57) ABSTRACT

The present invention provides methods utilizing novel target genes related to immune-mediated diseases, such as asthma, allergy and autoimmune diseases. The invention is based on a molecular level description of the polarization of CD4+ precursor cells (Thp) from which T helper cells are known to originate. Particularly, the present invention provides a method of identifying a compound capable of modulating the polarization of CD4+ lymphocytes. The invention is also related to a method for assessing the presence of, or a predisposition to, an immune-related disorder in a subject.

5 Claims, 8 Drawing Sheets

SEQUENCE LISTING

```
<160> NUMBER OF SEQ ID NOS: 45

<210> SEQ ID NO 1
<211> LENGTH: 26
<212> TYPE: DNA
<213> ORGANISM: Artificial Sequence
<220> FEATURE:
<223> OTHER INFORMATION: Murine oligo used for quantitative Real-Time
      RT-PCR

<400> SEQUENCE: 1
cagtgaagtg ttggtagaat gtgaca                                          26

<210> SEQ ID NO 2
<211> LENGTH: 23
<212> TYPE: DNA
<213> ORGANISM: Artificial Sequence
<220> FEATURE:
<223> OTHER INFORMATION: Murine oligo used for quantitative Real-Time
      RT-PCR

<400> SEQUENCE: 2
```

-continued

```
catcacaaag aactgagcag caa                                              23

<210> SEQ ID NO 3
<211> LENGTH: 24
<212> TYPE: DNA
<213> ORGANISM: Artificial Sequence
<220> FEATURE:
<223> OTHER INFORMATION: Murine oligo used for quantitative Real-Time
      RT-PCR

<400> SEQUENCE: 3
gaacaaagag acctggaaga tgga                                             24

<210> SEQ ID NO 4
<211> LENGTH: 20
<212> TYPE: DNA
<213> ORGANISM: Artificial Sequence
<220> FEATURE:
<223> OTHER INFORMATION: Murine oligo used for quantitative Real-Time
      RT-PCR

<400> SEQUENCE: 4
ggcggcgaga aagaaataaa                                                  20

<210> SEQ ID NO 5
<211> LENGTH: 18
<212> TYPE: DNA
<213> ORGANISM: Artificial Sequence
<220> FEATURE:
<223> OTHER INFORMATION: Murine oligo used for quantitative Real-Time
      RT-PCR

<400> SEQUENCE: 5
tcagctggcg gactggat                                                    18

<210> SEQ ID NO 6
<211> LENGTH: 22
<212> TYPE: DNA
<213> ORGANISM: Artificial Sequence
<220> FEATURE:
<223> OTHER INFORMATION: Murine oligo used for quantitative Real-Time
      RT-PCR

<400> SEQUENCE: 6
gctggaggac ttggacttga ag                                               22

<210> SEQ ID NO 7
<211> LENGTH: 24
<212> TYPE: DNA
<213> ORGANISM: Artificial Sequence
<220> FEATURE:
<223> OTHER INFORMATION: Murine oligo used for quantitative Real-Time
      RT-PCR

<400> SEQUENCE: 7
aaccttatag ccaccgtctt tgac                                             24

<210> SEQ ID NO 8
<211> LENGTH: 26
<212> TYPE: DNA
<213> ORGANISM: Artificial Sequence
<220> FEATURE:
<223> OTHER INFORMATION: Murine oligo used for quantitative Real-Time
      RT-PCR

<400> SEQUENCE: 8
gaagaataat gaatagctgg cttgtg                                           26
```

<210> SEQ ID NO 9
<211> LENGTH: 22
<212> TYPE: DNA
<213> ORGANISM: Artificial Sequence
<220> FEATURE:
<223> OTHER INFORMATION: Murine oligo used for quantitative Real-Time RT-PCR

<400> SEQUENCE: 9
gcaggcactc tgtcttctcc tt                                          22

<210> SEQ ID NO 10
<211> LENGTH: 26
<212> TYPE: DNA
<213> ORGANISM: Artificial Sequence
<220> FEATURE:
<223> OTHER INFORMATION: Murine oligo used for quantitative Real-Time RT-PCR

<400> SEQUENCE: 10
tgctcacaca cttttatcag tttgtc                                      26

<210> SEQ ID NO 11
<211> LENGTH: 25
<212> TYPE: DNA
<213> ORGANISM: Artificial Sequence
<220> FEATURE:
<223> OTHER INFORMATION: Murine oligo used for quantitative Real-Time RT-PCR

<400> SEQUENCE: 11
ccagcgatca gtgccagtca ccatt                                       25

<210> SEQ ID NO 12
<211> LENGTH: 31
<212> TYPE: DNA
<213> ORGANISM: Artificial Sequence
<220> FEATURE:
<223> OTHER INFORMATION: Murine oligo used for quantitative Real-Time RT-PCR

<400> SEQUENCE: 12
tccaccacac ctgttttgaa gctactctga g                                31

<210> SEQ ID NO 13
<211> LENGTH: 30
<212> TYPE: DNA
<213> ORGANISM: Artificial Sequence
<220> FEATURE:
<223> OTHER INFORMATION: Murine oligo used for quantitative Real-Time RT-PCR

<400> SEQUENCE: 13
tcctggatcc ttagctactg cctcctgtct                                  30

<210> SEQ ID NO 14
<211> LENGTH: 26
<212> TYPE: DNA
<213> ORGANISM: Artificial Sequence
<220> FEATURE:
<223> OTHER INFORMATION: Murine oligo used for quantitative Real-Time RT-PCR

<400> SEQUENCE: 14
tcttgtttcg acacttggca gcagca                                      26

```
<210> SEQ ID NO 15
<211> LENGTH: 28
<212> TYPE: DNA
<213> ORGANISM: Artificial Sequence
<220> FEATURE:
<223> OTHER INFORMATION: Murine oligo used for quantitative Real-Time
      RT-PCR

<400> SEQUENCE: 15
aggacaagtt ccccaaagat gctggact                                          28

<210> SEQ ID NO 16
<211> LENGTH: 26
<212> TYPE: DNA
<213> ORGANISM: Artificial Sequence
<220> FEATURE:
<223> OTHER INFORMATION: Human oligo used for quantitative Real-Time
      RT-PCR

<400> SEQUENCE: 16
ctctacgacg agagcagcag cgactg                                            26

<210> SEQ ID NO 17
<211> LENGTH: 19
<212> TYPE: DNA
<213> ORGANISM: Artificial Sequence
<220> FEATURE:
<223> OTHER INFORMATION: Human oligo used for quantitative Real-Time
      RT-PCR

<400> SEQUENCE: 17
gctgtggcac cgacacagt                                                    19

<210> SEQ ID NO 18
<211> LENGTH: 18
<212> TYPE: DNA
<213> ORGANISM: Artificial Sequence
<220> FEATURE:
<223> OTHER INFORMATION: Human oligo used for quantitative Real-Time
      RT-PCR

<400> SEQUENCE: 18
actcgccgcc cgtattct                                                     18

<210> SEQ ID NO 19
<211> LENGTH: 26
<212> TYPE: DNA
<213> ORGANISM: Artificial Sequence
<220> FEATURE:
<223> OTHER INFORMATION: Human oligo used for quantitative Real-Time
      RT-PCR

<400> SEQUENCE: 19
ctctacgacg agagcagcag cgactg                                            26

<210> SEQ ID NO 20
<211> LENGTH: 19
<212> TYPE: DNA
<213> ORGANISM: Artificial Sequence
<220> FEATURE:
<223> OTHER INFORMATION: Human oligo used for quantitative Real-Time
      RT-PCR

<400> SEQUENCE: 20
gctgtggcac cgacacagt                                                    19
```

<210> SEQ ID NO 21
<211> LENGTH: 24
<212> TYPE: DNA
<213> ORGANISM: Artificial Sequence
<220> FEATURE:
<223> OTHER INFORMATION: Human oligo used for quantitative Real-Time
      RT-PCR

<400> SEQUENCE: 21
gaactcggct tggaacttac tgaa                                          24

<210> SEQ ID NO 22
<211> LENGTH: 29
<212> TYPE: DNA
<213> ORGANISM: Artificial Sequence
<220> FEATURE:
<223> OTHER INFORMATION: Human oligo used for quantitative Real-Time
      RT-PCR

<400> SEQUENCE: 22
tcctcagtag aacacacgca ggagagctc                                     29

<210> SEQ ID NO 23
<211> LENGTH: 20
<212> TYPE: DNA
<213> ORGANISM: Artificial Sequence
<220> FEATURE:
<223> OTHER INFORMATION: Human oligo used for quantitative Real-Time
      RT-PCR

<400> SEQUENCE: 23
agctcgctgt ccgatgtttc                                               20

<210> SEQ ID NO 24
<211> LENGTH: 20
<212> TYPE: DNA
<213> ORGANISM: Artificial Sequence
<220> FEATURE:
<223> OTHER INFORMATION: Human oligo used for quantitative Real-Time
      RT-PCR

<400> SEQUENCE: 24
cttctgcagc ttccctgcac                                               20

<210> SEQ ID NO 25
<211> LENGTH: 19
<212> TYPE: DNA
<213> ORGANISM: Artificial Sequence
<220> FEATURE:
<223> OTHER INFORMATION: Human oligo used for quantitative Real-Time
      RT-PCR

<400> SEQUENCE: 25
agcgccggct atgcccctg                                                19

<210> SEQ ID NO 26
<211> LENGTH: 20
<212> TYPE: DNA
<213> ORGANISM: Artificial Sequence
<220> FEATURE:
<223> OTHER INFORMATION: Human oligo used for quantitative Real-Time
      RT-PCR

<400> SEQUENCE: 26
ctgaaccatc caggccaaat                                               20

<210> SEQ ID NO 27

```
<211> LENGTH: 18
<212> TYPE: DNA
<213> ORGANISM: Artificial Sequence
<220> FEATURE:
<223> OTHER INFORMATION: Human oligo used for quantitative Real-Time
      RT-PCR

<400> SEQUENCE: 27
gccgtgtggc aatccaat                                                  18

<210> SEQ ID NO 28
<211> LENGTH: 20
<212> TYPE: DNA
<213> ORGANISM: Artificial Sequence
<220> FEATURE:
<223> OTHER INFORMATION: Human oligo used for quantitative Real-Time
      RT-PCR

<400> SEQUENCE: 28
gccgaaccac ctccaccggt                                                20

<210> SEQ ID NO 29
<211> LENGTH: 19
<212> TYPE: DNA
<213> ORGANISM: Artificial Sequence
<220> FEATURE:
<223> OTHER INFORMATION: Human oligo used for quantitative Real-Time
      RT-PCR

<400> SEQUENCE: 29
gatgacgctt ctttcggcc                                                 19

<210> SEQ ID NO 30
<211> LENGTH: 17
<212> TYPE: DNA
<213> ORGANISM: Artificial Sequence
<220> FEATURE:
<223> OTHER INFORMATION: Human oligo used for quantitative Real-Time
      RT-PCR

<400> SEQUENCE: 30
cacggacgcc tggaaga                                                   17

<210> SEQ ID NO 31
<211> LENGTH: 22
<212> TYPE: DNA
<213> ORGANISM: Artificial Sequence
<220> FEATURE:
<223> OTHER INFORMATION: Human oligo used for quantitative Real-Time
      RT-PCR

<400> SEQUENCE: 31
tgccggagga ggtggatgtg ct                                             22

<210> SEQ ID NO 32
<211> LENGTH: 16
<212> TYPE: DNA
<213> ORGANISM: Artificial Sequence
<220> FEATURE:
<223> OTHER INFORMATION: Human oligo used for quantitative Real-Time
      RT-PCR

<400> SEQUENCE: 32
ggacgcggcg cagtac                                                    16

<210> SEQ ID NO 33
<211> LENGTH: 20
```

```
<212> TYPE: DNA
<213> ORGANISM: Artificial Sequence
<220> FEATURE:
<223> OTHER INFORMATION: Human oligo used for quantitative Real-Time
      RT-PCR

<400> SEQUENCE: 33
tgccttgacc gtcgatgtta                                                      20

<210> SEQ ID NO 34
<211> LENGTH: 24
<212> TYPE: DNA
<213> ORGANISM: Artificial Sequence
<220> FEATURE:
<223> OTHER INFORMATION: Human oligo used for quantitative Real-Time
      RT-PCR

<400> SEQUENCE: 34
tgctggcgac agttcagcca tcac                                                 24

<210> SEQ ID NO 35
<211> LENGTH: 23
<212> TYPE: DNA
<213> ORGANISM: Artificial Sequence
<220> FEATURE:
<223> OTHER INFORMATION: Human oligo used for quantitative Real-Time
      RT-PCR

<400> SEQUENCE: 35
ctcgaaacag catctgactc ctt                                                  23

<210> SEQ ID NO 36
<211> LENGTH: 21
<212> TYPE: DNA
<213> ORGANISM: Artificial Sequence
<220> FEATURE:
<223> OTHER INFORMATION: Human oligo used for quantitative Real-Time
      RT-PCR

<400> SEQUENCE: 36
tgtccaacgc aaagcaatac a                                                    21

<210> SEQ ID NO 37
<211> LENGTH: 23
<212> TYPE: DNA
<213> ORGANISM: Artificial Sequence
<220> FEATURE:
<223> OTHER INFORMATION: Human oligo used for quantitative Real-Time
      RT-PCR

<400> SEQUENCE: 37
aacgagcagg aatctcccag gcg                                                  23

<210> SEQ ID NO 38
<211> LENGTH: 19
<212> TYPE: DNA
<213> ORGANISM: Artificial Sequence
<220> FEATURE:
<223> OTHER INFORMATION: Human oligo used for quantitative Real-Time
      RT-PCR

<400> SEQUENCE: 38
accagtgggt acgcgatga                                                       19

<210> SEQ ID NO 39
<211> LENGTH: 21
<212> TYPE: DNA
```

```
<213> ORGANISM: Artificial Sequence
<220> FEATURE:
<223> OTHER INFORMATION: Human oligo used for quantitative Real-Time
      RT-PCR

<400> SEQUENCE: 39
tgttaaaagc cacacgtgca a                                              21

<210> SEQ ID NO 40
<211> LENGTH: 25
<212> TYPE: DNA
<213> ORGANISM: Artificial Sequence
<220> FEATURE:
<223> OTHER INFORMATION: Human oligo used for quantitative Real-Time
      RT-PCR

<400> SEQUENCE: 40
tcagcatgaa gcctgcattc ttgcc                                          25

<210> SEQ ID NO 41
<211> LENGTH: 23
<212> TYPE: DNA
<213> ORGANISM: Artificial Sequence
<220> FEATURE:
<223> OTHER INFORMATION: Human oligo used for quantitative Real-Time
      RT-PCR

<400> SEQUENCE: 41
acagctatga ggctgagttt cga                                            23

<210> SEQ ID NO 42
<211> LENGTH: 22
<212> TYPE: DNA
<213> ORGANISM: Artificial Sequence
<220> FEATURE:
<223> OTHER INFORMATION: Human oligo used for quantitative Real-Time
      RT-PCR

<400> SEQUENCE: 42
ggcctcggta gtaggacatg gt                                             22

<210> SEQ ID NO 43
<211> LENGTH: 20
<212> TYPE: DNA
<213> ORGANISM: Artificial Sequence
<220> FEATURE:
<223> OTHER INFORMATION: Human oligo used for quantitative Real-Time
      RT-PCR

<400> SEQUENCE: 43
ttcgcacgcc gattaccggc                                                20

<210> SEQ ID NO 44
<211> LENGTH: 19
<212> TYPE: DNA
<213> ORGANISM: Artificial Sequence
<220> FEATURE:
<223> OTHER INFORMATION: Human oligo used for quantitative Real-Time
      RT-PCR

<400> SEQUENCE: 44
acacgcactt ccgcacatt                                                 19

<210> SEQ ID NO 45
<211> LENGTH: 15
<212> TYPE: DNA
<213> ORGANISM: Artificial Sequence
```

```
<220> FEATURE:
<223> OTHER INFORMATION: Human oligo used for quantitative Real-Time
      RT-PCR

<400> SEQUENCE: 45
ctggcgcgcg tgatg                                                    15
```

US 7,659,077 B2

METHODS UTILIZING TARGET GENES RELATED TO IMMUNE-MEDIATED DISEASES

Figure 1:
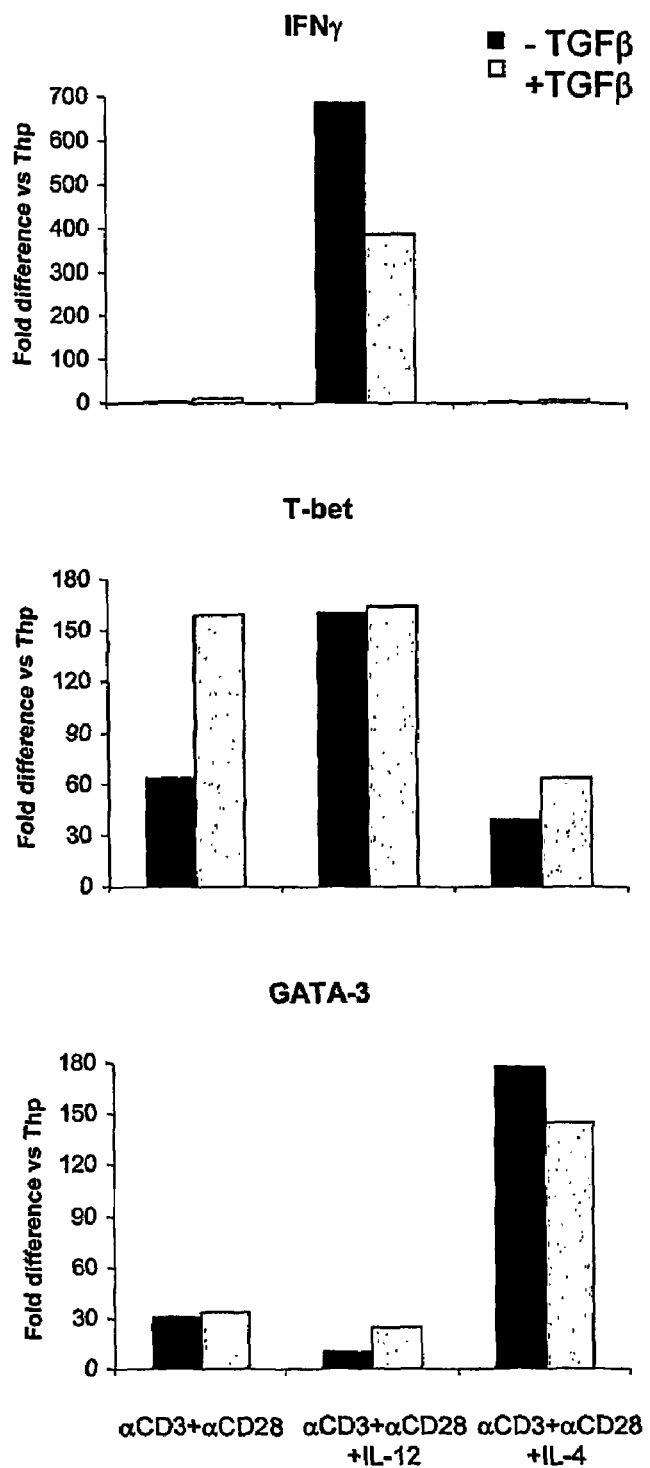

This application is the National Phase of PCT International application No. PCT/FI/2004/000155 filed on Mar. 17, 2004 which claims priority under 35 U.S.C. 119(e) on U.S. Provisional Application No. 60/455,529 filed on Mar. 17, 2003, which are hereby incorporated by reference.

FIELD OF THE INVENTION

The present invention provides methods utilizing novel target genes related to immune-mediated diseases, such as asthma, allergy and autoimmune diseases. The invention is based on a molecular level description of the polarization of CD4+ precursor cells (Thp) from which T helper cells are known to originate. T helper cell subtypes (Th1 and Th2) have an important role in the immune system. However, many pathological processes, such as allergies, are associated with the presence of T helper cells at the site of inflammation.

BACKGROUND

T helper cell subtypes Th1 and Th2 cells arise from a common precursor cell in response to triggering through the T cell receptor and cytokine receptors for IL-12 or IL-4. This leads to activation of complex signaling pathways. Disturbances in the balance between type 1 and type 2 responses can lead to certain immune-mediated diseases such as asthma, allergy and certain autoimmune diseases (1-3). Thus, it is important to understand how Th1 and Th2 cells are generated.

Th1 and Th2 cells are known to originate from naïve CD4+ precursor cells (Thp) after antigenic activation through the T cell receptor (TCR) and co-stimulatory molecules in a suitable cytokine milieu. The main cytokines orchestrating Th1 and Th2 development are IL-12 and IL-4, respectively. Triggering of the TCR and cytokine signaling leads to activation of complex, and to a large extent poorly understood, downstream signaling networks that finally result in maturation of the effector Th1 and Th2 cells (4, 5). IL-12 (and in human also IFNα) induces the Th1 type response by activating the Signal Transducer and Activator of Transcription 4 (STAT4) mediated signaling pathway (6-8). Some other cytokines such as IFNγ and IL-18 can also promote Th1 responses, especially in combination with IL-12. Th2 differentiation is induced by IL-4 through the STAT6 signaling pathway (9-12). GATA binding protein 3 (GATA-3), avian musculoaponeurotic fibrosarcoma (v-maf) AS42, oncogene homolog (c-maf) and T-box expressed in T cells (T-bet) are also among the most important factors regulating the early polarization of Th2 and Th1 cells respectively (11-16).

Another important cytokine involved in Th1 and Th2 differentiation is TGFβ. This immunosuppressive cytokine exhibits pleiotrophic activities in various cellular processes and, importantly, can suppress the differentiation of CD4+ cells into the Th1 and Th2 subtypes (17). However, similar to IL-12 and IL-4, the target genes and details of TGFβ downstream signaling are not clear.

To provide a basis for understanding the mechanism of action and molecular networks involved in the signaling of these cytokines, the early phase leading to polarization of Th1 and Th2 cells in the presence and absence of TGFβ was examined. As a result, genes differentially regulated in the cells induced to polarize to Th1 and Th2 subtypes in human were identified. Importantly, to our knowledge 77 of these genes have not been previously described to be involved in Th1 and Th2 cell differentiation. In addition, we have further clarified which of the genes involved in the early polarization of human Th1 and Th2 cells are targets of IL-12 and IL-4 regulation and which of them are also targets of immunosuppressive TGFβ. Wild type mouse cells or STAT6-knockout cells were used to further clarify the mechanism how IL-4 regulates gene expression through STAT6 signaling. These genes newly identified genes involved in Th1 and Th2 differentiation serve as therapeutic targets in achieving an appropriate balance between Th1 and Th2 responses.

SUMMARY

Certain methods of the invention are related to a method of identifying a compound capable of modulating the polarization of CD4+ lymphocytes. The method includes the steps of contacting the compound with naïve CD4+ lymphocytes, and then inducing the polarization of the cells. Further, a gene expression profile from the lymphocytes is prepared during the polarization, and the profile is compared to a baseline gene expression profile of CD4+ lymphocyte polarization as established in Table 1. A difference in the expression profiles of the target genes identifies a potential drug compound for the treatment of asthma or other immune-mediated diseases.

The invention is also related to a methods of identifying a compound that modulates the expression or activity of at least one target gene listed in Table 2 or Table 6. The methods include the steps of (a) incubating a cell that can express a protein from said gene or a cell that has said activity with a compound under conditions and for a time sufficient for the cell to express the protein or activity of said gene, when the compound is not present, (b) incubating a control cell under the same conditions and for the same time without the compound, (c) measuring expression or activity of said gene in the cell in the presence of the compound; (d) measuring expression or activity of said gene in the control cell; and (e) comparing the amount of expression or activity of said gene in the presence and absence of the compound, wherein a difference in the level of expression or activity indicates that the compound modulates the expression of said gene.

Other methods that are provided are to identify a compound that modulates differentiation of a lymphocyte. These methods generally involve contacting a test cell capable of expressing one or more gene markers listed in Table 2 or Table 6 with a test compound. The expression level of the one or more gene markers in the test cell is determined. The expression level of these gene markers are than compared with the expression levels for these same markers in a control cell. In these methods, the test cell and the control cell are lymphocytes and the cellular state of the control cell is known. A difference in the expression level between the test and control cell is an indicator that the test compound is a modulator of lymphocyte differentiation.

Another embodiment of the invention relates to a method of treating a patient with asthma or other immune-mediated disease. The method of treatment comprises administering to the patient a pharmaceutical composition that alters the expression or activity of at least one gene listed in Table 2 or Table 6. In a preferred embodiment of the invention, the active compound of said pharmaceutical composition is identified by a method of the invention.

Methods for classifying a lymphocyte or assessing the cellular state of a lymphocytic cell are also provided. Certain of these methods involve providing a test sample derived from the lymphocyte, wherein the lymphocyte is capable of expressing one or more nucleic acid markers from the group consisting of those listed in one or more of the tables (e.g. Table 1 or Table 2 and/or Table 6). The expression level of the one or more markers in the test sample are determined and compared with the expression level of the same markers in a control sample. The control sample is derived from a lymphocytic cell whose cellular status is known. The lymphocyte is then classified on the basis of this comparison. In some instances, the methods involve classifying the lymphocyte as being a Th1 or Th2 type cell.

A variety of methods for diagnosing the presence of, or a predisposition to, an immune-related disease are provided as well. These methods generally involve determining the expression level of one or more nucleic acid markers in a test sample obtained from a subject. These markers are selected from the group consisting of those listed in one or more of the tables (e.g. Table 1 or Table 2 and/or Table 6). The expression level of the one or more nucleic acid markers in the test sample is compared with the expression level of the same markers in a control sample whose immune status is known. The presence or absence of the immune disorder in the subject, or a predisposition to the immune disorder, is then diagnosed on the basis of this comparison.

A BRIEF DESCRIPTION OF THE DRAWINGS

FIG. 1. Expression of Th1 and Th2 marker genes. CD4+ cells were purified from human cord blood and were activated with plate-bound αCD3 (1000 ng/µl for goating) and 500 ng/µl soluble αCD28. The cells were further polarized with either 2.5 ng/ml of IL-12 for Th1 conditions or 10 ng/ml of IL-4 for Th2 conditions in the presence and absence of 3 ng/ml TGFβ. Part of the activated cells were cultured in "neutral conditions" without any polarizing cytokines. The cells were collected at the time points of 0 h and 48 h. RNA was isolated from the samples and cDNA was prepared. Expression of known marker genes IFNγ, T-bet and GATA-3 was measured from the samples using Real-Time RT-PCR to ensure the polarization of the cells to the Th1 and Th2 direction. The figure shows representative data from one of two repeated experiments.

Figure 2A:
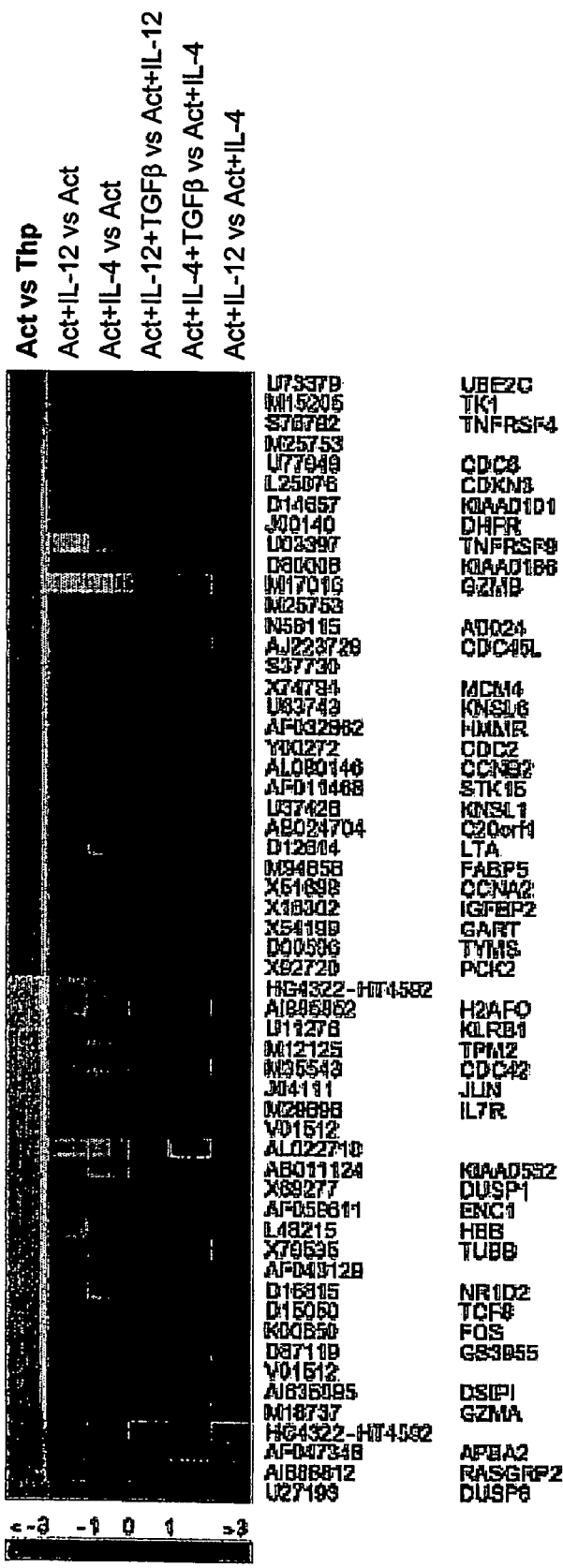
Figure 2B:
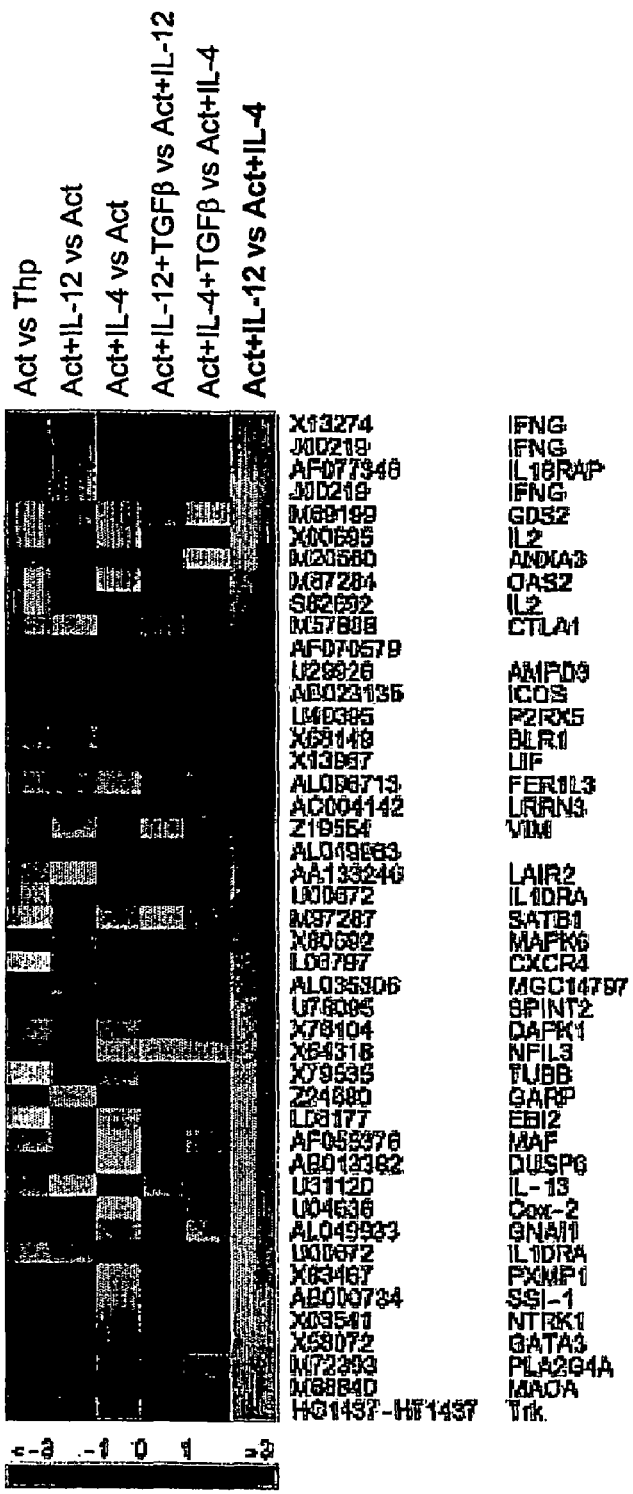
Figure 2C:
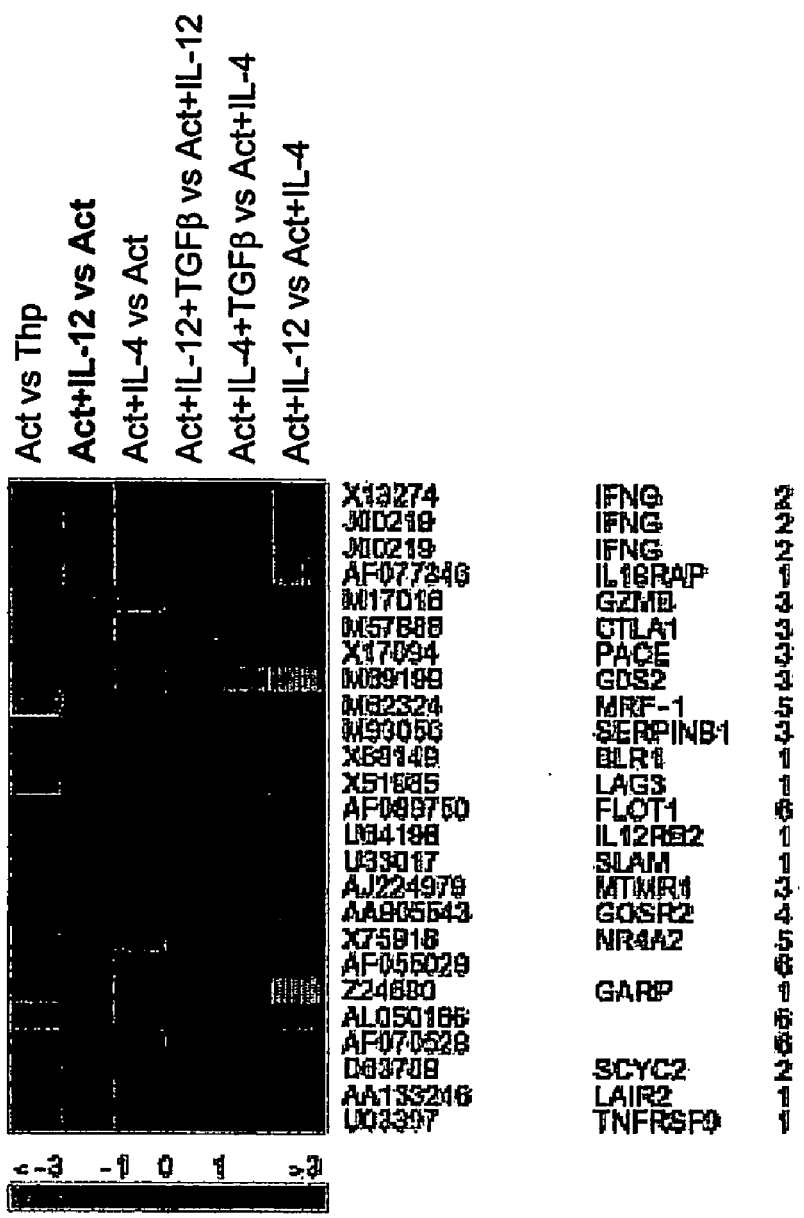
Figure 2D:
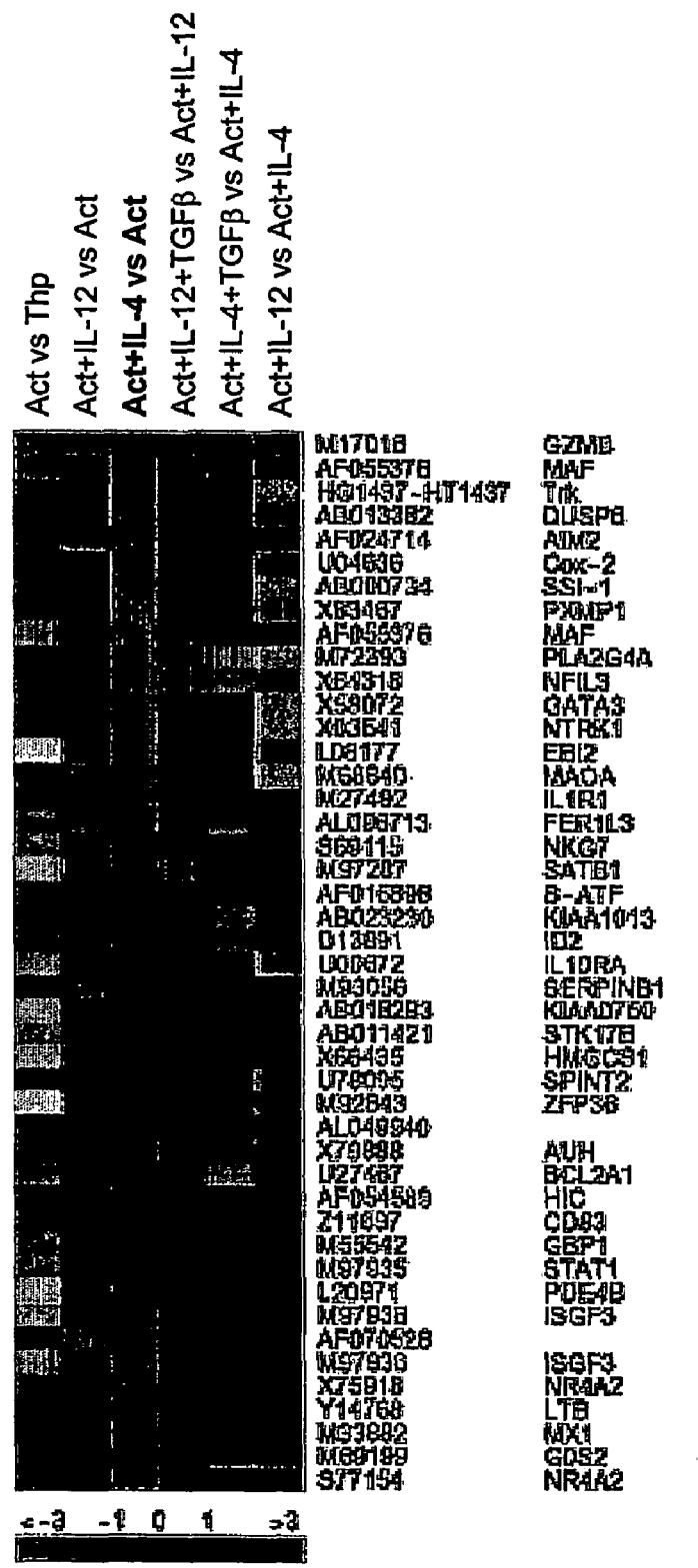
Figure 2E:
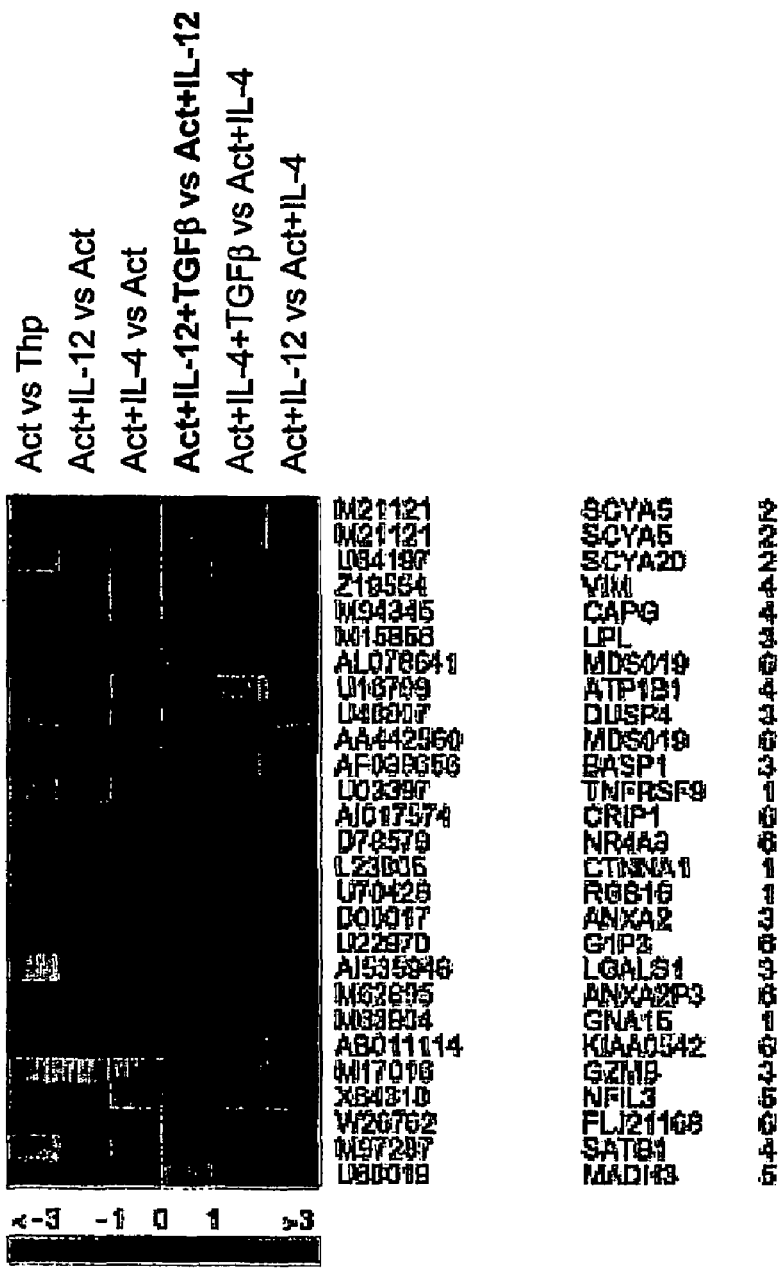
Figure 2F:
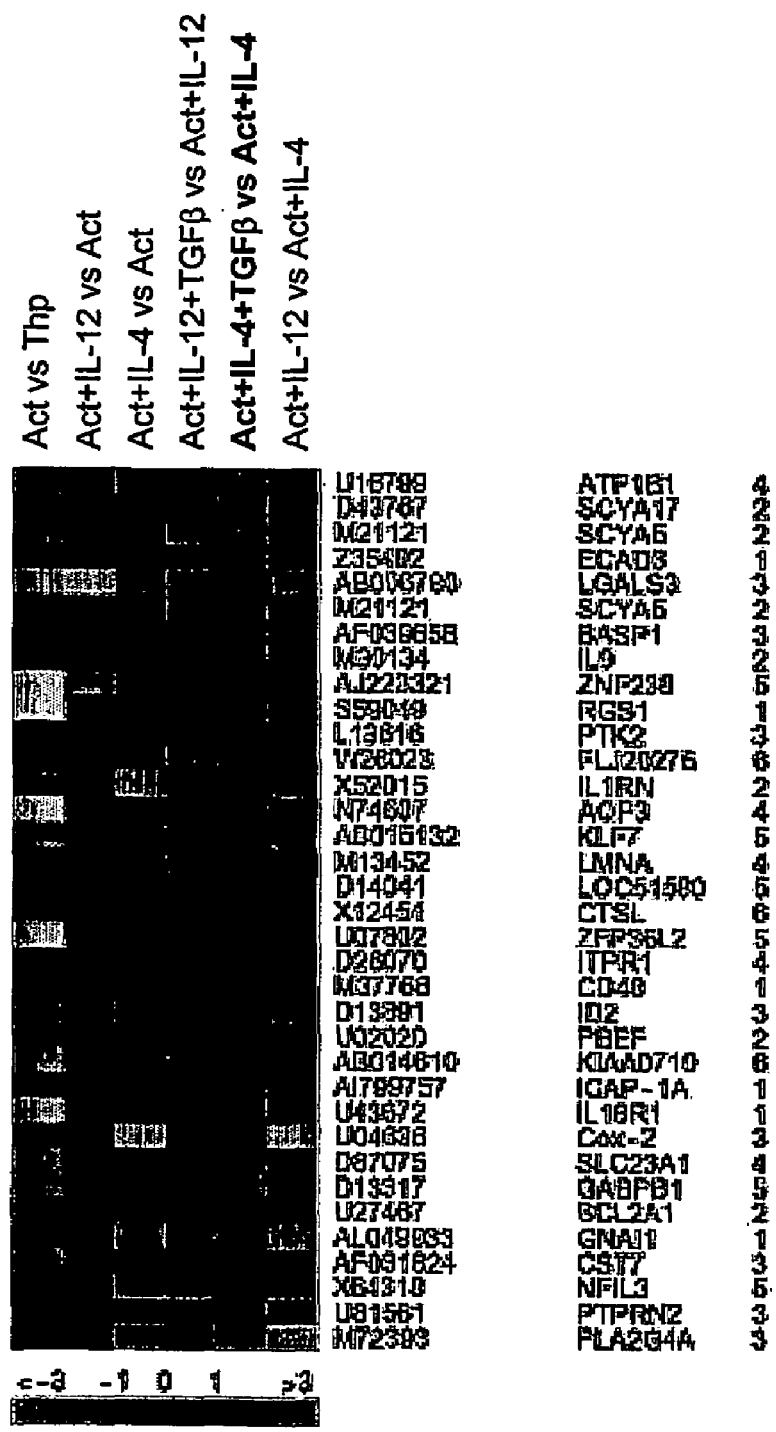

FIGS. 2A-2F. The target genes of activation, IL-12, IL-4 and TGFβ. The CD4+ cells were purified from human cord blood and were activated with plate-bound αCD3 (1000 ng/µl for goating) and 500 ng/µl soluble αCD28. The cells were further polarized with either 2.5 ng/ml of IL-12 for Th1 conditions or 10 ng/ml of IL-4 for Th2 conditions in the presence and absence of 3 ng/ml TGFβ. Part of the activated cells were cultured in "neutral conditions" without any polarizing cytokines. The samples were collected at the time points of 0 h and 48 h. The cRNAs were prepared for oligonucleotide microarray hybridizations and the data was analyzed with the MAS5 program. To identify the target genes of different treatments, the expression profiles of the samples were compared to each other: FIG. 2A shows target genes of activation; FIG. 2B shows target genes of IL-12; FIG. 2C shows target genes of IL-4; FIG. 2D shows target genes of TGFβ in Th1 conditions; FIG. 2E shows target genes of TGFβ in Th2 conditions; and FIG. 2F shows genes differentially expressed by Th1- and Th2-induced cells. The tonal intensities in the figures indicate the differences (signal log ratio) between two treatments. All the irreproducible results or changes below 2-fold (signal log ratio <1) were excluded from the results. Higher cut off (signal log ratio ≧4) for the target genes of activation was used to reduce the number of the genes. The functional groups of the genes are represented as numbers (1. Cell surface molecules, 2. Cytokines, chemolines and other ligands, 3. Enzymes and pathway molecules, 4. Structural molecules and intracellular trafficking, 5. Transcriptional regulation, 6. Unclassified).

Figure 3:
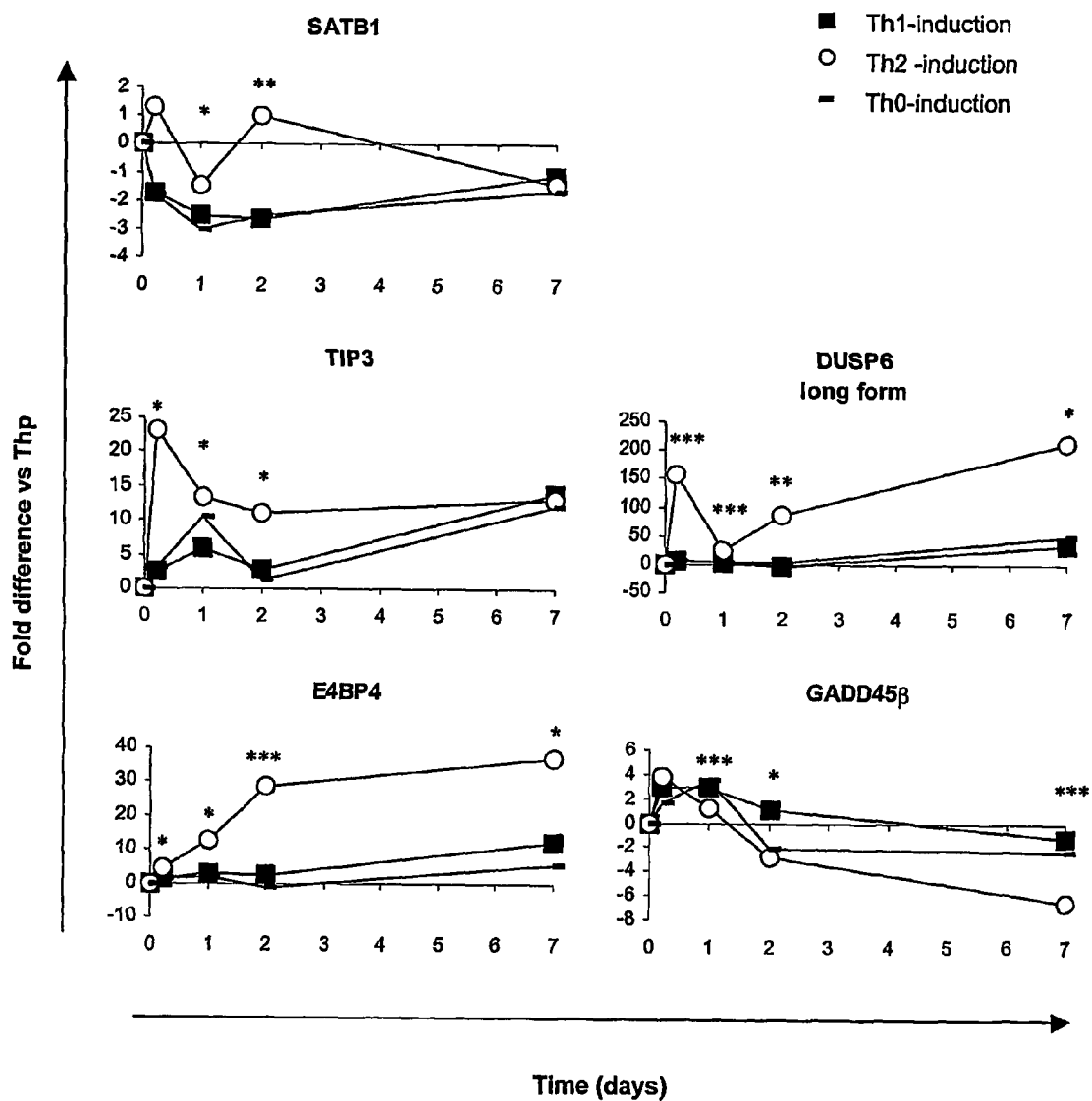

FIG. 3. Validation of oligonucleotide microarray results with Real-Time RT-PCR. For validation of the oligonucleotide array results, long term Th1 and Th2 primary cultures were generated from four individuals as previously described. The priming was performed in the presence of 100 ng/ml PHA (Murex Diagnostics, Chatillon, France) and irradiated CD32-B7 transfected fibroblasts. Th1 cultures were supplemented with 2.5 ng/ml of IL-12 (R&D Systems, Minneapolis, Minn.). Th2 cultures were supplemented with 10 µg/ml of anti-IL-12 (R&D Systems) and 10 ng/ml of IL-4 (R&D System). After 48 hours of priming, 40 U/ml of IL-2 (R&D Systems) was added into the cultures to enhance the proliferation of the lymphocytes. Part of the cells were cultured without any polarizing cytokines in the presence of IL-2 alone. During polarization, samples were collected at time points 0 h, 6 h, 24 h, 48 h or 7 d. Real-time quantitative RT-PCR was performed to quantitate the gene expression levels of SATB1, TIP3, DUSP6, E4BP4 and GADD45β.

DETAILED DESCRIPTION

I. Definitions

The terms "nucleic acid," "polynucleotide" and "oligonucleotide" are used interchangeably and refer to a deoxyribonucleotide or ribonucleotide polymer in either single- or double-stranded form, and unless otherwise limited, encompasses known analogues of natural nucleotides that hybridize to nucleic acids in a manner similar to naturally occurring nucleotides. Unless otherwise indicated, a particular nucleic acid sequence includes the complementary sequence thereof.

The term "target nucleic acid" refers to a nucleic acid (often derived from a biological sample), to which a polynucleotide probe is designed to specifically hybridize. It is either the presence or absence of the target nucleic acid that is to be detected, or the amount of the target nucleic acid that is to be quantified. The target nucleic acid has a sequence that is complementary to the nucleic acid sequence of the corresponding probe directed to the target. The term target nucleic acid can refer to the specific subsequence of a larger nucleic acid to which the probe is directed or to the overall sequence (e.g., gene or mRNA) whose expression level it is desired to detect.

A "probe" or "polynucleotide probe" is an nucleic acid capable of binding to a target nucleic acid of complementary sequence through one or more types of chemical bonds, usually through complementary base pairing, usually through hydrogen bond formation, thus forming a duplex structure. The probe binds or hybridizes to a "probe binding site." A probe can include natural (i.e., A, G, C, or T) or modified bases (7-deazaguanosine, inosine, etc.). A probe can be an oligonucleotide which is a single-stranded DNA. Polynucleotide probes can be synthesized or produced from naturally occurring polynucleotides. In addition, the bases in a probe can be joined by a linkage other than a phosphodiester bond, so long as it does not interfere with hybridization. Thus, probes can include, for example, peptide nucleic acids in which the constituent bases are joined by peptide bonds rather than phosphodiester linkages (see, e.g., Nielsen et al., Science 254, 1497-1500 (1991)). Some probes can have leading and/ or trailing sequences of noncomplementarity flanking a region of complementarity.

A "perfectly matched probe" has a sequence perfectly complementary to a particular target sequence. The probe is typically perfectly complementary to a portion (subsequence) of a target sequence. The term "mismatch probe" refer to probes whose sequence is deliberately selected not to be perfectly complementary to a particular target sequence.

A "primer" is a single-stranded oligonucleotide capable of acting as a point of initiation of template-directed DNA synthesis under appropriate conditions (i.e., in the presence of four different nucleoside triphosphates and an agent for polymerization, such as, DNA or RNA polymerase or reverse transcriptase) in an appropriate buffer and at a suitable temperature. The appropriate length of a primer depends on the intended use of the primer but typically ranges from 15 to 30 nucleotides, although shorter or longer primers can be used as well. Short primer molecules generally require cooler temperatures to form sufficiently stable hybrid complexes with the template. A primer need not reflect the exact sequence of the template but must be sufficiently complementary to hybridize with a template. The term "primer site" refers to the area of the target DNA to which a primer hybridizes. The term "primer pair" means a set of primers including a 5' "upstream primer" that hybridizes with the 5' end of the DNA sequence to be amplified and a 3' "downstream primer" that hybridizes with the complement of the 3' end of the sequence to be amplified.

The term "complementary" means that one nucleic acid is identical to, or hybridizes selectively to, another nucleic acid molecule. Selectivity of hybridization exists when hybridization occurs that is more selective than total lack of specificity. Typically, selective hybridization will occur when there is at least about 55% identity over a stretch of at least 14-25 nucleotides, preferably at least 65%, more preferably at least 75%, and most preferably at least 90%. Preferably, one nucleic acid hybridizes specifically to the other nucleic acid. See M. Kanehisa, *Nucleic Acids Res.* 12:203 (1984).

The terms "polypeptide," "peptide" and "protein" are used interchangeably to refer to a polymer of amino acid residues. The term also applies to amino acid polymers in which one or more amino acids are chemical analogues of a corresponding naturally occurring amino acids.

A "subsequence" or "segment" refers to a sequence of nucleotides or amino acids that comprise a part of a longer sequence of nucleotides or amino acids (e.g., a polypeptide), respectively.

The term "operably linked" refers to functional linkage between a nucleic acid expression control sequence (such as a promoter, signal sequence, or array of transcription factor binding sites) and a second polynucleotide, wherein the expression-control sequence affects transcription and/or translation of the second polynucleotide.

The terms "identical" or percent "identity," in the context of two or more nucleic acids or polypeptides, refer to two or more sequences or subsequences that are the same or have a specified percentage of nucleotides or amino acid residues that are the same, when compared and aligned for maximum correspondence, as measured using a sequence comparison algorithm such as those described below for example, or by visual inspection.

The phrase "substantially identical," in the context of two nucleic acids or polypeptides, refers to two or more sequences or subsequences that have at least 75%, preferably at least 85%, more preferably at least 90%, 95% or higher nucleotide or amino acid residue identity, when compared and aligned for maximum correspondence, as measured using a sequence comparison algorithm such as those described below for example, or by visual inspection. Preferably, the substantial identity exists over a region of the sequences that is at least about 30 residues in length, preferably over a longer region than 50 residues, more preferably at least about 70 residues, and most preferably the sequences are substantially identical over the full length of the sequences being compared, such as the coding region of a nucleotide for example. For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see, e.g., *Current Protocols in Molecular Biology* (Ausubel et al., 1995 supplement).

One useful algorithm for conducting sequence comparisons is PILEUP. PILEUP uses a simplification of the progressive alignment method of Feng & Doolittle, *J. Mol. Evol.* 35:351-360 (1987). The method used is similar to the method described by Higgins & Sharp, *CABIOS* 5:151-153 (1989). Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387-395 (1984).

Another example of algorithm that is suitable for determining percent sequence identity and sequence similarity is the BLAST and the BLAST 2.0 algorithms, which are described in Altschul et al., *J. Mol. Biol.* 215:403-410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra.). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached.

For identifying whether a nucleic acid or polypeptide is within the scope of the invention, the default parameters of the BLAST programs are suitable. The BLASTN program (for nucleotide sequences) uses as defaults a word length (W) of 11, an expectation (E) of 10, M=5, N=−4, and a comparison of both strands. For amino acid sequences, the BLASTP program uses as defaults a word length (W) of 3, an expectation (E) of 10, and the BLOSUM 62 scoring matrix. The TBLATN program (using protein sequence for nucleotide sequence) uses as defaults a word length (W) of 3, an expectation (E) of 10, and a BLOSUM 62 scoring matrix. (See, e.g., Henikoff & Henikoff, *Proc. Natl. Acad. Sci. USA* 89:10915 (1989)).

Another indication that two nucleic acid sequences are substantially identical is that the two molecules hybridize to each other under stringent conditions. "Bind(s) substantially" refers to complementary hybridization between a probe nucleic acid and a target nucleic acid and embraces minor mismatches that can be accommodated by reducing the stringency of the hybridization media to achieve the desired detection of the target polynucleotide sequence. The phrase "hybridizing specifically to", refers to the binding, duplexing, or hybridizing of a molecule only to a particular nucleotide sequence under stringent conditions when that sequence is present in a complex mixture (e.g., total cellular) DNA or RNA.

The term "stringent conditions" refers to conditions under which a probe will hybridize to its target subsequence, but to no other sequences. Stringent conditions are sequence-dependent and will be different in different circumstances. Longer sequences hybridize specifically at higher temperatures. Generally, stringent conditions are selected to be about 5 ° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. (As the target sequences are generally present in excess, at Tm, 50% of the probes are occupied at equilibrium). Typically, stringent conditions will be those in which the salt concentration is less than about 1.0 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g. greater than 50 nucleotides). Stringent conditions can also be achieved with the addition of destabilizing agents such as formamide.

A further indication that two nucleic acid sequences or polypeptides are substantially identical is that the polypeptide encoded by the first nucleic acid is immunologically cross reactive with the polypeptide encoded by the second nucleic acid, as described below. The phrases "specifically binds to a protein" or "specifically imniunoreactive with," when referring to an antibody refers to a binding reaction which is determinative of the presence of the protein in the presence of a heterogeneous population of proteins and other biologics. Thus, under designated immunoassay conditions, a specified antibody binds preferentially to a particular protein and does not bind in a significant amount to other proteins present in the sample. Specific binding to a protein under such conditions requires an antibody that is selected for its specificity for a particular protein. A variety of immunoassay formats may be used to select antibodies specifically immunoreactive with a particular protein. For example, solid-phase ELISA immunoassays are routinely used to select monoclonal antibodies specifically immunoreactive with a protein. See, e.g., Harlow and Lane (1988) *Antibodies, A Laboratory Manual*, Cold Spring Harbor Publications, New York, for a description of immunoassay formats and conditions that can be used to determine specific immunoreactivity.

"Conservatively modified variations" of a particular polynucleotide sequence refers to those polynucleotides that encode identical or essentially identical amino acid sequences, or where the polynucleotide does not encode an amino acid sequence, to essentially identical sequences. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleic acid variations are "silent variations," which are one species of "conservatively modified variations." Every polynucleotide sequence described herein which encodes a polypeptide also describes every possible silent variation, except where otherwise noted. One of skill will recognize that each codon in a nucleic acid (except AUG, which is ordinarily the only codon for methionine) can be modified to yield a functionally identical molecule by standard techniques. Accordingly, each "silent variation" of a nucleic acid which encodes a polypeptide is implicit in each described sequence.

A polypeptide is typically substantially identical to a second polypeptide, for example, where the two peptides differ only by conservative substitutions. A "conservative substitution," when describing a protein, refers to a change in the amino acid composition of the protein that does not substantially alter the protein's activity. Thus, "conservatively modified variations" of a particular amino acid sequence refers to amino acid substitutions of those amino acids that are not critical for protein activity or substitution of amino acids with other amino acids having similar properties (e.g., acidic, basic, positively or negatively charged, polar or non-polar, etc.) such that the substitutions of even critical amino acids do not substantially alter activity. Conservative substitution tables providing functionally similar amino acids are well-known in the art. See, e.g., Creighton (1984) *Proteins*, W.H. Freeman and Company. In addition, individual substitutions, deletions or additions which alter, add or delete a single amino acid or a small percentage of amino acids in an encoded sequence are also "conservatively modified variations."

The term "naturally occurring" as applied to an object refers to the fact that an object can be found in nature. For example, a polypeptide or polynucleotide sequence that is present in an organism that can be isolated from a source in nature and which has not been intentionally modified by humans in the laboratory is naturally occurring.

The term "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively.

Antibodies exist as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to VH-CH1 by a disulfide bond. The F(ab)'$_2$ may be reduced under mild conditions to break the disulfide linkage in the hinge region thereby converting the (Fab')$_2$ dimer into an Fab' monomer. The Fab' monomer is essentially an Fab with part of the hinge region (see, *Fundamental Immunology*, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Preferred antibodies include single chain antibodies, more preferably single chain Fv (scFv) antibodies in which a variable heavy and a variable light chain are joined together (directly or through a peptide linker) to form a continuous polypeptide.

A single chain Fv ("scFv" or "scFv") polypeptide is a covalently linked VH::VL heterodimer which may be expressed from a nucleic acid including VH- and VL- encoding sequences either joined directly or joined by a peptide-encoding linker. Huston, et al. *Proc. Nat. Acad. Sci. USA*, 85:5879-5883 (1988). A number of structures for converting the naturally aggregated—but chemically separated light and heavy polypeptide chains from an antibody V region into an scFv molecule which will fold into a three dimensional structure substantially similar to the structure of an antigen-binding site. See, e.g. U.S. Pat. Nos. 5,091,513 and 5,132,405 and 4,956,778.

An "antigen-binding site" or "binding portion" refers to the part of an immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions" or "FRs". Thus, the term "FR" refers to amino acid sequences that are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen binding "surface". This surface mediates recognition and binding of the target antigen. The three hypervariable regions of each of the heavy and light chains are referred to as "complementarity determining regions" or "CDRs" and are characterized, for example by Kabat et al. *Sequences of proteins of immunological interest*, 4th ed. U.S. Dept. Health and Human Services, Public Health Services, Bethesda, Md. (1987).

The term "antigenic determinant" refers to the particular chemical group of a molecule that confers antigenic specificity.

The term "epitope" generally refers to that portion of an antigen that interacts with an antibody. More specifically, the term epitope includes any protein determinant capable of specific binding to an immunoglobulin or T-cell receptor. Specific binding exists when the dissociation constant for antibody binding to an antigen is $\leq 1$ µM, preferably $\leq 100$ nM and most preferably $\leq 1$ nM. Epitopic determinants usually consist of chemically active surface groupings of molecules such as amino acids and typically have specific three dimensional structural characteristics, as well as specific charge characteristics.

The term "specific binding" (and equivalent phrases) refers to the ability of a binding moiety (e.g., a receptor, antibody, ligand or antiligand) to bind preferentially to a particular target molecule (e.g., ligand or antigen) in the presence of a heterogeneous population of proteins and other biologics (i.e., without significant binding to other components present in a test sample). Typically, specific binding between two entities, such as a ligand and a receptor, means a binding affinity of at least about $10^6$ M$^{-1}$, and preferably at least about $10^7$, $10^8$, $10^9$, or $10^{10}$ M$^{-1}$.

A "subject" generally refers to an organism from which lymphocytes can be obtained. Usually the subject is a mammal. The mammal can be a primate (e.g., a human, monkey, ape, or chimpanzee), or a non-primate (e.g., a mouse).

II. Overview

Many biological functions are controlled through changes in the expression of various genes by transcriptional (e.g., through control of initiation, RNA processing, etc.) and/or translational control. For example, fundamental biological processes such as cell cycle, cell differentiation and cell death, are often characterized by the variations in the expression levels of groups of genes (see e.g. WO02059271). The changes in gene expression also are associated with pathogenesis. Thus, changes in the expression levels of particular genes can indicate the presence and progression of various diseases.

According to the invention, genes that are differentially expressed during cytokine induced CD4+ lymphocyte polarization in both the presence and absence of TGFβ have been discovered. One or more of these target genes can be used as part of an "an expression profile" that is representative of a particular state of a lymphocyte. Identification of these new target genes enable immune-mediated diseases to be analyzed more reliably. These results also provide new insights into T cell differentiation and reveal new potential target genes for the therapy of diseases such as asthma. These differentially expressed genes and their corresponding proteins can also be utilized as "markers" that characterize particular cellular states for lymphocytes.

The differentially expressed genes that have been identified can be utilized in a variety of methods for classifying lymphocytes, as well as diagnosing and treating immune-mediated diseases (e.g., asthma, allergic responses and autoimmune diseases). Kits and devices including one or more of the differentially expressed genes, proteins encoded by these genes and/or antibodies that bind the proteins are also provided.

For example, the differentially expressed genes can be used to in screening methods to identify compounds that modulate the expression or activity of the differentially expressed genes. Such methods can be utilized, for example, for the identification of compounds that can treat symptoms of disorders related to expression of proteins encoded by the differentially expressed genes. In addition, the invention encompasses methods for treating immune-mediated diseases or disorders by administering compounds and/or other substances that modulate the activity of one or more of the target genes or target gene products. Such compounds and other substances can effect the modulation either on the level of target gene expression or target protein activity. Certain classification methods that are also provided involve determining the level of one or more of the differentially expressed genes to determine whether a lymphocyte has been polarized in the Th1 or Th2 direction.

III. Differentially Expressed Genes

As described more fully in the examples below, an initial set of experiments were conducted to identify the gene expression profiles of CD4+ cells induced in the Th1 and Th2 directions in the presence and absence of TGFβ. This allowed those genes involved in early polarization to be identified, as well providing insight regarding which genes are involved in the immunosuppressive effect of TGFβ. Another set of experiments was then conducted to identify those genes in lymphocytes that are regulated by the cytokines IL-12 and IL-4. Most of the differentially expressed genes were identified using oligonucleotide arrays; the differential expression of certain genes was confirmed using real-time PCR approaches.

The differentially expressed genes include, for instance, those identified under the following sets of conditions or states:

(a) CD4+ cells activated by contact with CD3/CD28 versus unactivated CD4+ cells; these genes correspond to target genes of activation (see, e.g. FIG. 2A);

(b) activated CD4+ cells further activated with IL-12 versus activated CD4+ cells; these genes are representative of Th1 cells and correspond to target genes of IL-12 (see, e.g. FIG. 2B);

c) activated CD4+ cells further activated with IL-4 versus activated CD4+ cells; these genes are representative of Th2 cells and correspond to target genes of IL-4 (see, e.g. FIG. 2C);

d) activated cells polarized with IL-12 exposed to TGFβ versus similar cells not exposed to TGFβ; these correspond to genes in Th1 cells that are affected by TGFβ (see, e.g. FIG. 2D);

e) activated cells polarized with IL-4 exposed to TGFβ versus similar cells not exposed to TGFβ; these correspond to genes in Th2 cells that are affected by TGFβ (see, e.g. FIG. 2E); and f) genes differentially expressed in Th1 cells versus Th2 cells (see, e.g. FIG. 2F).

As discussed in greater detail below, knowledge of the nucleic acids that are up-regulated or down-regulated in the various types of lymphocytes and in different cellular states provides the basis for a number of different screening, treatment and diagnostic methods, in addition to devices to carry out these methods. The differentially expressed genes include both "fingerprint genes" and "control genes." "Fingerprint genes" are those nucleic acids that correlate with a particular type of lymphocyte (e.g., Th1 or Th2), or a particular cellular state (e.g., activated or non-activated). As described in greater detail below, fingerprint genes can be used in the development of a variety of different screening and diagnostic methods to classify types of lymphocytes and/or to aid in the diagnosis of particular disease conditions. A "control gene" is one that encodes a protein that is involved in a lymphocyte assuming a particular state or becoming a particular type of cell. Because of the role such genes play, control genes are useful targets for the development of compound discovery programs and pharmaceutical development such as described infra. In some instances, a fingerprint gene can be a control gene and vice versa.

Expression levels for combinations of differentially expressed genes, in particular fingerprint genes, can be used to develop "expression profiles" that are characteristic of a particular type of lymphocyte or cellular state. Expression profiles as used herein refers to the pattern of gene expression corresponding to at least one differentially expressed genes, but typically includes a plurality of genes. For instance, an expression profile can include at least 1, 2, 3, 4 or 5 differentially expressed genes, but in other instances can include at least 6, 7, 8, 9, 10, 12, 14, 16, 18, 20, 25, 30, 35, 40, 45 or 50 or more differentially expressed genes. In some instances, expression profiles include all of the differentially expressed genes known for a particular type of lymphocyte or cellular state. So, for example, certain expression profiles include a measure (quantitative or qualitative) of the expression level for each of the differentially expressed genes in one or more of the tables or figures (e.g., Table 1 or Table 2 and/or Table6).

The pattern of expression associated with gene expression profiles can be defined in several ways. For example, a gene expression profile can be the absolute (e.g. a measured value) or relative transcript level of any number of particular differentially expressed genes. In other instances, a gene expression profile can be defined by comparing the level of expression of a variety of genes in one state to the level of expression of the same genes in another state (e.g., activated versus unactivated), or between one cell type and another cell type (e.g., Th1 versus Th2).

As used herein, the term "differentially expressed gene" or "differentially expressed nucleic acid" refers to the specific sequence as set forth in the particular GenBank entry that is provided herein (see, e.g., the tables and figures). The term, however, is also intended to include more broadly naturally occurring sequences (including allelic variants of those listed for the GenBank entries), as well as synthetic and intentionally manipulated sequences (e.g., nucleic acids subjected to site-directed mutagenesis). It is noted that the sequences of the target genes listed in the tables and figures are available in the public databases. The tables provide the accession number and name for each of the sequences. The sequences of the genes in GenBank are herein expressly incorporated by reference in their entirety as of the filing date of this application (see www.ncbi.nim.nih.gov).

Differentially expressed nucleic acids also include sequences that are complementary to the listed sequences, as well as degenerate sequences resulting from the degeneracy of the genetic code. Thus, the differentially expressed nucleic acids include: (a) nucleic acids having sequences corresponding to the sequences as provided in the listed GenBank accession number; (b) nucleic acids that encode amino acids encoded by the nucleic acids of (a); (c) a nucleic acid that hybridizes under stringent conditions to a complement of the nucleic acid of (a); and (d) nucleic acids that hybridize under stringent conditions to, and therefore are complements of, the nucleic acids described in (a) through (c). The differentially expressed nucleic acids of the invention also include: (a) a deoxyribonucleotide sequence complementary to the full-length nucleotide sequences corresponding to the listed GenBank accession numbers; (b) a ribonucleotide sequence complementary to the full-length sequence corresponding to the listed GenBank accession numbers; and (c) a nucleotide sequence complementary to the deoxyribonucleotide sequence of (a) and the ribonucleotide sequence of (b). The differentially expressed nucleic acids further include fragments of the foregoing sequences. For example, nucleic acids including 10, 12, 14, 16, 18, 20, 22, 24, 26, 28, 30, 40, 50, 60, 70, 80, 90, 100, 125, 150, 175, 200, 225, 250, 275 or 300 contiguous nucleotides (or any number of nucleotides therebetween) from a differentially expressed nucleic acid are included. Such fragments are useful, for example, as primers and probes for hybridizing fill-length differentially expressed nucleic acids (e.g., in detecting and amplifying such sequences).

In some instances, the differentially expressed nucleic acids include conservatively modified variations. Thus, for example, in some instances, the differentially expressed nucleic acids are modified. One of skill will recognize many ways of generating alterations in a given nucleic acid construct. Such well-known methods include site-directed mutagenesis, PCR amplification using degenerate polynucleotides, exposure of cells containing the nucleic acid to mutagenic agents or radiation and chemical synthesis of a desired polynucleotide (e.g., in conjunction with ligation and/or cloning to generate large nucleic acids). See, e.g., Giliman and Smith (1979) *Gene* 8:81-97, Roberts et al. (1987) *Nature* 328: 731-734). When the differentially expressed nucleic acids are incorporated into vectors, the nucleic acids can be combined with other sequences including, but not limited to, promoters, polyadenylation signals, restriction enzyme sites and multiple cloning sites. Thus, the overall length of the nucleic acid can vary considerably.

Certain differentially expressed nucleic acids of the invention include polynucleotides that are substantially identical to a polynucleotide sequence as set forth in SEQ ID NO:1. Such nucleic acids can function as new markers for certain types of lymphocytes and for different cellular states for lymphocytes. For example, the invention includes polynucleotide sequences that are at least 80%, 85%, 90%, 92%, 94%, 96%, 98% or 100% identical to the polynucleotide sequences provided in the GenBank entries listed in the tables. Identity is typically measured over at least 40, 50, 60, 70, 80, 90 or 100 contiguous nucleotides. In other instances, identity is measured over a region of at least 150, 200, or 250 nucleotides in length. In yet other instances, the region of similarity exceeds 250 nucleotides in length and extends for at least 300, 350, 400, 450 or 500 nucleotides in length, or over the entire length of the sequence.

As described above, sequence identity comparisons can be conducted using a nucleotide sequence comparison algorithm such as those know to those of skill in the art. For example, one can use the BLASTN algorithm. Suitable parameters for use in BLASTN are wordlength (W) of 11, M=5 and N=−4 and the identity values and region sizes just described.

B. Preparation of Differentially Expressed Genes

The differentially expressed nucleic acids can be obtained by any suitable method known in the art, including, for example: (1) hybridization of genomic or cDNA libraries with probes to detect homologous nucleotide sequences; (2) antibody screening of expression libraries to detect cloned DNA fragments with shared structural features; (3) various amplification procedures such as polymerase chain reaction (PCR) using primers capable of annealing to the nucleic acid of interest; and (4) direct chemical synthesis.

The desired nucleic acids can also be cloned using well-known amplification techniques. Examples of protocols sufficient to direct persons of skill through in vitro amplification methods, including the polymerase chain reaction (PCR) the ligase chain reaction (LCR), Qβ-replicase amplification and other RNA polymerase mediated techniques, are found in Berger, Sambrook, and Ausubel, as well as Mullis et al. (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) *C&EN* 3647; *The Journal Of NIH Research* (1991) 3: 81-94; (Kwoh et al. (1989) *Proc. Natl. Acad. Sci. USA* 86: 1173; Guatelli et al. (1990) *Proc. Natl. Acad. Sci. USA* 87: 1874; Lomell et al. (1989) *J. Clin. Chem.* 35: 1826; Landegren et al. (1988) *Science* 241: 1077-1080; Van Brunt (1990) *Biotechnology* 8: 291-294; Wu and Wallace (1989) *Gene* 4: 560; and Barringer et al. (1990) *Gene* 89: 117. Improved methods of cloning in vitro amplified nucleic acids are described in Wallace et al., U.S. Pat. No. 5,426,039.

As an alternative to cloning a nucleic acid, a suitable nucleic acid can be chemically synthesized. Direct chemical synthesis methods include, for example, the phosphotriester method of Narang et al. (1979) *Meth. Enzymol.* 68: 90-99; the phosphodiester method of Brown et al. (1979) *Meth. Enzymol.* 68: 109-151; the diethylphosphoramidite method of Beaucage et al. (1981) *Tetra. Lett.,* 22: 1859-1862; and the solid support method described in U.S. Pat. No. 4,458,066. Chemical synthesis produces a single stranded polynucleotide. This can be converted into double stranded DNA by hybridization with a complementary sequence, or by polymerization with a DNA polymerase using the single strand as a template. While chemical synthesis of DNA is often limited to sequences of about 100 bases, longer sequences can be obtained by the ligation of shorter sequences. Alternatively, subsequences can be cloned and the appropriate subsequences cleaved using appropriate restriction enzymes. The fragments can then be ligated to produce the desired DNA sequence.

C. Utility of Differentially Expressed Nucleic Acids and Expression Profiles

As alluded to above and described in greater detail below, the differentially expressed nucleic acids that are provided can be used as markers in a variety of screening and diagnostic methods. For example, the differentially expressed nucleic acids find utility as hybridization probes or amplification primers. In certain instances, these probes and primers are fragments of the differentially expressed nucleic acids of the lengths described earlier in this section. Such fragments are generally of sufficient length to specifically hybridize to an RNA or DNA in a sample obtained from a subject. The nucleic acids are typically 10-30 nucleotides in length, although they can be longer as described above. The probes can be used in a variety of different types of hybridization experiments, including, but not limited to, Northern blots and Southern blots and in the preparation of custom arrays (see infra). The differentially expressed nucleic acids can also be used in the design of primers for amplifying the differentially expressed nucleic acids and in the design of primers and probes for quantitative RT-PCR The primers most frequently include about 20 to 30 contiguous nucleotides of the differentially expressed nucleic acids to obtain the desired level of stability and thus selectivity in amplification, although longer sequences as described above can also be utilized.

Hybridization conditions are varied according to the particular application. For applications requiring high selectivity (e.g., amplification of a particular sequence), relatively stringent conditions are utilized, such as 0.02 M to about 0.10 M NaCl at temperatures of about 50° C. to about 70° C. High stringency conditions such as these tolerate little, if any, mismatch between the probe and the template or target strand of the differentially expressed nucleic acid. Such conditions are useful for isolating specific genes or detecting particular mRNA transcripts, for example.

Other applications, such as substitution of amino acids by site-directed mutagenesis, require less stringency. Under these conditions, hybridization can occur even though the sequences of the probe and target nucleic acid are not perfectly complementary, but instead include one or more mismatches. Conditions can be rendered less stringent by increasing the salt concentration and decreasing temperature. For example, a medium stringency condition includes about 0.1 to 0.25 M NaCl at temperatures of about 37° C. to about 55° C. Low stringency conditions include about 0.15 M to about 0.9 M salt, at temperatures ranging from about 20 C. to about 55° C.

V. Proteins

A. General

The differentially expressed nucleic acids that have been identified can be inserted into any of a number of known expression systems to generate large amounts of the protein encoded by the gene or gene fragment. Such proteins can then be utilized in the preparation of antibodies. Proteins encoded by target genes can be utilized in the compound development programs described below and in the preparation of various diagnostics (e.g., antibody arrays).

The polypeptides can be isolated from natural sources, and/or prepared according to recombinant methods, and/or prepared by chemical synthesis, and/or prepared using a combination of recombinant methods and chemical synthesis. Besides substantially full-length polypeptides, biologically active fragments of the polypeptides are also provided. Biological activity can include, for example, antibody binding (e.g., the fragment competes with a full-length polypeptide) and immunogenicity (i.e., possession of epitopes that stimulate B- or T-cell responses against the fragment). Such fragments generally comprise at least 5 contiguous amino acids, typically at least 6 or 7 contiguous amino acids, in other instances 8 or 9 contiguous amino acids, usually at least 10, 11 or 12 contiguous amino acids, in still other instances at least 13 or 14 contiguous amino acids, in yet other instances at least 16 contiguous amino acids, and in some cases at least 20, 40, 60 or 80 contiguous ammo acids.

Often the polypeptides will share at least one antigenic determinant in common with the amino acid sequence of the full-length polypeptide. The existence of such a common determinant is evidenced by cross-reactivity of the variant protein with any antibody prepared against the full-length polypeptide. Cross-reactivity can be tested using polyclonal sera against the full-length polypeptide, but can also be tested using one or more monoclonal antibodies against the full-length polypeptide.

The polypeptides include conservative variations of the naturally occurring polypeptides. Such variations can be minor sequence variations of the polypeptide that arise due to natural variation within the population (e.g., single nucleotide polymorphisms) or they can be homologs found in other species. They also can be sequences that do not occur naturally but that are sufficiently similar so that they function similarly and/or elicit an immune response that cross-reacts with natural forms of the polypeptide. Sequence variants can be prepared by standard site-directed mutagenesis techniques. The polypeptide variants can be substitutional, insertional or deletion variants. Deletion variants lack one or more residues of the native protein that are not essential for function or immunogenic activity (e.g., polypeptides lacking transmembrane or secretory signal sequences). Substitutional variants involve conservative substitutions of one amino acid residue for another at one or more sites within the protein and can be designed to modulate one or more properties of the polypeptide such as stability against proteolytic cleavage. Insertional variants include, for example, fusion proteins such as those used to allow rapid purification of the polypeptide and also can include hybrid proteins containing sequences from other polypeptides, which are homologues of the polypeptide. The foregoing variations can be utilized to create equivalent, or even an improved, second-generation polypeptide. Preparation of variants is well known in the art (see, e.g., Creighton (1984) *Proteins*, W.H. Freeman and Company, which is incorporated herein by reference in its entirety for all purposes).

The polypeptides that are provided also include those in which the polypeptide has a modified polypeptide backbone. Examples of such modifications include chemical derivatizations of polypeptides, such as acetylations and carboxylations. Modifications also include glycosylation modifications and processing variants of a typical polypeptide. Such processing steps specifically include enzymatic modifications, such as ubiquitinization and phosphorylation. See, e.g., Hershko & Ciechanover, *Ann. Rev. Biochem.* 51:335-364 (1982). Also included are mimetics, which are peptide-containing molecules that mimic elements of protein secondary structure (see, e.g., Johnson, et al., "Peptide Turn Mimetics" in *Biotechnology and Pharmacy*, (Pezzuto et al., Eds.), Chapman and Hall, New York (1993)). Peptide mimetics are typically designed so that side chain groups extending from the backbone are oriented such that the side chains of the mimetic can be involved in molecular interactions similar to the interactions of the side chains in the native protein.

B. Production of Polypeptides

1. Recombinant Technologies

The polypeptides encoded by the differentially expressed nucleic acids can be expressed in hosts after the coding sequences have been operably linked to an expression control sequence in an expression vector. Expression vectors are typically replicable in the host organisms either as episomes or as an integral part of the host chromosomal DNA. Expression vectors commonly contain selection markers, e.g., tetracycline resistance or hygromycin resistance, to permit detection and/or selection of those cells transformed with the desired DNA sequences (see, e.g., U.S. Pat. No. 4,704,362).

A differentially expressed gene typically is placed under the control of a promoter that is functional in the desired host cell to produce relatively large quantities of a polypeptide of the invention. An extremely wide variety of promoters are well known to those of skill, and can be used in the expression vectors, depending on the particular application. Ordinarily, the promoter selected depends upon the cell in which the promoter is to be active. Other expression control sequences such as ribosome binding sites, transcription termination sites and the like are also optionally included. Constructs that include one or more of such control sequences are termed "expression cassettes." Accordingly, expression cassettes are provided into which the differentially expressed nucleic acids are incorporated for high level expression of the corresponding protein in a desired host cell.

A wide variety of cloning and in vitro amplification methods suitable for the construction of recombinant nucleic acids is described, for example, in Berger and Kimmel, *Guide to Molecular Cloning Techniques, Methods in Enzymology*, Volume 152, Academic Press, Inc., San Diego, Calif. (Berger); and "Current Protocols in Molecular Biology," F. M. Ausubel et al., eds., *Current Protocols*, a joint venture between Greene Publishing Associates, Inc. and John Wiley & Sons, Inc., (1998 Supplement) (Ausubel).

2. Naturally Occurring Polypeptides

Naturally occurring polypeptides encoded by the differentially expressed genes can also be isolated using conventional techniques such as affinity chromatography. For example, polyclonal or monoclonal antibodies can be raised against the polypeptide of interest and attached to a suitable affinity column by well-known techniques. See, e.g., Hudson & Hay, *Practical Immunology* (Blackwell Scientific Publications, Oxford, UK, 1980), Chapter 8 (incorporated by reference in its entirety). Peptide fragments can be generated from intact polypeptides by chemical or enzymatic cleavage methods known to those of skill in the art.

3. Other Methods

Alternatively, the polypeptides encoded by differentially expressed genes or gene fragments can be synthesized by chemical methods or produced by in vitro translation systems using a polynucleotide template to direct translation. Methods for chemical synthesis of polypeptides and in vitro translation are well-known in the art, and are described further by Berger & Kimmel, *Methods in Enzymology, Volume* 152, *Guide to Molecular Cloning Techniques*, Academic Press, Inc., San Diego, Calif., 1987 (incorporated by reference in its entirety).

C. Utility

The polypeptides can be used to generate antibodies that specifically bind to epitopes associated with the polypeptides or fragments thereof. Commercially available computer sequence analysis can be used to determine the location of the predicted major antigenic determinant epitopes of the polypeptide (e.g., MacVector from IBI, New Haven, Conn.). Once such an analysis has been performed, polypeptides can be prepared that contain at least the essential structural features of the antigenic determinant and can be utilized in the production of antisera against the polypeptide. Minigenes or gene fusions encoding these determinants can be constructed and inserted into expression vectors such as those described above using standard techniques. The major antigenic determinants can also be determined empirically in which portions of the gene encoding the polypeptide are expressed in a recombinant host, and the resulting proteins tested for their ability to elicit an immune response. For example, PCR can be used to prepare a range of cDNAs encoding polypeptides lacking successively longer fragments of the C-terminus of the polypeptide. The immunoprotective activity of each of these polypeptides then identifies those fragments or domains of the polypeptide that are essential for this activity. Further experiments in which only a small number or amino acids are removed at each iteration then allows the location of the antigenic determinants of the polypeptide.

Polypeptides encoded by target genes can be utilized in the development of pharmaceutical compositions, for example that modulate gene products associated cancerous cells. The process for identifying such polypeptides and subsequent compound development is described further below.

VI. Exemplary Screening, Diagnostic and Classification Methods

A. General Considerations

Certain methods that are provided involve determining the expression level of one or more of the differentially expressed genes in a test cell population with the expression level of the same genes in a control cell population, or comparing the expression profile for one sample with an expression profile determined for another sample. The level of expression of the differentially expressed nucleic acids can be determined at either the nucleic acid level or the protein level. Thus, the phrase "determining the expression level," "preparing a gene expression profile," and other like phrases when used in reference to the differentially expressed nucleic acids means that transcript levels and/or levels of protein encoded by the differentially encoded nucleic acids are detected. When determining the level of expression, the level can be determined qualitatively, but generally is determined quantitatively.

Based upon the sequence information that is disclosed herein, coupled with the nucleic acid and protein detection methods that are described herein and that are known in the art, expression levels of these genes can readily determined. If transcript levels are determined, they can be determined using routine methods. For instance, the sequence information provided herein (e.g., GenBank sequence entries) can be used to construct nucleic acid probes using conventional methods such as various hybridization detection methods (e.g., Northern blots). Alternatively, the provided sequence information can be used to generate primers that in turn are used to amplify and detect differentially expressed nucleic acids that are present in a sample (e.g., quantitative RT-PCR methods). If instead expression is detected at the protein level, encoded protein can be detected and optionally quantified using any of a number of established techniques. One common approach is to use antibodies that specifically bind to the protein product in immunoassay methods. Additional details regarding methods of conducting differential gene expression are provided infra.

Expression levels can be detected for one, some, or all of the differentially expressed nucleic acids that are listed in one or more of the tables (e.g. Table 1, or Table 2, or Table 6). With some methods, the expression levels for only 1, 2, 3, 4 or 5 differentially expressed nucleic acids are determined. In other methods, expression levels for at least 6, 7, 8, 9 or 10 differentially expressed nucleic acids are determined. In still other methods, expression levels for at least 15, 20, 25, 30, 35, 40, 45, 50, 55, or 60 differentially expressed nucleic acids are determined. In yet other methods, all of the differentially expressed genes in one or more of the tables are determined.

Determination of expression levels is typically done with a test sample taken from a test cell population. As used herein, the term "population" when used in reference to a cell can mean a single cell, but typically refers to a plurality of cells (e.g., a tissue sample). Certain screening methods are performed with test cells that are "capable of expressing" one or more of the differentially expressed nucleic acids. As used in this context, the phrase "capable or expressing" means that the gene of interest is in intact form and can be expressed within the cell.

A number of the methods that are provided involve a comparison of expression levels for certain differentially expressed nucleic acids in a "test cell" with the expression levels for the same nucleic acids in a "control cell" (also sometimes referred to as a "control sample," a "reference cell," a "reference value," or simply a "control"). Other methods involve a comparison between one expression profile and a baseline expression profile. In either case, the expression level for the control cell or baseline expression profile essentially establishes a baseline against which an experimental value is compared. The comparison of expression levels are meant to be interpreted broadly with respect to what is meant by: 1) the term "cell", 2) the time at which the expression levels for test and control cells are determined, and 3) with respect to the measure of the expression levels.

So, for example, although the term "test cell" and "control cell" is used for convenience, the term "cell" is meant to be construed broadly. A cell, for instance, can also refer to a population of cells (e.g., a tissue sample), just as a population of cells can have a single member. The cell may in some instances be a sample that is derived from a cell (e.g., a cell lysate, a homogenate, or a cell fraction). In general samples can be obtained from various sources, particularly sources of lymphocytes.

With respect to timing, comparison of expression levels can be done contemporaneously (e.g., a test and control cell are each contacted with a test agent in parallel reactions). The comparison alternatively can be conducted with expression levels that have been determined at temporally distinct times. As an example, expression levels for the control cell can be collected prior to the expression levels for the test cell and stored for future use (e.g., expression levels stored on a computer compatible storage medium).

The expression level for a control cell or baseline expression profile (e.g., baseline value) can be a value for a single cell or it can be an average, mean or other statistical value determined for a plurality of cells. As an example, the expression level for a control cell can be the average of the expression levels for a population of subjects (e.g., subjects not having an immune-related disorder such as asthma). In other instances, the value for each expression level for the control cell is a range of values representative of the range observed for a particular population. Expression level values can also be either qualitative or quantitative. The values for expression levels can also optionally be normalized with respect to the expression level of a nucleic acid that is not one of the markers under analysis.

The comparative analysis required in some methods involves determining whether the expression level values are "comparable" (or similar"), or "differ" from one another. In some instances, the expression levels for a particular marker in test and control cells are considered similar if they differ from one another by no more than the level of experimental error. Often, however, expression levels are considered similar if the level in the test cell differs by less than 5%, 10%, 20%, 50%, 100%, 150%, or 200% with respect to the control cell. It thus follows that in some instances the expression level for a particular marker in the test cell is considered to differ from the expression level for the same marker in the control cell if the difference is greater than the level of experimental error, or if it is greater than 5%, 10%, 20%, 50%, 100%, 150% or 200%. In some methods, the comparison involves a determination of whether there is a "statistically significant difference" in the expression level for a marker in the test and control cells. A difference is generally considered to be "statistically significant" if the probability of the observed difference occurring by chance (the p-value) is less than some predetermined level. As used herein a "statistically significant difference" refers to a p-value that is <0.05, preferably <0.01 and most preferably <0.001. If gene expression is increased sufficiently such that it is different (as just defined) relative to the control cell or baseline, the expression of that gene is considered "up-regulated" or "increased." If, instead, gene expression is decreased so it differs from the control cell or baseline value, the expression of that gene is "down-regulated" or "decreased."

Comparison of the expression levels between test and control cells can involve comparing levels for a single marker or a plurality of markers (e.g., when expression profiles are compared). When the expression level for a single marker is determined, whether expression levels between the test and control cell are similar or different involves a comparison of the expression level of the single marker. When, however, expression levels for multiple markers are compared, the comparison analysis can involve two analyses: 1) a determination for each marker examined whether the expression level is similar between the test and control cells, and 2) a determination of how many markers from the group of markers examined show similar or different expression levels. The first determination is done as just described. The second determination typically involves determining whether at least 50% of the markers examined show similarity in expression levels. However, in methods were more stringent correlations are required, at least 60%, 70%, 80%, 90%, 95% or 100% of the markers must show similar expression levels for the expression levels of the group of markers examined considered to be similar between the test and control cells.

B. Screening Methods

1. Exemplary Approaches

Monitoring changes in gene expression can provide certain advantages during drug screening and development. Often drugs are pre-screened for the ability to interact with a major target without regard to other effects the drugs have on cells. Often such other effects cause toxicity in the whole animal, which prevent the development and use of the potential drug. These global changes in gene expression provide useful markers for diagnostic uses as well as markers that can be used to monitor disease states, disease progression, and drug metabolism. Thus, these expression profiles of genes provide molecular tools for evaluating drug toxicity, drug efficacy, and disease monitoring.

Changes in the expression profile from a baseline profile (e.g. the data in Table 1) can be used as an indication of such effects. Those skilled in the art can use any of a variety of known techniques to evaluate the expression of one or more of the genes and/or gene fragments identified in the present application in order to observe changes in the expression profile in a cell or sample of interest. Comparison of the expression data, as well as available sequence or other information may be done by researcher or diagnostician or may be done with the aid of a computer and databases.

In some screening methods, compounds and molecules are screened to identify those that affect expression of a target gene or some other gene involved in regulating the expression of a target gene (e.g., by interacting with the regulatory region or transcription factors of a target gene). Compounds are also screened to identify those that affect the activity of such proteins (e.g., by inhibiting target gene activity) or the activity of a molecule involved in the regulation of a target gene.

So, for example, in some methods potential drug compounds are screened to determine if application of the compound alters the expression of one or more of the target genes identified herein. This may be useful, for example, in determining whether a particular compound is effective in treating asthma or other immune-mediated disease. In the case in which the expression of a gene during the CD4+ lymphocyte polarization is affected by the potential drug compound, the compound is indicated in the treatment of asthma or other immune-mediated disease. Similarly, a drug compound which causes expression of a gene which is normally down-regulated during the CD4+ lymphocyte polarization, may be indicated in the treatment of the same diseases.

According to the present invention, the target genes listed in Table 2 or Table 6 may also be used as markers to evaluate the effects of a candidate drug or agent on a lymphocyte cell, particularly undergoing polarization. A candidate drug or agent can be screened for the ability to stimulate the transcription or expression of a given marker or markers (drug targets) or to down-regulate or inhibit the transcription or expression of a marker or markers. According to the present invention, one can also compare the specificity of a drug's effects by looking at the number of markers affected by the drug and comparing them to the number of markers affected by a different drug. A more specific drug will affect fewer transcriptional targets. Similar sets of markers identified for two drugs indicates a similarity in effect.

Some method are designed for identifying agents that modulate the levels, concentration or at least one activity of a protein(s) encoded by one or several genes in Table 2 or Table 6. Such methods or assays may utilize any means of monitoring or detecting the desired activity.

One specific embodiment of the invention is a method of identifying a compound capable of modulating the polarization of CD4+ lymphocytes, the method comprising:

(a) contacting the compound with naïve CD4+ lymphocytes;

(b) inducing the polarization of the lymphocytes;

(c) preparing a gene expression profile from the lymphocytes;

(d) comparing the lymphocyte gene expression profile to a gene expression profile derived from Table 1.

Preferably the induction of step (b) is performed by contacting the lymphocytes with a cytokine. Preferably the cytokine is IL-12 or IL-4. A difference in the expression profiles of the target genes identifies a potential drug compound for the treatment of asthma or other immune-mediated diseases. Another preferred embodiment of the invention is an identification method of the invention, wherein said gene expression profile derived from Table 1 is at least partly based on the expression fold changes of any one of the genes selected from the group consisting of: KIAA0053, LRRN3, CIG5, DUSP6, FER1L3, S100P, SATB1, SLC11A2, STK17B, a gene identified by accession number AI971169 and a gene identified by accession number AL432401.

Assays and screens can be used to identify compounds that are effective activators or inhibitors of target gene expression or activity. The assays and screens can be done by physical selection of molecules from libraries, and computer comparisons of digital models of compounds in molecular libraries and a digital model of the active site of the target gene product (i.e., protein).

The activators or inhibitors identified in the assays and screens may act by, but are not limited to, binding to a target gene product, binding to intracellular proteins that bind to a target gene product, compounds that interfere with the interaction between a target gene product and its substrates, compounds that modulate the activity of a target gene, or compounds that modulate the expression of a target gene or a target gene product.

Assays can also be used to identify molecules that bind to target gene regulatory sequences (e.g., promoter sequences), thus modulating gene expression. See, e.g., Platt (1994), J. Biol. Chem., 269:28558-28562.

Another specific embodiment of the invention is a method of identifying a compound that modulates the expression of at least one gene listed in Table 2 or Table 6. These methods involve:

(a) incubating a cell that can express a protein from the gene with a compound under conditions and for a time sufficient for the cell to express the protein of said gene, when the compound is not present;

(b) incubating a control cell under the same conditions and for the same time without the compound;

(c) measuring expression of the gene in the cell in the presence of the compound;

(d) measuring expression of the gene in the control cell; and (e) comparing the amount of expression of the gene in the presence and absence of the compound, wherein a difference in the level of expression indicates that the compound modulates the expression of the gene.

Another specific embodiment of the invention is a method of identifying a compound that modulates the activity of at least one gene listed in Table 2 or Table 6, the method comprising:

(a) incubating a cell that has said activity with a compound under conditions and for a time sufficient for the cell to express said activity, when the compound is not present;

(b) incubating a control cell under the same conditions and for the same time without the compound;

(c) measuring said activity in the cell in the presence of the compound;

(d) measuring said activity in the control cell; and (e) comparing the amount of said activity in the presence and absence of the compound, wherein a difference in the level of expression indicates that the compound modulates the activity of said gene.

In one preferred embodiment, the gene or genes is/are selected from the group consisting of: KIAA0053, LRRN3, CIG5, DUSP6, FER1L3, S100P, SATB1, SLC11A2, STK17B, a gene identified by accession number AI971169 and a gene identified by accession number AL432401.

Certain screening methods are performed with mouse lymphocytes. As an example, some methods involve identifying a compound capable of modulating the polarization of murine CD4+ lymphocytes. These methods comprise:

(a) contacting the compound with naïve murine CD4+ lymphocytes;

(b) inducing the polarization of the lymphocytes;

(c) preparing a gene expression profile from the lymphocytes; and (d) comparing the lymphocyte gene expression profile to a gene expression profile derived from Table 3.

This method can also be used for determining or confirming the activity of a compound in murine cells, when said compound is already identified in any one of the abovementioned human lymphocyte assay based identification methods as a modulator for polarization of human lymphocytes.

2. Methods for Detecting Differential Gene Expression

Assays to monitor the expression of a marker or markers as defined in Table 2 or Table 6 may utilize any available means of monitoring for changes in the expression level of the target genes. As used herein, an agent is said to modulate the expression of a target gene if it is capable of up- or down-regulating expression of the target gene in a lymphocyte cell during polarization. The protein products encoded by the genes identified herein can also be assayed to determine the amount of expression. Any method for specifically and quantitatively measuring a specific protein or mRNA or DNA product can be used. However, methods and assays of the invention typically utilize PCR or array or chip hybridization-based methods when seeking to detect the expression of a large number of genes.

The genes identified as being differentially expressed in lymphocytes may be used in a variety of nucleic acid detection assays to detect or quantify the expression level of a gene or multiple genes in a given sample. For example, traditional Northern blotting, dot blots, nuclease protection, RT-PCR, differential display methods, subtractive hybridization, and in situ hybridization may be used for detecting gene expression levels. Levels of mRNA expression may be monitored directly by hybridization of probes to the nucleic acids of the invention. Cell lines are exposed to an agent to be tested under appropriate conditions and time and total RNA or mRNA is isolated by standard procedures such those disclosed in Sambrook et al, Molecular Cloning—A Laboratory Manual, Cold Spring Harbor Laboratory Press, Cold Spring Harbor, N.Y. (1989).

One of skill in the art will appreciate that an enormous number of array designs are suitable for the practice of this invention. The high density array will typically include a number of probes that specifically hybridize to the sequences of interest. See WO 99/32660 for methods of producing probes for a given gene or genes. In addition, in a preferred embodiment, the array will include one or more control probes.

3. Exemplary Candidate Agents

Agents that are assayed in the above methods can be randomly selected or rationally selected or designed. As used herein, an agent is said to be randomly selected when the agent is chosen randomly without considering the specific sequences of the protein itself or those sequences involve din the interaction of the protein with its substrates or ligands, for instance. An example of randomly selected agents is a chemical library or a peptide combinatorial library, or a growth broth of an organism. As used herein, an agent is said to be rationally selected or designed when the agent is chosen on a nonrandom basis, taking into account the sequence of the target site and/or its conformation in connection with the agents action. Agents can be selected or designed by utilizing the peptide sequences that make up these sites. For example, a rationally selected peptide agent can be a peptide whose amino acid sequence is identical to or a derivative of any functional consensus site.

The agents of the present invention can be, as examples, peptides, small chemical molecules, vitamin derivatives, as well as carbohydrates, lipids, oligonucleotides and covalent and non-covalent combinations thereof. Dominant negative proteins, DNA encoding these proteins, antibodies to these proteins, peptide fragments of these proteins or mimics of these proteins may be introduced into cells. A "mimetic" as used herein refers to a protein having a modification of a region or several regions such that the protein mimetic has a structure chemically different from the parent peptide but topographically and functionally similar to the parent peptide. A skilled artisan can readily recognize that there is no limit as to the structural nature of the agents of the present invention.

Some compounds are peptides, including but not limited to, soluble peptides, including but not limited to members of random peptide libraries (see, e.g., Lam et al. (1991) Nature 354:82-84; Houghten et al. (1991) Nature 354:84-86,), and combinatorial chemistry-derived molecular libraries made of D-and/or L-amino acids, phosphopeptides (including, but not limited to, members of random or partially degenerate, directed phosphopeptide libraries; see, e.g., Songyang et al. (1993) Cell 72:767-778,), and small organic or inorganic molecules.

3. Computerized Analysis

Computer modeling or searching technologies can be used to identify compounds, or identify modified compounds that modulate or are candidates to modulate the expression or activity of a target gene product. For example, compounds likely to interact with the active site of the target gene product may be identified. The active site of target gene product can be identified using methods known in the art including, for example, analysis of the amino acid sequence of a molecule, and from a study of complexes formed by a target gene product with a native ligand. Chemical or X-ray crystallographic methods can be used to identify the active site of target gene product through the location of a bound ligand.

The three-dimensional structure of the active site can be determined. This can be done using known methods, including X-ray crystallography, which can be used to determine a complete molecular structure. Solid or liquid phase NMR can be used to determine certain intramolecular distances. Other methods of structural analysis can be used to determine partial or complete geometrical structures.

Computer-based numerical modeling can be used to complete an incomplete or insufficiently accurate structure. Modeling methods that can be used are, for example, parameterized models specific to particular biopolymers such as proteins or nucleic acids, molecular dynamics models based on computing molecular motions, statistical mechanics models based on thermal ensembles, or combined models. For most types of models, standard molecular force fields, representing the forces between constituent atoms and groups are necessary, and can be selected from force fields known in physical chemistry. Information on incomplete or less accurate structures determined in this way can be incorporated as constraints on the structures computed by these modeling methods.

Having determined the structure of the active site of a target gene product, either experimentally, by modeling, or by a combination of methods, additional candidate modulating compounds can be identified by searching databases containing compounds along with information on their molecular structure. The compounds identified in such a search are those that have structures that match the active site structure, fit into the active site, or interact with groups defining the active site. The compounds identified by the search are potential target gene product modulating compounds.

These methods may also be used to identify improved modulating compounds from an already known modulating compounds or ligands. The structure of the known compound is modified and effects are determined using experimental and computer modeling methods. The altered structure is compared to the active site structure of a target gene product to determine or predict how a particular modification to the ligand or modulating compound will affect its interaction with that protein. Systematic variations in composition, such as by varying side groups, can be evaluated to obtain modified modulating compounds or ligands of preferred specificity or activity.

Given the teachings herein, additional experimental and computer modeling methods useful to identify modulating compounds based on identification of the active sites of a target gene product and related transduction and transcription factors can be developed by those skilled in the art. Computer programs designed to screen and depict chemicals as well as molecular modeling systems are available from companies such as MSI (Molecular Simulations, Inc., San Diego, Calif., USA), Allelix, Inc. (Mississauga, Ontario, Canada), and Hypercube, Inc. (Gainesville, Fla., USA).

In addition to designing and generating compounds that alter binding, as described above, libraries of known compounds, including natural products, synthetic chemicals, and biologically active materials including peptides, can be screened for compounds that are inhibitors or activators.

Compounds identified by methods described above may be useful, for example, for elaborating the biological function of target gene products and in treatment of disorders in which target gene activity is deleterious.

C. Diagnostic Methods

Methods for assessing whether a subject has or is predisposed to obtain an immune-mediated disease (e.g. asthma, allergy or auto-immune disease) are also provided. These methods generally involve obtaining a sample from a subject having or suspected to have an immune-mediated disease. The expression levels for one or more the differentially expressed genes is then determined for the sample. The population of test cells is selected to include lymphocytic cells from the subject.

The expression level of the gene(s) is then compared with the expression level of the same gene(s) in a control sample. The status of the control sample with respect to presence or absence of an immune-mediated disease is known (e.g., the control sample is from an individual not suffering from the immune-related disease of interest or is from an individual having an immune-related disease). So, for example, if the control cell is representative of cells from a healthy individual, then similarity in expression level or expression profile between the test and control samples indicates that the subject does not have an immune-related disease. A difference in expression level or profile, in contrast, indicates that the subject from whom the test sample was derived has an immune-related disease.

If instead, the control sample is representative of cells from an individual that has a particular immune-related disease, then similarity in expression levels or expression profile means that the test cells are from a patient that has, or is susceptible to, the immune-related disease; whereas, a difference in expression levels or profile indicates that the subject does not have the immune-related disease.

D. Classifying Lymphocytes

Other methods that are provided are designed to classify a lymphocyte or to assess its cellular state. Such methods generally involve obtaining a test sample derived from a lymphocyte that is capable of expressing one or more nucleic acid markers from the group consisting of those listed in one or more of the tables (e.g., Table 1, or Table 2 or Table 6. The expression level for one or more of these markers is then determined. The expression level for these markers is compared with the expression levels of the same markers in a control sample. The control sample is derived from a lymphocytic cell whose cellular status is known (e.g., the cell is known to be a Th1 or Th2 cell). The lymphocytic cell from which the test sample is derived is then classified on the basis of this comparison.

For example, if the expression level or expression profile of the test sample is compared with expression levels or an expression profile from a Th1 cell, similarity in expression profile is an indication that the lymphocyte from which the test sample is derived is a Th1 cell. A difference, on the other hand, would be an indication that the sample is from a lymphocyte of another type or in another state (e.g., a Th2 cell).

VII. Treatment Methods

Methods of treating a patient with asthma or other immune-mediated diseases are also provided. These methods generally involve administering to the patient a pharmaceutical composition, wherein the composition alters the expression or activity of at least one gene listed in Table 2 or Table 6. In a preferred embodiment, the active compound of the pharmaceutical composition is identified by a screening method of the invention. In another preferred embodiment, the active compound of said pharmaceutical composition is an antibody binding to at least one gene product of the genes listed in Table 2 or Table 6.

Both therapeutic and prophylactic methods are provided. In therapeutic methods, a pharmaceutical composition is administered to a subject having or suspected to have an immune-related disease in an amount sufficient to alleviate one or more symptoms of the disease. In prophylactic methods, a pharmaceutical composition is administered to a subject susceptible to, or otherwise at risk for developing an immune-related disease, in an amount sufficient to reduce or arrest the development of the disease. The treatment can be administered in a single dose, but more commonly is administered in several doses.

If the immune-related disease, is a consequence of an excessive Th1 response, then certain methods involve administering an agent that inhibits the expression of a gene that is up-regulated during Th1 polarization or that inhibits the activity of the protein it encodes. Alternatively, an agent can be administered that activates the expression of a gene that is up-regulated in Tb2 cells, or which increases the activity of the protein encoded by such a gene. A third option is to administer one or more agents that achieve both of these results.

If instead the disease is associated with an excessive Th2 response, then some treatment strategies involve administering an agent that inhibits the expression or activity of a gene that is up-regulated in Th2 cells. Alternatively, an agent is administered that activates the expression or activity of a gene that is up-regulated in Th1 cells. Still other methods involve providing an agent or agents that accomplishes both of these results.

A number of methods that are known in the art can be utilized to modulate gene expression or activity. Various agents can be used to inhibit gene expression or the activity of the corresponding protein. Examples of such agents include antisense oligonucleotides, ribozymes, triple helix structure and double-stranded. RNA (dsRNA), particularly small-interfering RNAs (siRNAs). These agents are discussed in additional detail below. Alternatively, compounds that antagonize the activity of the protein encoded by the up-regulated genes can also be utilized. Examples include antibodies that specifically bind to the encoded protein. Other antagonists are small molecules.

Various options are also available for increasing gene expression or the activity of the protein encoded by a gene. One option is to administer a nucleic acid that encodes the protein whose activity one seeks to increase. This nucleic acid is operably linked to an appropriate expression control elements to facilitate its expression lymphocytes. Another option is to administer the protein itself, or an active fragment thereof Yet another option is to administer an agonist that increases the activity of the protein.

VIII. Compounds for Inhibiting or Enhancing the Synthesis or Activity of Control Genes A. Activity or Synthesis Inhibition As discussed above, expression of certain genes can cause or worsen the symptoms of an immune-related disease. The increase in the expression or activity of such control genes and their products can be countered using-various methodologies to inhibit their expression, synthesis or activity.

For example, antisense, ribozyme, triple helix molecules and antibodies can be utilized to ameliorate the negative effects of such control genes and gene products. Antisense RNA and DNA molecules act directly to block the translation of mRNA by hybridizing to targeted mRNA, thereby blocking protein translation. Hence, a useful target for antisense molecules is the translation initiation region. I Ribozymes are enzymatic RNA molecules that hybridize to specific sequences and then carry out a specific endonucleolytic cleavage reaction. Thus, for effective use, the ribozyme should include sequences that are complementary to the target mRNA, as well as the sequence necessary for carrying the cleavage reaction (see, e.g., U.S. Pat. No. 5,093,246).

Nucleic acids utilized to promote triple helix formation to inhibit transcription are single-stranded and composed of dideoxyribonucleotides. The base composition of such polynucleotides is designed to promote triple helix formation via Hoogsteen base pairing rules and typically require significant stretches of either pyrimidines or purines on one strand of a duplex.

Double stranded RNA (dsRNA) inhibition methods can also be use to inhibit expression of one or more of the differentially expressed nucleic acids. The RNA utilized in such methods is designed such that a least a region of the dsRNA is substantially identical to a region of a differentially expressed nucleic acid (e.g., a target gene); in some instances, the region is 100% identical to the target. For use in mammals, the dsRNA is typically about 19-30 nucleotides in length (i.e., small inhibitory RNAs are utilized (siRNA)). Methods and compositions useful for performing dsRNAi and siRNA are discussed, for example, in PCT Publications WO 98/53083; WO 99/32619; WO 99/53050; WO 00/44914; WO 01/36646; WO 01/75164; WO 02/44321; and published U.S. patent application Ser. No. 10/195,034, each of which is incorporated herein by reference in its entirety for all purposes.

Antibodies having binding specificity for a target gene protein that also interferes with the activity of the gene protein can also be utilized to inhibit gene protein activity. Such antibodies can be generated from full-length proteins or fragments thereof according to the methods described below.

B. Activity Enhancement

Immune-related diseases can be exacerbated by under-expression of certain control genes and/or by a reduction in activity of a control gene product, for example. Alternatively, the up-regulation of certain control gene products can produce a beneficial effect. In any of these scenarios, it is useful to increase the expression, synthesis or activity of such control genes and proteins.

These goals can be achieved, for example, by increasing the level of control gene product or the concentration of active gene product. In one approach, a control gene protein in the form of a pharmaceutical composition such as that described below is administered to a subject suffering from an immune-related disease. Alternatively, DNA sequences encoding control gene proteins can be administered to a patient at a concentration sufficient to treat a immune-related disease or to treat an individual at risk for such a disease. Gene therapy is yet another option and includes inserting one or more copies of a normal control gene, or a fragment thereof capable of producing a functional control protein, into lymphocytic cells using various vectors. Suitable vectors include, for example, adenovirus, adeno-associated virus and retrovirus vectors. Liposomes and other particles capable of introducing DNA into cells can also be utilized in some instances. Cells, typically autologous cells, that express a normal control gene can than be introduced or reintroduced into a patient to treat the immune-related disease.

X. Antibodies

Antibodies that are immunoreactive with polypeptides expressed from the differentially expressed genes or fragments thereof are also provided. The antibodies can be polyclonal antibodies, distinct monoclonal antibodies or pooled monoclonal antibodies with different epitopic specificities.

A. Production of Antibodies

The antibodies can be prepared using intact polypeptide or fragments containing antigenic determinants from proteins encoded by differentially expressed genes or target genes as the immunizing antigen. The polypeptide used to immunize an animal can be from natural sources, derived from translated cDNA, or prepared by chemical synthesis. In some instances the polypeptide is conjugated with a carrier protein. Commonly used carriers include keyhole limpet hemocyanin (KLH), thyroglobulin, bovine serum albumin (BSA), and tetanus toxoid. The coupled peptide is then used to immunize the animal (e.g., a mouse, a rat, or a rabbit). Various adjuvants can be utilized to increase the immunological. response, depending on the host species and include, but are not limited to, Freund's (complete and incomplete), mineral gels such as aluminum hydroxide, surface active substances such as lysolecithin, pluronic polyols, polyanions, peptides, oil emulsions, dinitrophenol and carrier proteins, as well as human adjuvants such as BCG (bacille Calnette-Guerin) and *Corynebacterium parvum.*

Monoclonal antibodies can be made from antigen-containing fragments of the protein by the hybridoma technique, for example, of Kohler and Milstein (Nature, 256:495-497, (1975); and U.S. Pat. No. 4,376,110, incorporated by reference in their entirety). See also, Harlow & Lane, *Antibodies, A Laboratory Manual* (C.S.H.P., NY, 1988), incorporated by reference in its entirety. The antibodies can be of any immunoglobulin class including IgG, IgM, IgE, IgA, IgD and any subclass thereof.

Techniques for generation of human monoclonal antibodies have also been described, including, for example, the human B-cell hybridoma technique (Kosbor et al., *Immunology Today* 4:72 (1983), incorporated by reference in its entirety); for a review, see also, Larrick et al., U.S. Pat. No. 5,001,065, (incorporated by reference in its entirety). An alternative approach is the generation of humanized antibodies by linking the complementarity-determining regions or CDR regions (see, e.g., Kabat et al., "Sequences of Proteins of Immunological Interest," U.S. Dept. of Health and Human Services, (1987); and Chothia et al., *J. Mol. Biol.* 196:901-917 (1987)) of non-human antibodies to human constant regions by recombinant DNA techniques. See Queen et al., *Proc. Natl. Acad. Sci. USA* 86:10029-10033 (1989) and WO 90/07861 (incorporated by reference in its entirety). Alternatively, one can isolate DNA sequences that encode a human monoclonal antibody or a binding fragment thereof by screening a DNA library from human B cells according to the general protocol set forth by Huse et al., *Science* 246:1275-1281 (1989) and then cloning and amplifying the sequences which encode the antibody (or binding fragment) of the desired specificity. The protocol described by Huse is rendered more efficient in combination with phage display technology. See, e.g., Dower et al., WO 91/17271 and McCafferty et al., WO 92/01047 (each of which is incorporated by reference). Phage display technology can also be used to mutagenize CDR regions of antibodies previously shown to have affinity for the peptides of the present invention. Antibodies having improved binding affinity are selected.

Techniques developed for the production of "chimeric antibodies" by splicing the genes from a mouse antibody molecule of appropriate antigen specificity together with genes from human antibody molecule of appropriate antigen specificity can be used. A chimeric antibody is a molecule in which different portions are derived from different species, such as those having a variable region derived from a murine monoclonal antibody and a human immunoglobulin constant region. Single chain antibodies specific for the differentially expressed gene products of the invention can be produced according to established methodologies (see, e.g., U.S. Pat. No. 4,946,778; Bird, *Science* 242:423-426 (1988); Huston et al., *Proc. Natl. Acad. Sci. USA* 85:5879-5883 (1988); and Ward et al., *Nature* 334:544-546 (1989), each of which is incorporated by reference in its entirety). Single chain antibodies are formed by linking the heavy and light chain fragments of the Fv region via an amino acid bridge, resulting in a single chain polypeptide.

Antibodies can be further purified, for example, by binding to and elution from a support to which the polypeptide or a peptide to which the antibodies were raised is bound. A variety of other techniques known in the art can also be used to purify polyclonal or monoclonal antibodies (see, e.g., Coligan, et al., Unit 9, *Current Protocols in Immunology*, Wiley Interscience, (1994), incorporated herein by reference in its entirety).

Anti-idiotype technology can also be utilized in some instances to produce monoclonal antibodies that mimic an epitope. For example, an anti-idiotypic monoclonal antibody made to a first monoclonal antibody will have a binding domain in the hypervariable region that is the "image" of the epitope bound by the first monoclonal antibody.

B. Use of Antibodies

The antibodies that are provided are useful, for example, in screening cDNA expression libraries and for identifying clones containing cDNA inserts which encode structurally-related, immunocrossreactive proteins. See, for example, Aruffo & Seed, *Proc. Natl. Acad. Sci. USA* 84:8573-8577 (1977) (incorporated by reference in its entirety). Antibodies are also useful to identify and/or purify immunocrossreactive proteins that are structurally related to native polypeptide or to fragments thereof used to generate the antibody. The antibodies can also be used to form antibody arrays to detect proteins expressed by the differentially expressed genes.

The antibodies can also be used in the detection of differentially expressed genes, such as control and fingerprint gene products. Various diagnostic assays can be utilized, including but not limited to, competitive binding assays, direct or indirect sandwich assays and immunoprecipitation assays (see, e.g., *Monoclonal Antibodies: A Manual of Techniques*, CRC Press, Inc. (1987) pp. 147-158). When utilized in diagnostic assays, the antibodies are typically labeled with a detectable moiety. The label can be any molecule capable of producing, either directly or indirectly, a detectable signal. Suitable labels include, for example, radioisotopes (e.g., $^3$H, $^{14}$C, $^{32}$P, $^{35}$S, $^{125}$I), fluorophores (e.g., fluorescein and rhodamine dyes and derivatives thereof), chromophores, chemiluminescent molecules, an enzyme substrate (including the enzymes luciferase, alkaline phosphatase, beta-galactosidase and horse radish peroxidase, for example). The antibodies can also be utilized in the development of antibody arrays.

As noted above, antibodies are useful in inhibiting the expression products of the differentially expressed genes and are valuable in inhibiting the action of certain control gene products (e.g., target gene products identified as causing or exacerbating tumor or cancer formation). Hence, the antibodies also find utility in a variety of therapeutic applications.

XI. Pharmaceutical Compositions

The invention provides also a pharmaceutical composition that can modulate the expression or activity of at least one gene listed in one or more of the tables (e.g. Table 2 or Table 6) for use in prophylaxis or treatment of asthma or other immune-mediated disease. In a preferred embodiment said pharmaceutical composition comprises an antibody binding to at least one genie product of the genes listed in Table 2 or Table 6 as an active ingredient.

A. Composition

The pharmaceutical compositions used for treatment of cancers and tumors comprise an active ingredient such as the inhibitory or activity-enhancing compounds such as described herein and, optionally, various other components.

Thus, for example, the compositions can also include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological-conditions, such as pH adjusting and buffering agents, toxicity adjusting agents, wetting agents, detergents and the like.

The composition can also include any of a variety of stabilizing agents, such as an antioxidant for example. When the pharmaceutical composition includes a polypeptide, the polypeptide can be complexed with various well known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include the production of sulfate, gluconate, citrate, phosphate and the like. The polypeptides of the composition can also be complexed with molecules that enhance their in vivo attributes. Such molecules include, for example, carbohydrates, polyamines, amino acids, other peptides, ions (e.g. sodium, potassium, calcium, magnesium, manganese), and lipids.

Further guidance regarding formulations that are suitable for various types of administration can be found in *Remington's Pharmaceutical Sciences*, Mace Publishing Company, Philadelphia, Pa., 17th ed. (1985). For a brief review of methods for drug delivery, see, Langer, *Science* 249:1527-1533 (1990).

B. Dosage

The pharmaceutical compositions can be administered for prophylactic and/or therapeutic treatments. The active ingredient in the pharmaceutical compositions typically is present in a therapeutic amount, which is an amount sufficient to slow or reverse tumor formation, to eliminate the tumor, or to remedy symptoms associated with the tumor or cancer. Toxicity and therapeutic efficacy of the active ingredient can be determined according to standard pharmaceutical procedures in cell cultures and/or experimental animals, including, for example, determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred.

The data obtained from cell culture and/or animal studies can be used in formulating a range of dosages for humans. The dosage of the active ingredient typically lines within a range of circulating concentrations that include the $ED_{50}$ with little or no toxicity. The dosage can vary within this range depending upon the dosage form employed and the route of administration utilized.

In prophylactic applications, compositions containing the compounds that are provided are administered to a patient susceptible to or otherwise at risk of tumor formation. Such an amount is defined to be a "prophylactically effective" amount or dose. In this use, the precise amount depends on the patient's state of health and weight Typically, the dose ranges from about 1 to 500 mg of purified protein per kilogram of body weight, with dosages of from about 5 to 100 mg per kilogram being more commonly utilized.

C. Administration

The active ingredient, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen.

Suitable formulations for rectal administration include, for example, suppositories, which consist of the packaged active ingredient with a suppository base. Suitable suppository bases include natural or synthetic triglycerides or paraffin hydrocarbons. In addition, it is also possible to use gelatin rectal capsules, which consist of a combination of the packaged nucleic acid with a base, including, for example, liquid triglycerides, polyethylene glycols, and paraffin hydrocarbons.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Formulations for injection can be presented in unit dosage form, e.g., in ampules or in multidose containers, with an added preservative. The compositions are formulated as sterile, substantially isotonic and in full compliance with all Good Manufacturing Practice (GMP) regulations of the U.S. Food and Drug Administration.

XII. Devices for Detecting Differentially Expressed Nucleic Acids

A. Customized Probe Arrays

1. Probes for Differentially Expressed Genes

The differentially expressed genes that are provided can be utilized to prepare custom probe arrays for use in screening and diagnostic applications. In general, such arrays include probes such as those described above in the section on differentially expressed nucleic acids, and thus include probes complementary to full-length differentially expressed nucleic acids (e.g. cDNA arrays) and shorter probes that are typically 10-30 nucleotides long (e.g., synthesized arrays). Typically, the arrays include probes capable of detecting a plurality of the differentially expressed genes of the invention. For example, such arrays generally include probes for detecting at least 2, 3, 4, 5, 6, 7, 8, 9 or 10 differentially expressed nucleic acids. For more complete analysis, the arrays can include probes for detecting at least 12, 14, 16, 18 or 20 differentially expressed nucleic acids. In still other instances, the arrays include probes for detecting at least 25, 30, 35, 40, 45 or all the differentially expressed nucleic acids that are identified herein.

2. Control Probes (a) Normalization Controls

Normalization control probes are typically perfectly complementary to one or more labeled reference polynucleotides that are added to the nucleic acid sample. The signals obtained from the normalization controls after hybridization provide a control for variations in hybridization conditions, label intensity, reading and analyzing efficiency and other factors that can cause the signal of a perfect hybridization to vary between arrays. Signals (e.g., fluorescence intensity) read from all other probes in the array can be divided by the signal (e.g., fluorescence intensity) from the control probes thereby normalizing the measurements.

Virtually any probe can serve as a normalization control. However, hybridization efficiency can vary with base composition and probe length. Normalization probes can be selected to reflect the average length of the other probes present in the array, however, they can also be selected to cover a range of lengths. The normalization control(s) can also be selected to reflect the (average) base composition of the other probes in the array. Normalization probes can be localized at any position in the array or at multiple positions throughout the array to control for spatial variation in hybridization efficiently.

(b) Mismatch Controls

Mismatch control probes can also be provided; such probes function as expression level controls or for normalization controls. Mismatch control probes are typically employed in customized arrays containing probes matched to known mRNA species. For example, certain arrays contain a mismatch probe corresponding to each match probe. The mismatch probe is the same as its corresponding match probe except for at least one position of mismatch. A mismatched base is a base selected so that it is not complementary to the corresponding base in the target sequence to which the probe can otherwise specifically hybridize. One or more mismatches are selected such that under appropriate hybridization conditions (e.g. stringent conditions) the test or control probe can be expected to hybridize with its target sequence, but the mismatch probe cannot hybridize (or can hybridize to a significantly lesser extent). Mismatch probes can contain a central mismatch. Thus, for example, where a probe is a 20 mer, a corresponding mismatch probe can have the identical sequence except for a single base mismatch (e.g., substituting a G, a C or a T for an A) at any of positions 6 through 14 (the central mismatch).

(c) Sample Preparation, Amplification, and Quantitation Controls

Arrays can also include sample preparation/amplification control probes. Such probes can be complementary to subsequences of control genes selected because they do not normally occur in the nucleic acids of the particular biological sample being assayed. Suitable sample preparation/amplification control probes can include, for example, probes to bacterial genes (e.g., Bio B) where the sample in question is a biologica sample from a eukaryote.

The RNA sample can then be spiked with a known amount of the nucleic acid to which the sample preparation/amplification control probe is complementary before processing. Quantification of the hybridization of the sample preparation/amplification control probe provides a measure of alteration in the abundance of the nucleic acids caused by processing steps. Quantitation controls are similar. Typically, such controls involve combining a control nucleic acid with the sample nucleic acid(s) in a known amount prior to hybridization. They are useful to provide a quantitative reference and permit determination of a standard curve for quantifying hybridization amounts (concentrations).

3. Array Synthesis

Nucleic acid arrays for use in the present invention can be prepared in two general ways. One approach involves binding DNA from genomic or cDNA libraries to some type of solid support, such as glass for example. (See, e.g., Meier-Ewart, et al., *Nature* 361:375-376 (1993); Nguyen, C. et al., *Genomics* 29:207-216 (1995); Zhao, N. et al, *Gene,* 158:207-213 (1995); Takahashi, N., et al., *Gene* 164:219-227 (1995); Schena, et al., *Science* 270:467-470 (1995); Southern et al., *Nature Genetics Supplement* 21:5-9 (1999); and Cheung, et al., *Nature Genetics Supplement* 21:15-19 (1999), each of which is incorporated herein in its entirety for all purposes.)

The second general approach involves the synthesis of nucleic acid probes. One method involves synthesis of the probes according to standard automated techniques and then post-synthetic attachment of the probes to a support. See for example, Beaucage, *Tetrahedron Lett.,* 22:1859-1862 (1981) and Needham-VanDevanter, et al., *Nucleic Acids Res.,* 12:6159-6168 (1984), each of which is incorporated herein by reference in its entirety. A second broad category is the so-called "spatially directed" polynucleotide synthesis approach. Methods falling within this category further include, by way of illustration and not limitation, light-directed polynucleotide synthesis, microlithography, application by ink jet, microchannel deposition to specific locations and sequestration by physical barriers.

Light-directed combinatorial methods for preparing nucleic acid probes are described in U.S. Pat. Nos. 5,143,854 and 5,424,186 and 5,744,305; PCT patent publication Nos. WO 90/15070 and 92/10092; EP 476,014; Fodor et al., *Science* 251:767-777 (1991); Fodor, et al., *Nature* 364:555-556 (1993); and Lipshutz, et al., *Nature Genetics Supplement* 21:20-24 (1999), each of which is incorporated herein by reference in its entirety. These methods entail the use of light to direct the synthesis of polynucleotide probes in high-density, miniaturized arrays. Algorithms for the design of masks to reduce the number of synthesis cycles are described by Hubbel et al., U.S. Pat. No. 5,571,639 and U.S. Pat. No. 5,593,839, and by, Fodor et al., *Science* 251:767-777 (1991), each of which is incorporated herein by reference in its entirety.

Other combinatorial methods that can be used to prepare arrays for use in the current invention include spotting reagents on the support using ink jet printers. See Pease et al., EP 728, 520, and Blanchard, et al. *Biosensors and Bioelectronics* II: 687-690 (1996), which are incorporated herein by reference in their entirety. Arrays can also be synthesized utilizing combinatorial chemistry by utilizing mechanically constrained flowpaths or microchannels to deliver monomers to cells of a support. See Winkler et al., EP 624,059; WO 93/09668; and U.S. Pat. No. 5,885,837, each of which is incorporated herein by reference in its entirety.

4. Array Supports

Supports can be made of any of a number of materials that are capable of supporting a plurality of probes and compatible with the stringency wash solutions, Examples of suitable materials include, for example, glass, silica, plastic, nylon or nitrocellulose. Supports are generally are rigid and have a planar surface. Supports typically have from 1-10,000,000 discrete spatially addressable regions, or cells. Supports having 10-1,000,000 or 100-100,000 or 1000-100,000 regions are common. The density of cells is typically at least 1000, 10,000, 100,000 or 1,000,000 regions within a square centimeter. Each cell includes at least one probe; more frequently, the various cells include multiple probes. In general each cell contains a single type of probe, at least to the degree of purity obtainable by synthesis methods, although in other instances some or all of the cells include different types of probes. Further description of array design is set forth in WO 95/11995, EP 717,113 and WO 97/29212, which are incorporated by reference in their entirety.

XIII. Kits

Kits containing components necessary to conduct the screening and diagnostic methods of the invention are also provided. Some kits typically include a plurality of probes that hybridize under stringent conditions to the different differentially expressed nucleic acids that are provided. Other kits include a plurality of different primer pairs, each pair selected to effectively prime the amplification of a different differentially expressed nucleic acid. In the case when the kit includes probes for use in quantitative RT-PCR, the probes can be labeled with the requisite donor and acceptor dyes, or these can be included in the kit as separate components for use in preparing labeled probes.

The kits can also include enzymes for conducting amplification reactions such as various polymerases (e.g., RT and Taq), as well as deoxynucleotides and buffers. Cells capable of expressing one or more of the differentially expressed nucleic acids of the invention can also be included in certain kits.

Typically, the different components of the kit are stored in separate containers. Instructions for use of the components to conduct an analysis are also generally included.

The following examples are offered to illustrate certain aspects of the methods and devices that are provided; it should be understood that these examples are not to be construed to limit the claimed invention.

EXAMPLES

A. Materials and Methods

Induction of Th1 and Th2 in Vitro Polarization

The mononuclear cells were isolated from the human cord blood of healthy neonates using Ficol Isolation Paque (Amersham Pharmacia Biotech, Uppsala, Sweden). The CD4+ cells were flrther purified using magnetic beads (Dynal, Oslo, Norway). The primary activation was performed using plate-bound αCD3 (500-1000 ng/μl for coating) and 500 ng/μl soluble αCD28 (Immunotech, Marseille, France). The cells were cultured in the density of 0.5-2×10⁶ cells/ml in Yssel's medium (Irvine Scientific, Santa Ana, Calif.) containing 1% AB-serum (Red Cross, Helsinki, Finland). The polarization of the cells was performed in either Th1 medium containing 2.5 ng/ml of IL-12 (R&D Systems, Minneapolis, Minn.) or in Th2 medium containing 10 ng/ml of IL-4 (R&D Systems) in the presence and absence of 3 ng/ml TGFβ (R&D Systems). Part of the cells was cultured in "neutral conditions" without any polarizing cytokines. Samples were collected at the time points of 0 h, 2 h, 6 h and 48 h.

Real-Time Quantitative RT-PCR

Real-time quantitative RT-PCR was performed to control the quality of the cell samples with different treatments. The gene expression levels were measured for the IFNγ, GATA-3, T-bet and housekeeping gene Elongation factor 1 alpha (EF1α), using TaqMan ABI Prism 7700 (TaqMan, ABI Prism 7700, Applied Biosystems, Foster City, Calif.) as described before (18). EF1α was used as a reference transcript. The expression of this housekeeping gene remains stable during the differentiation of Th1 and Th2 cells (19). Primers and probes (Table 4) used for the quantification of gene expression (MedProbe, Norway) were designed using Primer Express software (Applied Biosystems).

Oligonucleotide Array Studies

The total RNA of the samples was isolated using the Trizol method (Invitrogen Co., Carlsbad, Calif.) and was further purified with Qiagen's RNAeasy minikit (Qiagen, Valencia, Calif.). 4-5 μg of totRNA was used as starting material for the sample preparation. The sample preparation was performed according to the instructions and recommendations provided by the probe array manufacturer (Affymetrix). The samples were hybridized to HG-U95Av2 arrays containing probes for approximately 10,000 genes. The data was analyzed on three consecutive levels. At the detection level, each probe was assigned a call of present, absent, marginal, or no call. The comparison level analysis of the cells cultured defines a gene as upregulated if the signal log ratio between the reference and the target samples is larger than one (2-fold increase) and the target sample is present. Similarly, a gene is defined as downregulated if the signal log ratio is less than minus one (2-fold decrease) and the reference sample is present. At the third level of data analysis, genes that presented a consistent change in two separate experiments were considered as differentially expressed. The gene transcript levels were determined from data images with the algorithms in the GeneChip Microarray Suite™ software (Affymetrix MAS5), and the subsequent gene filtering and data analysis was done with Microsoft Excel 2002, Microsoft Access 2000 softwares.

Validation of the Oligonucleotide Array Results

For validation of the oligonucleotide array results with Real-Time RT-PCR, additional Th1 and Th2 primary cultures were generated as previously described (18). Briefly, the priming was performed in the presence of 100 ng/ml PHA (Murex Diagnostics, Chatillon, France) and irradiated CD32-B7 transfected fibroblasts (20). The feeder cells were added in the final density of 1×10⁶ cells/ml. Th1 cultures were supplemented with 2.5 ng/ml of IL-12 (R&D Systems, Minneapolis, Minn.). Th2 cultures were supplemented with 10 μg/ml of anti-IL-12 (R&D Systems) and 10 ng/ml of IL-4 (R&D Systems). After 48 hours of priming, 40 U/ml of IL-2 (R&D Systems) was added into the cultures to enhance the proliferation of the lymphocytes. Part of the cells were cultured without any polarizing cytokines in the presence of IL-2 alone. The cultures were generated from four individuals, and during polarization samples were collected at the time points 0 h, 6 h, 24 h, 48 h and 7 d.

Mice, Reagents and Cell Culture

Stat6 deficient mice and control wild-type Balb/cJ mice were from Jackson Laboratory (Bar Harbor, Me.). Splenic mononuclear cells were isolated with Ficoll-Paque PLUS (Amersham Pharmacia Biotech, Uppsala, Sweden). CD4⁺ T lymphocytes were further purified by magnetic CD4 Micro-Beads (Mitenyi Biotech, Bergisch Gladbach, Germany). The cells were activated with plate-bound anti-mouse CD3 (clone 500A2, 1.26 μg/ml, Pharmingen, San Diego, Calif.) and soluble anti-mouse CD28 (500 ng/ml; Pharmingen, San Diego, Calif.) and were cultured in IDME media containing 10% FCS, nonessential amino acids and 2-mercaptoethanol (all from Gibco BRL, Life Technologies, Paisley, Scotland). RmIL-4 (10 ng/ml, Pharmingen, San Diego, Calif.) and anti-IL-12, anti-IFN-γ (both are 10 g/ml, Pharmingen, San Diego, Calif.) were added for Th2 development. CD4+ T cells pooled from different mice were cultured as Th0 (with activation and anti-IL-4, anti-IL-12 and anti-IFN-γ) or Th2 differentiation. Cells were harvested at 0 h, 2 h, 6 h, 24 h and 48 h.

Oligonucleotide Microarray Analysis

Total RNA was extracted by Trizol (Gibco BRL, Life Technologies, Paisley, Scotland) and further purified with RNeasy Kit (Qiagen, Valencia, Calif.). cDNA was synthesized by Superscript II kit (Gibco BRL, Life Technologies, Paisley, Scotland) using T7-(dT)$_{24}$ as primer. Biotin-labelled cRNA was prepared by in vitro taanscription reaction using BioArray High Yield RNA Transcript Labelling Kit (Enzo Diagnostics, Inc. Farmingdale, N.Y.) based on manufacture's protocol. The cRNA was purified, fragmented and hybridized to Affymetrix MG-U74A Genechips™. Arrays were stained and scanned according to Affymetrix (Santa Clara, Calif.) protocols.

Affymetrix Microarray Suit™ (version 5.0) software was used for the data analysis. In this program, Signal Log Ratio is used to describe the change between a target and reference array. The change is expressed as $\log_2$ ratio. Therefore, $\log_2$ ratio (Signal Log Ratio) of 1 equal to a two-fold change. In this study, the probe sets were excluded if: 1), the detection for both target and reference is Absent, 2) in comparison analysis, if the Change call gives NC (No Change) and 3), the signal log ratio between target and reference is between −1 and 1. Since there are five independent cell cultures to study IL4 inducible genes at 48 h, t-test was also used to compare the signals between target (Activation+IL4) and reference (Activation) groups. And then 0.05 was set as the cutoff for p-value.

Real Time Quantitative Pcr (TaqMan®) Detection

The principle of TaqMan® detection has been described previously. Primers and probes for TaqMan® detection were designed by Primer Express™ software (Applied Biosystems, Foster City, Calif.) and made by MedProbe (Oslo, Norway). The sequences for the primers and probes are listed in Table 5. Samples from three independent cultures were measured in duplicate in two separate runs. The standard deviation from these values must be less than the 0.5. $C_T$ value, which means the number of PCR cycles required for the detection of fluorescence signal to exceed a fixed threshold. The relative expressions of target mRNA were normalized against EF1α:

$$\Delta C_T = C_T(EF1\alpha) - C_T(\text{target})$$

$$\Delta\Delta C_T = \Delta C_{T1} - \Delta C_{T2}$$

Where $\Delta C_{T2}$ represents $\Delta C_T$ from not treated (time point 0 h) Stat6+/+ and Stat6 −/−CD4⁺ T cells and $\Delta C_{T1}$ represents $\Delta C_T$ from other time points. With this calculation, basically $\Delta\Delta C_T$ equals to $\log_2$ ratio, therefore $\Delta\Delta C_T 1 = 2$ fold changes. The experiments were performed using an ABI PRISM 7700 Sequence Detection System (Applied Biosystems).

Immunofluorescence Staining and Facs Analysis

CD4+ T cells from Stat6+/+ and Stat6−/− mice were activated and cultured for Th2 priming. At 48 h, samples were collected and stained. Briefly, cells were washed with PBS and then stained with FITC-conjugated rat anti-mouse Ly-6A/E monoclonal antibody (BD Biosystem, San Diego, Calif.) or isotype control antibody at 4° C. for 20 min. Cells were washed twice and then analysed by FACScan with CellQuest software. At least 10000 cells were analysed for each sample.

B. Results

In order to elucidate the genes involved in the early polarization and to explore the inhibitory mechanism of TGFβ on the differentiation of Th1 and Th2 cells, we studied the gene expression profiles of the CD4+ cells induced to Th1 and Th2 directions in the absence and presence of TGFβ. First, the differential expression of known Th1 and Th2 marker genes IFNγ, T-bet and GATA-3 was studied in the 48-hour samples to ensure that the cells had been induced to differentiate to Th1 and Th2 directions (FIG. 1) (13, 16). After that the samples were hybridized on HG-U95Av2 arrays representing probes for approximately 10,000 mainly known human genes. According to oligonucleotide array results, activation via CD3/CD28 alone induced expression of 437 probe sets and repressed 361 probesets at 2-hour time point (data not shown). After 6 hours expression of 832 probe sets was upregulated, whereas 856 probes sets were downregulated in response to CD3/CD28-activation (data not shown). After 48 hours, 582 probe sets become induced and 533 probes sets were repressed by CD3/CD28-activation compared to the Thp cells (FIG. 2A). In the figure only the genes showing 16-fold change in comparison between activated and Thp cells are presented. In addition to genes regulated by activation, numerous targets with various functions were identified as being regulated by the cytokines IL-12, IL-4 and TGFβ (see Tables 1 and 2).

Targets of IL-12 and IL-4

The effects of IL-12 were modest during the immediate phase (2 and 6 hours) of polarization as over 2-fold changes were seen in expression of only 3 genes (Table 1). All of these were classified to be "not changed" by the MAS5 algorithm and thus might be not reliable changes. After 48-hours the effects of IL-12 become clear as 23 genes become regulated by IL-12 (FIG. 2B). Altogether 40 genes were detected to be differentially expressed by the cells induced to differentiate to Th1 or Th2 directions for 48 hours (table 1 and FIG. 2F). Previously reported "marker genes" IFNG, IL-2, L18RAP, CTLA1/GZMB, G0S2, ANXA3, P2RX5, LIF and BLR1 were preferentially expressed by the cells induced to polarize to the Th1 direction (21-23) and MAF/C-MAF, GATA-3, EBI2, IL10RA, Cox-2, NTRK1, CXCR4, E4BP4/NFIL3 and IL-13 were confirmed to be preferentially expressed by the cells induced to the Th2 direction (15, 16, 21, 22, 24-26). Moreover, suppressor of cytokine signaling 1 (TIP3/SOCS-1) was significantly more expressed by the cells polarized to the Th2 direction compared to those induced to the Th1 direction.

The effects of IL-4 were clear already after 2 hours of Th2 polarization when 34 genes become regulated by IL-4 compared to the CD3/CD28-activation (Table 1). After 6 hours, 38 genes were detected to be regulated by IL-4. After 48 hours IL4 regulated expression of 41 genes (Table I and FIG. 2C). These genes included both known and unknown IL-12 and IL-4 regulated genes. To our knowledge, regulation of the genes PACE, MRF-1, FLOT1, MTMR1, GOSR2, AF055029, AL050166, AF070528, SCYC2 by IL-12 and genes KIAA1013, ID2, KIAA0750, STK17B, HMGCS1, AL049940, AUH, BCL2A1 and HIC by IL-4 has not been previously described.

Regulation of Gene Expression by TGFβ

TGFβ regulated expression of numerous genes after 2 or 6 hours in Th1 or Th2 in polarizing conditions (Table I). However, only few of these genes (1D3, CCL20, RTP801, LAMA3, R32184_3) were also regulated by IL-4 or IL-12. After 48 hours the antagonizing effects of TGFβ on the genes regulated by IL-12 or IL-4 become more evident. The presence of TGFβ in Th1 conditions induced the expression of 16 genes and repressed expression of 6 genes (see Table I and FIG. 2D). These TGFβ target genes included specific targets of TGFβ, but also genes regulated by IL-12 or IL-4. TGFβ antagonized the effects of IL-12 by upregulating expression of TNFRSF9 and by repressing expression of GZMB/CTLA-1, a gene induced by both IL-12 and IL4. Interestingly, in Th1 conditions TGFβ also downregulated the expression of IL-4-inducible genes NFIL3/E4BP4 and SATB1 and induced expression of VIM, which was preferentially expressed by the cells cultured in Th2 conditions when compared to those cultured in Th1 conditions.

In Th2 conditions TGFβ induced expression of 16 genes and repressed 15 genes (see Table I and FIG. 2E). Again TGFβ regulated a specific set of its own targets, but importantly it antagonized the effects of IL-4 by repressing a set of IL-4-inducible genes (ID2, Cox-2, PLA2G4A, BCL2A1, NFIL3) and expression of GNAI1, which was preferentially expressed in the cells cultured in Th2 conditions when compared to Th1 conditions.

Validation of a Set of Genes Using Real-Time RT-PCR

Oligonucleotide array results were obtained from two independent experiments.

Four of the genes (SATB1, DUSP6, E4BP4 and TIP3) identified to be differentially expressed by the cells cultured in Th1 and Th2 conditions were selected for TaqMan RT-PCR analysis to further validate the results obtained with oligonucleotide arrays and to follow the expression kinetics of this set of interesting genes in Th1 and Th2 conditions during the one week of polarization from Thp cells. The results obtained with Real-Time RT-PCR were concordant with the oligonucleotide array data (FIG. 3). Importantly, NFIL3/E4BP4, TLP3/SOCS-1 and DUSP6 were identified to be differentially expressed in the cells cultured in Th1 and Th2 conditions already after six hours of polarization and the differences were maintained for at least the two first days of polarization. Also SATB1 was differentially expressed after six hours in three of four individuals studied, and in all individuals after one and two days of polarization. DUSP6 is expressed as two alternative splicing variants, and thus expression of both forms was quantitated. According to the results, only the long form is expressed by the cells studied. Also the expression of gene GADD45β was verified with RT-PCR based on the data analysis with the previous version of the Affymetrix analysis program, MAS4™, which found the gene to be preferentially expressed by the cells cultured in Th1 conditions compared to Th2 conditions as described before (27, 28). However, after reanalysis of the data with the updated MAS5 program, GADD45β was excluded from the results, and therefore, not presented in the FIG. 2. The RT-PCR analysis confirmed the differences in the expression of GADD45β in the cells cultured in Th1 or Th2 conditions.

IL4 Inducible Genes in Murine CD4+ T Lymphocytes

To identify IL4 inducible genes in murine CD4+ lymphocytes, CD4+ T cells were isolated from Stat6+/+ mice (Balb/cJ mice) and were activated with plate-bound anti-CD3 and soluble anti-CD28. IL4, anti-IL12 and anti-IFNγ were added for Th2 development. By comparing microarray data from Th2 (IL4+activation) vs. Th0 (activation alone) at 48 h, IL-4 inducible genes were identified. From 5 independent cell cultures, 117 probe sets (116 known genes) were regulated by IL4, 26 of 117 were up-regulated and 91 of them were down-regulated (Table 3). The differentially expressed genes were divided to 6 groups: immune response and related, transcription regulation and DNA binding, enzymes and inhibitors, apoptosis and cell proliferation, cell surface and structure proteins and miscellaneous.

Stat6 Regulated Murine Genes

As T cells from Stat6−/− mice have the deficiency for Th2 development, we isolated both Stat6−/− and Stat6+/+ CD4+ T cells, activated and cultured them for Th2 polarization. At 48 h, cells were harvested; RNA was isolated and subjected to DNA microarray analysis. Stat6 target genes were identified by comparing DNA microarray data obtained from Stat6−/− Th2 (IL4+activation) cells to data obtained from Stat6+/+ Th2 (IL4+activation) cells. 37 probe sets (36 known genes) were differentially expressed. 17 (including Stat6) of 37 probe sets were down-regulated and 20 probe sets were downregulated in Stat6 deficient cells as compared to the wild type cells (Table 3). Within these genes, 20 are induced by IL4, including the known Stat6 target genes, IL4 and Gata3 ... Hipk2 and Nfil3 have been shown to be Stat6 target genes also in B cells (29). Stat6 is able to compete with Stat1 for its binding to the IFNγ promoter and inhibit its expression (30, 31, 32). Therefore, it makes sense that a number of IFN regulated genes, such as Ifi205, Ifi203, Isg15 and Isg20, were up-regulated in Stat6−/− CD4+ T cells. Expression of certain genes known to be expressed mainly in Th1 cells or induced by IFNγ, including Il18r1, CCR5, Gzmb, Ly6a, and Txk, was inhibited by Stat6.

20 of 37 known Stat6 target genes are induced by IL4, whereas 20 of 117 IL4 inducible genes are regulated via Stat6 (Table 3). Because there are other signal pathways involved in IL4 signalling (33), it is evident that not all the IL-4 inducible genes are regulated by Stat6. Besides the 20 IL-4 inducible and Stat6 regulatory genes, there were 17 Stat6 regulated genes that are not induced by IL4.

Kinetic Study of IL4 Inducible and Stat6 Regulated Genes in Mice

In order to elucidate the molecular mechanisms for T cell differentiation at very early stage and also to follow the early changes for those IL4 and Stat6 regulated genes identified at 48 h, the kinetics of gene expression profiles at early T cell polarization were studied by using oligonucleotide arrays (Affymetrix). At early time points (2 h and 6 h), a group of novel IL4 inducible genes were identified, including Bcl2, Atf3, Pole2, Cish and Crabp2. Il4ra and Pros1, two known IL4 inducible genes, were induced by IL4 already at early time points. FIG. 1 was induced by IL4 at 2 h and remained upregulated at 24 h.

Interestingly, there were more genes induced by IL4 at early time points; on the contrary, there were more genes suppressed by IL4 at 48 h. Most Th1 marker genes or interferon inducible genes, such as Il18r1, Ifi203, Ifi204, Ifi205, Ifng, Ifit1, became differentially expressed at 24 h or 48 h.
[0002] The kinetic study, revealed a group of early Stat6 regulated genes, such as Pole2, Ppp3cc, Fig1, Pros1, Casp6, Il4ra and IL4. All of these genes were also IL4 inducible genes. At 24 h and 48 h, Myo6, Cmkbr8 (CCR8), Crabp2, Hipk2, Atf3, Nfil3, Zfp118 were identified as Stat6 regulated genes The novel IL4 inducible or Stat6 target genes in murine cells identified in this study are summarized in Table 6.

Taqman and FACS Analysis Confirms the Microarray Results

To verify the findings from microarray data, selected genes were further studied by real-time quantitative RT-PCR. Based on microarray results, Hipk2, Nfil3, Zfp118 and Atf3 are induced by IL4 and are regulated by Stat6. Expression of Ifi203 is inhibited by IK4 via Stat6. Expression of these genes was measured using real-time PCR during the first two days of CD4+ T cell differentiation using samples from three independent cell cultures. In Stat6+/+ CD4+ T cells the expression of Hipk2 was induced by IL4 quickly (2h) and the difference in Hipk2 expression between Th1 and Th2 cells further increased at 24 h and 48 h. Hipk2 expression was lower in Stat6-deficient cells compared to wild type cells at all the time points. Similar results were obtained for Nfil3 and Zfp118. Atf3 was induced by IL4 already at 2 h. In Stat6−/− CD4+ T cells, the expression level of Atf3 in Th2 condition was lower than in Stat6+/+ T cells. In contrast, the expression of Ifi203 was inhibited by IL4. When Stat6 is deficient, especially at 48 h, its expression level was increased and the biggest difference was seen quite late (48 h). We consider that Ifi203 could be a secondary target of Stat6. Together, these results show that these genes were induced or repressed by IL4 through Stat6.

The Ly-6 family of cell surface molecules has previously been shown to participate in T cell activation. The expression of Ly-6A/E is upregulated on normal murine T and B cells by IFN-gamma. The protein expression of Ly6a at 48 h polarized Th2 cells was measured by FACScan using FITC-conjugated rat anti-mouse Ly-6A/E monoclonal antibody. As expected based on microarray results, at 48 h the protein expression of Ly6a was upregulated (90%) in Stat6−/− cells cultured in Th2 conditions compared to wild type cells (45%) cultured equally.

C. Discussion

Our study demonstrates that triggering of the T cell receptor leads to regulation of more than 1000 genes with various functions. Compared to that number, the group of target genes regulated by cytokines mediating the differentiation process is specific and limited to only less than 100 genes, at least at this stage of differentiation.

Comparison of the cells cultured in Th1 or Th2 conditions to each other or to CD3/CD28-activated cells revealed changes in the expression of 124 genes. Of these genes approximately 77 have not been previously associated with Th1 and Th2 polarization. Differential regulation of genes DUSP6, E4BP4/NFIL3, SATB1 and TIP3/SOCS-1 was further confirmed using Real-Time RT-PCR. Preferential induction of these genes by IL-4 already after 2 hours of Th2 polarization positions these genes as important candidates as upstream regulators of the early differentiation process. The roles of these genes in Th1 and Th2 differentiation are currently unknown. DUSP6 is a phosphatase, which inhibits activity of ERK2 (35). E4BP4/NFIL3 is an inducer or repressor of transcription, which can activate IL-3 expressions, and a binding site for this factor is also present in the promoter area of IFNγ. In pro-B lymphocytes E4BP4/NFIL3 has been found to participate in preventing apoptosis in response to IL-3 through ras-mediated signaling, which involves activation of both PI3K and raf/MAPK pathways (36, 37). SATB1 is a DNA binding protein, which is known to be involved in the development of thymic T cells (38). Its cleavage by Caspase-6 and resulting dissociation from chromatin is involved in nuclear degradation occurring during early apoptosis of T cells (39). TIP3/SOCS-1 induced by cytokine/STAT pathway is an inhibitor of cytokine signaling. Previous reports have provided controversial information concerning the role of TIP3/SOCS-1 in Th1 and Th2 cells; on one hand the protein has been shown to be preferentially expressed by the Th1 cells in mouse (40). On the other hand, it has been reported that TIP3/SOCS-1 is induced by IL-6 in human, which promotes the Th2 and inhibits the Th1 commitment (40, 41). DUSP6, SATB1, E4BP4/NFIL3 and TIP3/SOCS-1 are likely to be among those upstream factors that respond first to the polarizing signals and thus are involved in determining the fate of Thp cells during the early stages of polarization.

It has been previously shown that TGFβ inhibits the differentiation of Th1 and Th2 subtypes (42, 43). Studies with mice have shown that the inhibition of Th1 and Th2 differentiation by TGFβ occurs through suppressing T-bet and GATA-3 expression, respectively (44-46). In our study with human cells these two genes were not among the numerous primary genes regulated by TGFβ indicating that the mechanism of TGFβ regulation on Th1 and Th2 responses is probably more complex than has been previously thought. The effects of TGFβ can also vary depending on the stage of cell differentiation, cytokine environment and concentration of TGFβ used in the cultures (47).

Enhanced Th2 response is known to contribute to the phenotype and symptoms of asthma (1-2). On the other hand, recent studies with mouse models have demonstrated that TGFβ1 can suppress the airway hyper-responsiveness and airway inflammation associated with asthma (48, 49). However, the molecular mechanism of this suppression is not known. One hypothesis could be that TGFβ is able to inhibit pathogenesis of asthma through its ability to suppress Th2 responses. If this hypothesis is correct, the genes which are regulated by TGFβ to suppress the Th2 development are particularly interesting. Our results demonstrate that TGFβ regulates a set of the same target genes as IL-12 and IL-4 (ID3, CCL20, RTP801, LAMA3, R32184_3, TNFSF9, E4BP4, CTLA1/GZMB, ID2, Cox-2, GNAI1, PLA2G4A, BCL2A1). Interestingly, most of these genes coregulated by IL-12/IL-4 and TGFβ are known to participate in the signaling events involved in apoptosis or survival. The IL-12 or IL-4 antagonizing influence of TGFβ on the expression of these genes could partly explain the inhibitory effect of TGFβ on differentiation. If regulation of the expression of these genes can regulate the differentiation process, they might be critical factors for the polarization.

In addition to genes regulated by IL-12 and IL-4, TGFβ also regulated many other interesting targets such as DUSP4, IL-9, IL1RN and LGAL3. DUSP4, which is known to inhibit ERK1/2, JNK1/2 and c-jun activity, was upregulated by TGFβ in Th1 conditions (50-51). JNK1 and JNK2 have been associated with Th1 and Th2 differentiation (52-53). Studies with knockout mice have demonstrated that in the absence of JNK1, the differentiation of Th1 and Th2 subsets is impaired and the cells preferentially polarize to Th2 subtypes. JNK2 seemed to be required for proper Th1 differentiation. Inhibition of JNK2 activity through DUSP4, could provide one possible mechanism responsible for inhibiting Th1 differentiation by TGFβ. Interestingly, in Th2 conditions TGFβ induced expression of certain genes that have been previously connected to asthma and other inflammatory diseases. These genes included such as IL1RN, IL-9 and LGAL3. IL1RN is known to inhibit the IL-1 signaling by binding to IL1R, which according to our results is upregulated by IL4. Polymorphisms in the IL1RN gene have been associated with various inflammatory diseases, such as asthma and diabetes (54, 55). IL-9 is a Th2-type cytokine and a candidate gene for asthma (56). It is involved in induction of many symptoms associated with asthma and has been considered as a potential target for asthma therapy (57). LGAL3 is involved in downregulation of Th2 cytokine IL-5 and it has been used to repress the symptoms of asthma in rat models (58, 59). Taken together, in addition to antagonizing the effects of IL-12 and IL4, in Th2 conditions TGFβ regulates expression of various genes involved in inflammatory diseases. These genes are likely to play an important role in maintaining the balance between Th1 and Th2 responses.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes to the same extent as if each individual publication, patent or patent application were specifically and individually indicated to be so incorporated by reference.

TABLE 1

| TIME | AFFY PROBE ID | GENE NAME | SYMBOL | ACCESSION | FOLD CHANGE |
|---|---|---|---|---|---|
| | Target genes of IL-12 in human CD4+ T cells (Th1-induced vs activated) |||||
| 2 h | 32417_at | desmocollin 3 | DSC3 | D17427 | 2.8* |
|  | 37194_at | GATA binding protein 2 | GATA2 | M68891 | 2.1* |
|  | 39718_r_at | mitochondrial ribosomal protein L33 | MRPL33 | N98607 | -4.0* |
|  | 32907_at | 5-hydroxytryptamine (serotonin) receptor 6 | HTR6 | L41147 | -2.5* |
| 6 h | 40702_at | interferon, gamma | IFNG | X13274 | 113.4 |
|  | 1021_at | interferon, gamma | IFNG | J00219 | 35.0 |
| 48 h | 1611_s_at | interferon, gamma | IFNG | J00219 | 28.1 |
|  | 33093_at | interleukin 18 receptor accessory protein | IL18RAP | AF077346 | 12.0 |
|  | 37137_at | granzyme B (granzyme 2, cytotoxic T-lymphocyte-associated serine esterase 1) | GZMB | M17016 | 11.4 |
|  | 32370_at | cytotoxic T-lymphocyte-associated serine esterase 1 | CTLA1 | M57888 | 5.6 |
|  | 35338_at | paired basic amino acid cleaving enzyme (furin, membrane associated receptor protein) | PACE | X17094 | 3.9 |
|  | 38326_at | putative lymphocyte G0/G1 switch gene | G0S2 | M69199 | 3.4 |
|  | 38278_at | modulator recognition factor I | MRF-1 | M62324 | 3.4 |
|  | 33305_at | serine (or cysteine) proteinase inhibitor, clade B (ovalbumin), member 1 | SERPINB1 | M93056 | 3.2 |
|  | 1004_at | Burkitt lymphoma receptor 1, GTP-binding protein | BLR1 | X68149 | 2.6 |
|  | 36776_at | lymphocyte-activation gene 3 | LAG3 | X51985 | 2.6 |
|  | 40635_at | flotillin 1 | FLOT1 | AF089750 | 2.5 |
|  | 1534_at | interleukin 12 receptor, beta 2 | IL12RB2 | U64198 | 2.3 |
|  | 33513_at | signaling lymphocytic activation molecule | SLAM | U33017 | 2.2 |
|  | 34654_at | myotubularin related protein 1 | MTMR1 | AJ224979 | 2.1 |
|  | 38620_at | golgi SNAP receptor complex member 2 | GOSR2 | AA905543 | -2.3* |
|  | 37623_at | nuclear receptor subfamily 4, group A, member 2 | NR4A2 | X75918 | -2.5 |
|  | 34866_at |  |  | AF055029 | -2.8 |
|  | 31856_at | glycoprotein A repetitions predominant | GARP | Z24680 | -2.8 |
|  | 39582_at |  |  | AL050166 | -2.9* |
|  | 38575_at |  | MALT1 | AF070528 | -3.0* |
|  | 31496_g_at | small inducible cytokine subfamily C, member 2 | SCYC2 | D63789 | -3.1 |
|  | 33541_s_at | leukocyte-associated Ig-like receptor 2 | LAIR2 | AA133246 | -3.4 |
|  | 31540_at | Tumor necrosis factor receptor superfamily, member 9 | TNFRSF9 | U03397 | -3.5 |
| | Target genes of IL-4 in human CD4+ T cells (TH2-induced vs activated) |||||
| TIME | AFFY PROBE ID | GENE NAME | SYMBOL | ACCESSION | FOLD CHANGE |
| 2 h | 38549_at | vipirin | cig5 | AF026941 | 13.5 |
|  | 35659_at | interleukin 10 receptor, alpha | IL10RA | U00672 | 6.5 |
|  | 974_at | mitogen-activated protein kinase kinase kinase 14 | MAP3K14 | Y10256 | 5.1 |
|  | 34757_at | ADP-ribosyltransferase (NAD+; poly(ADP-ribose) polymerase)-like 2 | ADPRTL2 | AA595596 | 4.6* |
|  | 1062_g_at | interleukin 10 receptor, alpha | IL10RA | U00672 | 4.1 |
|  | 37544_at | nuclear factor, interleukin 3 regulated | NFIL3 | X64318 | 4.0 |
|  | 41193_at | dual specificity phosphatase 6 | DUSP6 | AB013382 | 4.0 |

TABLE 1-continued

| | | | | |
|---|---|---|---|---|
| 39593_at | Homo sapiens, Similar to fibrinogen-like 2, clone MGC:22391 IMAGE: 4616866, mRNA, complete cds | | AI432401 | 3.9 |
| 587_at | endothelial differentiation, sphingolipid G-protein-coupled receptor, 1 | EDG1 | M31210 | 3.4 |
| 38149_at | KIAA0053 gene product | KIAA0053 | D29642 | 3.2 |
| 1816_at | RAS p21 protein activator 2 | RASA2 | D78156 | 3.2 |
| 41592_at | JAK binding protein | SSI-1 | AB000734 | 3.2 |
| 35712_at | leucine-rich repeat protein, neuronal 3 | LRRN3 | AC004142 | 3.0 |
| 41384_at | receptor-interacting serine-threonine kinase 2 | RIPK2 | AF117829 | 2.9 |
| 33047_at | ESTs, Weakly similar to B34087 hypothetical protein [H. sapiens] | | AI971169 | 2.9 |
| 33809_at | guanine nucleotide binding protein (G protein), alpha inhibiting activity polypeptide 1 | GNAI1 | AL049933 | 2.8 |
| 38051_at | mal, T-cell differentiation protein | MAL | X76220 | 2.7 |
| 828_at | prostaglandin E receptor 2 (subtype EP2), 53 kD | PTGER2 | U19487 | 2.7 |
| 40456_at | up-regulated by BCG-CWS | LOC64116 | AL049963 | 2.7 |
| 1061_at | interleukin 10 receptor, alpha | IL10RA | U00672 | 2.6 |
| 33291_at | RAS guanyl releasing protein 1 (calcium and DAG-regulated) | RASGRP1 | AF081195 | 2.6 |
| 36736_f_at | phosphoserine phosphatase | PSPH | Y10275 | 2.5* |
| 37889_at | CD47 antigen (Rh-related antigen, integrin-associated signal transducer) | CD47 | AA535376 | 2.4* |
| 33260_at | son of sevenless homolog 1 (Drosophila) | SOS1 | L13857 | 2.3 |
| 35320_at | solute carrier family 11 (proton-coupled divalent metal ion transporters), member 2 | SLC11A2 | AB004857 | 2.3 |
| 36899_at | special AT-rich sequence binding protein 1 (binds to nuclear matrix/scaffold-associating DNAs) | SATB1 | M97287 | 2.3 |
| 725_i_at | Chorionic Somatomammotropin Hormone Cs-5 | | HG1751-HT1768 | 2.3* |
| 40511_at | GATA binding protein 3 | GATA3 | X58072 | 2.3 |
| 34822_at | tumor protein p53 binding protein, 2 | TP53BP2 | U58334 | 2.1 |
| 41145_at | KIAA0914 gene product | KIAA0914 | AB020721 | 2.1* |
| 1860_at | v-maf musculoaponeurotic fibrosarcoma oncogene homolog (avian) | MAF | AF055376 | 2.1 |
| 649_s_at | tumor protein p53 binding protein, 2 | TP53BP2 | U58334 | 2.0 |
| 39827_at | chemokine (C—X—C motif), receptor 4 (fusin) | CXCR4 | L06797 | 2.0 |
| 41475_at | HIF-1 responsive RTP801 | RTP801 | AA522530 | -2.1 |
| 33997_at | ninjurin 1 | NINJ1 | U91512 | -2.3 |
| 37043_at | Homo sapiens mRNA; cDNA DKFZp586B1722 (from clone DKFZp586B1722) | | AL049449 | -2.8* |
| 1062_g_at | inhibitor of DNA binding 3, dominant negative helix-loop-helix protein | ID3 | AL021154 | -2.8 |
| 41193_at | interleukin 10 receptor, alpha | IL10RA | U00672 | 12.6 |
| 38549_at | dual specificity phosphatase 6 | DUSP6 | AB013382 | 8.6 |
| 41592_at | viperin | cig5 | AF026941 | 7.7 |
| 34348_at | JAK binding protein | SSI-1 | AB000734 | 7.5 |
| 40511_at | serine protease inhibitor, Kunitz type, 2 | SPINT2 | U78095 | 6.7 |
| 1061_at | GATA binding protein 3 | GATA3 | X58072 | 4.9 |
| 39330_s_at | interleukin 10 receptor, alpha | IL10RA | U00672 | 4.6 |
| 37121_at | actinin, alpha 1 | ACTN1 | M95178 | 3.9 |
| 34173_s_at | natural killer cell group 7 sequence | NKG7 | S69115 | 3.6* |
| 37544_at | contactin 5 | CNTN5 | AB013802 | 3.4* |
| 34319_at | nuclear factor, interleukin 3 regulated | NFIL3 | X64318 | 3.4 |
| 37038_at | S100 calcium binding protein P | S100P | AA131149 | 3.1 |
| 931_at | ATP-binding cassette, sub-family D (ALD), member 3 | ABCD3 | X83467 | 3.0 |
| 40839_at | Epstein-Barr virus induced gene 2 (lymphocyte-specific G protein-coupled receptor) | EBI2 | L08177 | 2.9 |
| 33352_at | ubiquitin-like 3 | UBL3 | AL080177 | 2.7 |
| 37403_at | H2B histone family, member Q | H2BFQ | X57985 | 2.6* |
| 39239_at | annexin A1 | ANXA1 | X05908 | 2.6 |
| 1067_at | CD8 antigen, beta polypeptide 1 (p37) | CD8B1 | X13444 | 2.5* |
| 41577_at | fms-related tyrosine kinase 3 ligand | FLT3LG | U03858 | 2.5* |
| | protein phosphatase 1, regulatory (inhibitor) subunit 16B | PPP1R16B | AB020630 | 2.5 |

6 h

TABLE 1-continued

| | ID | Description | Symbol | Accession | Value |
|---|---|---|---|---|---|
| | 1545_g_at | zyxin | ZYX | S77812 | 2.4* |
| | 31546_g_at | small inducible cytokine subfamily C, member 1 (lymphotactin) | SCYC1 | D63789 | 2.4 |
| | 649_s_at | chemokine (C—X—C motif), receptor 4 (fusin) | CXCR4 | L06797 | 2.3 |
| | 38051_at | mal, T-cell differentiation protein | MAL | X76220 | 2.2 |
| | 333_s_at | Single-Stranded Dna-Binding Protein Mssp-1 | | HG2639-HT2735 | 2.1 |
| | 37603_at | Interleukin 1 receptor antagonist | IL1RN | X52015 | 2.1 |
| | 34256_at | sialyltransferase 9 (CMP-NeuAc:lactosylceramide alpha-2,3-sialyltransferase; GM3 synthase) | SIAT9 | AB018356 | −2.1* |
| | 34342_s_at | secreted phosphoprotein 1 (osteopontin, bone sialoprotein I, early T-lymphocyte activation 1) | SPP1 | AF052124 | −2.1 |
| | 40385_at | small inducible cytokine subfamily A (Cys—Cys), member 20 | SCYA20 | U64197 | −2.3 |
| | 41209_at | lipoprotein lipase | LPL | M15856 | −2.3 |
| | 34375_at | small inducible cytokine A2 (monocyte chemotactic protein 1) | SCYA2 | M28225 | −2.5 |
| | 41744_at | optineurin | OPTN | AF070533 | −2.5* |
| | 32649_at | transcription factor 7 (T-cell specific, HMG-box) | TCF7 | X59871 | −2.6 |
| | 2092_s_at | secreted phosphoprotein 1 (osteopontin, bone sialoprotein I, early T-lymphocyte activation 1) | SPP1 | J04765 | −2.8 |
| | 36239_at | POU domain, class 2, associating factor 1 | POU2AF1 | Z49194 | −2.9 |
| | 875_g_at | small inducible cytokine A2 (monocyte chemotactic protein 1) | SCYA2 | M26683 | −3.1 |
| | 38578_at | Tumor necrosis factor receptor superfamily, member 7 | TNFRSF7 | M63928 | −3.1 |
| | 37043_at | inhibitor of DNA binding 3, dominant negative helix-loop-helix protein | ID3 | AL021154 | −4.4 |
| | 33540_at | Homo sapiens mRNA; cDNA DKFZp564A023 (from clone DKFZp564A023) | | AL049233 | −4.6* |
| | 39586_at | desmoglein 1 | DSG1 | AF097935 | −4.6* |
| | 37137_at | granzyme B (granzyme 2, cytotoxic T-lymphocyte-associated serine esterase 1) | GZMB | M17016 | 10.8 |
| | 41504_s_at | v-maf musculoaponeurotic fibrosarcoma (avian) oncogene homolog | MAF | AF055376 | 8.9 |
| | 1892_s_at | neurotrophic tyrosine kinase, receptor type 1 | Trk | HG1437-HT1437 | 8.8 |
| 48 h | 41193_at | dual specificity phosphatase 6 | DUSP6 | AB013382 | 8.7 |
| | 34439_at | absent in melanoma 2 | AIM2 | AF024714 | 7.9 |
| | 1069_at | cyclooxygenase-2 | Cox-2 | U04636 | 6.6* |
| | 41592_at | JAK binding protein | SSI-1 | AB000734 | 6.0 |
| | 37038_at | peroxisomal membrane protein-1 | ABCD3 | X83467 | 5.9 |
| | 41505_r_at | v-maf musculoaponeurotic fibrosarcoma (avian) oncogene homolog | MAF | AF055376 | 5.9* |
| | 35938_at | phospholipase A2, group IVA (cytosolic, calcium-dependent) | PLA2G4A | M72393 | 5.7 |
| | 37544_at | nuclear factor, interleukin 3 regulated | NFIL3 | X64318 | 5.4 |
| | 40511_at | GATA-binding protein 3 | GATA3 | X58072 | 4.9 |
| | 36805_s_at | neurotrophic tyrosine kinase, receptor, type 1 | NTRK1 | X03541 | 4.7 |
| | 931_at | Epstein-Barr virus induced gene 2 (lymphocyte-specific G protein-coupled receptor) | EBI2 | L08177 | 4.7 |
| | 41772_at | monoamine oxidase A | MAOA | M68840 | 4.1 |
| | 1368_at | interleukin 1 receptor, type I | IL1R1 | M27492 | 3.9 |
| | 34678_at | fer-1-like 3, myoferlin | FER1L3 | AL096713 | 3.7* |
| | 37121_at | natural killer cell group 7 sequence | NKG7 | S69115 | 3.5 |
| | 36899_at | special AT-rich sequence binding protein 1 (binds to nuclear matrix/scaffold-associating DNAs) | SATB1 | M97287 | 3.4 |
| | 39942_at | basic leucine zipper transcription factor, ATF-like | B-ATF | AF016898 | 3.2 |
| | 38336_at | KIAA1013 protein | KIAA1013 | AB023230 | 3.1 |
| | 41215_s_at | inhibitor of DNA binding 2, dominant negative helix-loop-helix protein | ID2 | D13891 | 2.7 |
| | 1062_g_at | interleukin 10 receptor, alpha | IL10RA | U00672 | 2.7 |
| | 33305_at | serine (or cysteine) proteinase inhibitor, clade B (ovalbumin), member 1 | SERPINB1 | M93056 | 2.6 |
| | 40848_g_at | KIAA0750 gene product | KIAA0750 | AB018293 | 2.5 |
| | 37524_at | serine/threonine kinase 17b (apoptosis-inducing) | STK17B | AB011421 | 2.4 |
| | 34517_at | 3-hydroxy-3-methylglutaryl-Coenzyme A synthase 1 (soluble) | HMGCS1 | X66435 | 2.4 |

TABLE 1-continued

| | AFFY PROBE ID | GENE NAME | SYMBOL | ACCESSION | FOLD CHANGE |
|---|---|---|---|---|---|
| | 34348_at | serine protease inhibitor, Kunitz type, 2 | SPINT2 | U78095 | 2.3 |
| | 40448_at | zinc finger protein 36, C3H type, homolog (mouse) | ZFP36 | M92843 | 2.2 |
| | 37732_at | AU RNA-binding protein/enoyl-Coenzyme A hydratase | RYBP | AL049940 | 2.2 |
| | 37616_at | BCL2-related protein A1 | AUH | X79888 | 2.2 |
| | 2002_s_at | I-mfa domain-containing protein | BCL2A1 | U27467 | 2.0 |
| | 37842_at | CD83 antigen (activated B lymphocytes, immunoglobulin superfamily) | . | AF054589 | -2.0 |
| | 37536_at | guanylate binding protein 1, interferon-inducible, 67 kD | CD83 | Z11697 | -2.2 |
| | 35735_at | signal transducer and activator of transcription 1, 91 kD | GBP1 | M55542 | -2.4 |
| | 32859_at | phosphodiesterase 4B, cAMP-specific (dunce (Drosophila)-homolog phosphodiesterase E4) | STAT1 | M97935 | -2.4 |
| | 33705_at | | PDE4B | L20971 | -2.6* |
| | 33339_g_at | signal transducer and activator of transcription 1 | ISGF3 | M97936 | -2.9 |
| | 38575_at | signal transducer and activator of transcription 1 | MALT1 | AF070528 | -3.0* |
| | 33338_at | nuclear receptor subfamily 4, group A, member 2 | ISGF3 | M97936 | -3.2 |
| | 37623_at | lymphotoxin beta (TNF superfamily, member 3) | NR4A2 | X75918 | -3.3 |
| | 40729_s_at | myxovirus (influenza) resistance 1, homolog of murine (interferon-inducible protein p78) | LTB | Y14768 | -3.4 |
| | 37014_at | putative lymphocyte G0/G1 switch gene | MX1 | M33882 | -3.5 |
| | 38326_at | nuclear receptor subfamily 4, group A, member 2 | G0S2 | M69199 | -3.8 |
| | 547_s_at | | NR4A2 | S77154 | -4.6 |

Differences between Th1-induced vs Th2-induced human CD4+ T cells

| TIME | AFFY PROBE ID | GENE NAME | SYMBOL | ACCESSION | FOLD CHANGE |
|---|---|---|---|---|---|
| 2 h | 37043_at | inhibitor of DNA binding 3, dominant negative helix-loop-helix protein | ID3 | AL021154 | 2.5 |
| | 37909_at | laminin, alpha 3 (nicein (150 kD), kalinin (165 kD), BM600 (150 kD), epilegrin) | LAMA3 | L34155 | 2.4 |
| | 36160_s_at | protein tyrosine phosphatase, receptor type, N polypeptide 2 | PTPRN2 | U81561 | 2.3* |
| | 39827_at | HIF-1 responsive RTP801 | RTP801 | AA522530 | 2.1 |
| | 38578_at | tumor necrosis factor receptor superfamily, member 7 | TNFRSF7 | M63928 | 2.1 |
| | 41475_at | ninjurin 1 | NINJ1 | U91512 | 2.0 |
| | 1860_at | tumor protein p53 binding protein, 2 | TP53BP2 | U58334 | -2.0 |
| | 40511_at | GATA binding protein 3 | GATA3 | X58072 | -2.1 |
| | 35320_at | solute carrier family 11 (proton-coupled divalent metal ion transporters), member 2 | SLC11A2 | AB004857 | -2.1 |
| | 37524_at | serine/threonine kinase 17b (apoptosis-inducing) | STK17B | AB011421 | -2.2 |
| | 32919_at | Homo sapiens, clone IMAGE: 3625286, mRNA, partial cds | . | AC004010 | -2.3* |
| | 1061_at | interleukin 10 receptor, alpha | IL10RA | U00672 | -2.3 |
| | 39549_at | hypothetical protein FLJ23138 | FLJ23138 | AI743090 | -2.3* |
| | 33352_at | H2B histone family, member Q | H2BFQ | X57985 | -2.4 |
| | 36899_at | special AT-rich sequence binding protein 1 (binds to nuclear matrix/scaffold-associating DNA'S) | SATB1 | M97287 | -2.5 |
| | 33260_at | son of sevenless homolog 1 (Drosophila) | SOS1 | L13857 | -2.5 |
| | 758_at | prostaglandin I2 (prostacyclin) receptor (IP) | PTGIR | D38128 | -2.5* |
| | 1816_at | RAS p21 protein activator 2 | RASA2 | D78156 | -2.5 |
| | 34398_at | heat shock 105 kD | HSP105B | D86956 | -2.6* |
| | 38051_at | mal, T-cell differentiation protein | MAL | X76220 | -2.6 |
| | 33291_at | RAS guanyl releasing protein 1 (calcium and DAG-regulated) | RASGRP1 | AF081195 | -2.6 |
| | 34348_at | serine protease inhibitor, Kunitz type, 2 | SPINT2 | U78095 | -2.6 |
| | 35712_at | leucine-rich repeat protein, neuronal 3 | LRRN3 | AC004142 | -2.6 |
| | 40456_at | up-regulated by BCG-CWS | LOC64116 | AL049963 | -2.8 |
| | 41592_at | JAK binding protein | SSI-1 | AB000734 | -2.9 |

TABLE 1-continued

| | | | | | |
|---|---|---|---|---|---|
| | 38149_at | | KIAA0053 gene product | KIAA0053 | D29642 | -2.9 |
| | 33809_at | | guanine nucleotide binding protein (G protein), alpha inhibiting activity polypeptide 1 | GNAI1 | AL049933 | -2.9 |
| | 36435_at | | protein phosphatase 1A (formerly 2C), magnesium-dependent, alpha isoform | PPM1A | AF070670 | -3.0 |
| | 32058_at | | HNK-1 sulfotransferase | HNK-1ST | AF070594 | -3.0 |
| | 36148_at | | amyloid beta (A4) precursor-like protein 1 | APLP1 | U48437 | -3.5* |
| | 41193_at | | dual specificity phosphatase 6 | DUSP6 | AB013382 | -3.7 |
| | 41384_at | | receptor-interacting serine-threonine kinase 2 | RIPK2 | AF117829 | -3.9 |
| | 33047_at | | ESTs, Weakly similar to B34087 hypothetical protein [H. sapiens] | | AI971169 | -4.0 |
| | 1062_g_at | | interleukin 10 receptor, alpha | IL10RA | U00672 | -4.0 |
| | 587_at | | endothelial differentiation, sphingolipid G-protein-coupled receptor, 1 | EDG1 | M31210 | -4.1 |
| | 32148_at | | FERM, RhoGEF (ARHGEF) and pleckstrin domain protein 1 (chondrocyte-derived) | FARP1 | AT701049 | -4.3* |
| | 37544_at | | nuclear factor, interleukin 3 regulated | NFIL3 | X64318 | -5.1 |
| | 974_at | | mitogen-activated protein kinase kinase kinase 14 | MAP3K14 | Y10256 | -5.3 |
| | 35659_at | | interleukin 10 receptor, alpha | IL10RA | U00672 | -5.7 |
| | 39593_at | | Homo sapiens, Similar to fibrinogen-like 2, clone MGC: 22391 IMAGE: 4616866, mRNA, complete cds | | AI432401 | -9.2 |
| | 38549_at | | vipirin | cig5 | AF026941 | -35.5 |
| | 40085_s_at | | transcription factor CP2 | TFCP2 | U03495 | 9.2* |
| | 40757_at | | granzyme A (granzyme 1, cytotoxic T-lymphocyte-associated serine esterase 3) | GZMA | M18737 | 3.6 |
| | 32041_r_at | | CDC5 cell division cycle 5-like (S. pombe) | CDC5L | AB007892 | 3.5* |
| | 36705_at | | protein kinase, AMP-activated, beta 2 non-catalytic subunit | PRKAB2 | AJ224538 | 3.1* |
| | 32649_at | | transcription factor 7 (T-cell specific, HMG-box) | TCF7 | X59871 | 2.9 |
| | 40091_at | | B-cell CLL/lymphoma 6 (zinc finger protein 51) | BCL6 | U00115 | 2.8 |
| | 875_g_at | | small inducible cytokine A2 (monocyte chemotactic protein 1) | SCYA2 | M26683 | 2.8 |
| | 36239_at | | POU domain, class 2, associating factor 1 | POU2AF1 | Z49194 | 2.7 |
| | 38578_at | | tumor necrosis factor receptor superfamily, member 7 | TNFRSF7 | M63928 | 2.7 |
| | 34252_at | | hypothetical protein FLJ10342 | FLJ10342 | W28545 | 2.6* |
| | 35735_at | | guanylate binding protein 1, interferon-inducible, 67 kD | GBP1 | M55542 | 2.4 |
| | 39389_at | | CD9 antigen (p24) | CD9 | M38690 | 2.4 |
| | 40702_at | | interferon, gamma | IFNG | X13274 | 2.3 |
| | 1369_s_at | | interleukin 8 | IL8 | M28130 | 2.2 |
| | 37485_at | | fatty-acid-Coenzyme A ligase, very long-chain 1 | FACVL1 | D88308 | 2.2 |
| | 40698_at | | C-type (calcium dependent, carbohydrate-recognition domain) lectin, superfamily member 2 (activation-induced) | CLECSF2 | X96719 | 2.2 |
| | 1954_at | | kinase insert domain receptor (a type III receptor tyrosine kinase) | KDR | AF035121 | 2.0* |
| | 34256_at | | sialyltransferase 9 (CMP-NeuAc: lactosylceramide alpha-2,3-sialyltransferase; GM3 synthase) | SIAT9 | AB018356 | 2.0* |
| 6 h | 37025_at | | LPS-induced TNF-alpha factor | PIG7 | AL120815 | 2.0 |
| | 35693_at | | hippocalcin-like 1 | HPCAL1 | AF070616 | 2.0 |
| | 38051_at | | mal, T-cell differentiation protein | MAL | X76220 | -2.1 |
| | 558_at | | keratin 1 (epidermolytic hyperkeratosis) | KRT1 | M98776 | -2.1* |
| | 34319_at | | S100 calcium binding protein P | S100P | AA131149 | -2.2 |
| | 37403_at | | annexin A1 | ANXA1 | X05908 | -2.3 |
| | 31496_g_at | | small inducible cytokine subfamily C, member 1 (lymphotactin) | SCYC1 | D63789 | -2.4 |
| | 37038_at | | ATP-binding cassette, sub-family D (ALD), member 3 | ABCD3 | X83467 | -2.4 |
| | 40839_at | | ubiquitin-like 3 | UBL3 | AL080177 | -2.4 |
| | 35794_at | | KIAA0942 protein | KIAA0942 | AB023159 | -2.5* |
| | 39330_s_at | | actinin, alpha 1 | ACTN1 | M95178 | -2.5 |
| | 974_at | | mitogen-activated protein kinase kinase kinase 14 | MAP3K14 | Y10256 | -2.6 |
| | 37544_at | | nuclear factor, interleukin 3 regulated | NFIL3 | X64318 | -2.8 |

TABLE 1-continued

| | | | | |
|---|---|---|---|---|
| | 37398_at | platelet/endothelial cell adhesion molecule (CD31 antigen) | PECAM1 | AA100961 | -2.9* |
| | 931_at | Epstein-Barr virus induced gene 2 (lymphocyte-specific G protein-coupled receptor) | EBI2 | L08177 | -2.9 |
| | 1061_at | interleukin 10 receptor, alpha | IL10RA | U00672 | -3.1 |
| | 37121_at | natural killer cell group 7 sequence | NKG7 | S69115 | -3.5 |
| | 39239_at | CD8 antigen, beta polypeptide 1 (p37) | CD8B1 | X13444 | -3.5 |
| | 35422_at | microtubule-associated protein 2 | MAP2 | U01828 | -3.6* |
| | 40511_at | GATA binding protein 3 | GATA3 | X58072 | -4.0 |
| | 34990_at | SET binding protein 1 | SETBP1 | AB022660 | -4.4* |
| | 41592_at | JAK binding protein | SSI-1 | AB000734 | -5.3 |
| | 34348_at | serine protease inhibitor, Kunitz type, 2 | SPINT2 | U78095 | -5.9 |
| | 38549_at | vipirin | cig5 | AF026941 | -6.1 |
| | 1062_g_at | interleukin 10 receptor, alpha | IL10RA | U00672 | -6.3 |
| | 41193_at | dual specificity phosphatase 6 | DUSP6 | AB013382 | -6.7 |
| | 40702_at | interferon, gamma | IFNG | X13274 | 115.4 |
| | 1021_at | interferon, gamma | IFNG | J00219 | 48.8 |
| | 33093_at | interleukin 18 receptor accessory protein | IL18RAP | AF077346 | 18.4 |
| | 1611_s_at | interferon, gamma | IFNG | J00219 | 18.2 |
| | 38326_at | putative lymphocyte G0/G1 switch gene | G0S2 | M69199 | 10.6 |
| | 1538_s_at | interleukin 2 | IL2 | X00695 | 7.3 |
| | 31792_at | annexin A3 | ANXA3 | M20560 | 6.0 |
| | 39264_at | 2'-5'-oligoadenylate synthetase 2 (69–71 kD) | OAS2 | M87284 | 4.0* |
| | 34021_at | interleukin 2 | IL2 | S82692 | 3.5 |
| | 32370_at | cytotoxic T-lymphocyte-associated serine esterase 1 | CTLA1 | M57888 | 3.2 |
| | 31961_r_at | | . | AF070579 | 2.8* |
| | 38463_s_at | adenosine monophosphate deaminase (isoform E) | AMPD3 | U29926 | 2.5* |
| | 34607_at | inducible T-cell co-stimulator | ICOS | AB023135 | 2.3 |
| | 40396_at | purinergic receptor P2X, ligand-gated ion channel, 5 | P2RX5 | U49395 | 2.2* |
| | 1004_at | Burkitt lymphoma receptor 1, GTP-binding protein | BLR1 | X68149 | 2.1* |
| | 441_s_at | Leukemia inhibitory factor (cholinergic differentiation factor) | LIF | X13967 | 2.0* |
| | 34678_at | fer-1-like 3, myoferlin | FER1L3 | AL096713 | -2.1* |
| | 35712_at | leucine-rich repeat protein, neuronal 3 | LRRN3 | AC004142 | -2.3 |
| | 34091_s_at | vimentin | VIM | Z19554 | -2.3 |
| | 40456_at | | . | AL049963 | -2.3 |
| | 33541_s_at | leukocyte-associated Ig-like receptor 2 | LAIR2 | AA133246 | -2.4 |
| | 1061_at | interleukin 10 receptor, alpha | IL10RA | U00672 | -2.4 |
| | 36899_at | special AT-rich sequence binding protein 1 (binds to nuclear matrix/scaffold-associating DNA's) | SATB1 | M97287 | -2.5 |
| | 36926_at | mitogen-activated protein kinase 6 | MAPK6 | X80692 | -2.6* |
| | 649_s_at | chemokine (C—X—C motif), receptor 4 (fusin) | CXCR4 | L06797 | -2.7 |
| | 38685_at | hypothetical protein MGC14797 | MGC14797 | AL035306 | -2.8* |
| | 34348_at | serine protease inhibitor, Kunitz type, 2 | SPINT2 | U78095 | -3.0 |
| | 40049_at | death-associated protein kinase 1 | DAPK1 | X76104 | -3.0* |
| | 37544_at | nuclear factor, interleukin 3 regulated | NFIL3 | X64318 | -3.1 |
| | 39331_at | tubulin, beta polypeptide | TUBB | X79535 | -3.2* |
| | 31856_at | glycoprotein A repetitions predominant | GARP | Z24680 | -3.6 |
| | 931_at | Epstein-Barr virus induced gene 2 (lymphocyte-specific G protein-coupled receptor) | EBI2 | L08177 | -3.8 |
| | 41504_s_at | v-maf musculoaponeurotic fibrosarcoma (avian) oncogene homolog | MAF | AF055376 | -4.0 |
| | 41193_at | dual specificity phosphatase 6 | DUSP6 | AB013382 | -4.1 |
| | 494_at | interleukin 13 | IL-13 | U31120 | -4.3* |
| | 1069_at | | Cox-2 | U04636 | -4.8* |
| | 33809_at | guanine nucleotide binding protein (G protein), alpha inhibiting activity polypeptide 1 | GNAI1 | AL049933 | -4.9 |
| | 1062_g_at | interleukin 10 receptor, alpha | IL10RA | U00672 | -5.2 |

48 h row marker appears before 36926_at

TABLE 1-continued

| AFFY PROBE ID | GENE NAME | SYMBOL | ACCESSION | FOLD CHANGE |
|---|---|---|---|---|
| 37038_at | peroxisomal membrane protein-1 | ABCD3 | X83467 | -5.7 |
| 41592_at | JAK binding protein | SSI-1 | AB000734 | -7.2 |
| 36805_s_at | neurotrophic tyrosine kinase, receptor, type 1 | NTRK1 | X03341 | -8.2 |
| 40511_at | GATA-binding protein 3 | GATA3 | X58072 | -8.8 |
| 35938_at | phospholipase A2, group IVA (cytosolic, calcium-dependent) | PLA2G4A | M72393 | -10.5* |
| 41772_at | monoamine oxidase A | MAOA | M68840 | -11.1 |
| 1892_s_at | neurotrophic tyrosine kinase, receptor, type 1 | Trk | HG1437-HT1437 | -12.2 |

Target genes of TGFb in human CD4+ T cells cultured in Th1 conditions (Th1-induced +TGFb vs Th1-induced))

| TIME | AFFY PROBE ID | GENE NAME | SYMBOL | ACCESSION | FOLD CHANGE |
|---|---|---|---|---|---|
| 2 h | 41049_at | insulin receptor substrate 1 | IRS1 | S62539 | 3.7* |
| | 34414_at | KIAA0368 protein | KIAA0368 | AB002366 | 2.9* |
| | 37909_at | laminin, alpha 3 (nicein (150 Kd), kalinin (165 Kd), BM600 (150 Kd), epilegrin) | LAMA3 | L34155 | 2.2 |
| | 39822_s_at | growth arrest and DNA-damage-inducible, beta | GADD45B | AF078077 | 2.0 |
| | 32870_g_at | MRE11 meiotic recombination 11 homolog A (S. cerevisiae) | MRE11A | AF073362 | -2.4* |
| | 32639_at | nucleoporin-like protein 1 | NLP_1 | U97198 | -2.5* |
| | 33042_r_at | Homo sapiens clone 24442 Mrna sequence | | AF055018 | -3.1* |
| | 38645_at | DKFZP434A043 protein | DKFZP434A043 | AL096748 | -3.4* |
| | 41779_at | regulator of G-protein ignaling 16 | RGS16 | U70426 | 7.2 |
| | 40923_at | Homo sapiens Cdna: FLJ21449 fis, clone COL04483, highly similar to AF010235 Homo sapiens Mrna from chromosome 5q31–33 region | . | AA290994 | 5.3* |
| 6 h | 38325_at | multiple inositol polyphosphate histidine phosphatase, 1 | MINPP1 | AL050356 | 4.9 |
| | 37391_at | cathepsin L | CTSL | X12451 | 3.9 |
| | 35338_at | paired basic amino acid cleaving enzyme (furin, membrane associated receptor protein) | PACE | X17094 | 3.1 |
| | 32583_at | v-jun sarcoma virus 17 oncogene homolog (avian) | JUN | J04111 | 3.0 |
| | 37669_s_at | ATPase, Na+/K+ transporting, beta 1 polypeptide | ATP1B1 | U16799 | 3.0 |
| | 1388_g_at | vitamin D (1,25-dihydroxyvitamin D3) receptor | VDR | J03258 | 2.9 |
| | 2031_s_at | cyclin-dependent kinase inhibitor 1A (p21, Cip1) | CDKN1A | U03106 | 2.5 |
| | 40385_at | small inducible cytokine subfamily A (Cys—Cys), member 20 | SCYA20 | U64197 | 2.5 |
| | 1830_s_at | transforming growth factor, beta 1 (Camurati-Engelmann disease) | TGFB1 | M38449 | 2.5 |
| | 38077_at | collagen, type VI, alpha 3 | COL6A3 | X52022 | 2.5 |
| | 41438_at | oxysterol binding protein-like 8 | OSBPL8 | AL049923 | 2.4 |
| | 32607_at | Brain abundant, membrane attached signal protein 1 | BASP1 | AF039656 | 2.3 |
| | 33812_at | a disintegrin and metalloproteinase domain 19 (meltrin beta) | ADAM19 | AL049415 | 2.3 |
| | 39071_at | integrin, alpha V (vitronectin receptor, alpha polypeptide, antigen CD51) | ITGAV | M14648 | 2.2 |
| | 39827_at | HIF-1 responsive RTP801 | RTP801 | AA522530 | 2.1 |
| | 37043_at | inhibitor of DNA binding 3, dominant negative helix-loop-helix protein | ID3 | AL021154 | 2.1 |
| | 1857_at | MAD, mothers against decapentaplegic homolog 7 (Drosophila) | MADH7 | AF010193 | 2.0* |
| | 37279_at | GTP binding protein overexpressed in skeletal muscle | GEM | U10550 | 2.0 |

Target genes of TGFb in human CD4+ T cells cultured in Th2 conditions (Th2-induced + TGFb vs Th2-induced))

| TIME | AFFY PROBE ID | GENE NAME | SYMBOL | ACCESSION | FOLD CHANGE |
|---|---|---|---|---|---|
| 2 h | 33435_r_at | BET1 homolog (S. cerevisiae) | BET1 | AI525962 | 6.3* |
| | 32709_at | potassium voltage-gated channel, shaker-related subfamily, beta member 1 | KCNAB1 | L39833 | 4.0* |
| | 40095_at | carbonic anhydrase II | CA2 | J03037 | 2.3 |
| | 2031_s_at | cyclin-dependent kinase inhibitor 1A (p21, Cip1) | CDKN1A | U03106 | 2.0 |
| | 32770_at | SEC24 related gene family, member D (S. cerevisiae) | SEC24D | AB018298 | -36.6* |
| 6 h | 39260_at | solute carrier family 16 (monocarboxylic acid transporters), member 4 | SLC16A4 | U59185 | 8.6* |

TABLE 1-continued

| | | | | |
|---|---|---|---|---|
| 32583_at | v-jun sarcoma virus 17 oncogene homolog (avian) | JUN | J04111 | 8.3 |
| 1388_g_at | vitamin D (1,25-dihydroxyvitamin D3) receptor | VDR | J03258 | 4.4 |
| 41779_at | regulator of G-protein signalling 16 | RGS16 | U70426 | 4.3 |
| 40647_at | Kell blood group precursor (McLeod phenotype) | XK | Z32684 | 3.2* |
| 37391_at | cathepsin L | CTSL | X12451 | 3.1 |
| 555_at | RAB40B, member RAS oncogene family | RAB40B | U05227 | 3.1* |
| 40385_at | small inducible cytokine subfamily A (Cys—Cys), member 20 | SCYA20 | U64197 | 3.0 |
| 33186_i_at | ESTs | | AL046961 | 2.9* |
| 38077_at | collagen, type VI, alpha 3 | COL6A3 | X52022 | 2.5 |
| 41788_i_at | KIAA0669 gene product | KIAA0669 | AB014569 | 2.5 |
| 312_s_at | | | HG3075-HT3236 | 2.5 |
| 35338_at | paired basic amino acid cleaving enzyme (furin, membrane associated receptor protein) | PACE | X17094 | 2.4 |
| 36089_at | Sac domain-containing inositol phosphatase 2 | SAC2 | AB023183 | 2.3 |
| 34800_at | ortholog of mouse integral membrane glycoprotein LIG-1 | LIG1 | AL039458 | 2.2 |
| 33893_r_at | KIAA0470 gene product | KIAA0470 | AB007939 | 2.1 |
| 40790_at | basic helix-loop-helix domain containing, class B, 2 | BHLHB2 | AB004066 | 2.1 |
| 37279_at | GTP binding protein overexpressed in skeletal muscle | GEM | U10550 | 2.1 |
| 40399_r_at | mesenchyme homeo box 2 (growth arrest-specific homeo box) | MEOX2 | AI743406 | −2.3* |
| 528_at | heat shock 27 kD protein 3 | HSPB3 | U15590 | −3.9* |
| 41291_at | GDP dissociation inhibitor 2 | GDI2 | AC004528 | −8.0 |
| 37669_s_at | ATPase, Na+/K+ transporting, beta 1 polypeptide | ATP1B1 | U16799 | 11.5 |
| 1183_at | small inducible cytokine subfamily A (Cys—Cys), member 17 | SCYA17 | D43767 | 10.1 |
| 1405_i_at | small inducible cytokine A5 (RANTES) | SCYA5 | M21121 | 8.5 |
| 977_s_at | cadherin 1, type 1, E-cadherin | ECAD3 | Z35402 | 8.1 |
| 35367_at | lectin, galactoside-binding, soluble, 3 (galectin 3) | LGALS3 | AB006780 | 5.9 |
| 1403_s_at | small inducible cytokine A5 (RANTES) | SCYA5 | M21121 | 5.4 |
| 32607_at | brain abundant, membrane attached signal protein 1 | BASP1 | AF039656 | 4.1 |
| 34037_at | interleukin 9 | IL9 | M30134 | 3.9 |
| 35824_at | zinc finger protein 238 | ZNF238 | AJ223321 | 3.7* |
| 36575_at | regulator of G-protein signalling 1 | RGS1 | S59049 | 3.7 |
| 36117_at | PTK2 protein tyrosine kinase 2 | PTK2 | L13616 | 3.5 |
| 34739_at | hypothetical protein FLJ20275 | FLJ20275 | W26023 | 3.4* |
| 37603_at | interleukin 1 receptor antagonist | IL1RN | X52015 | 3.2 |
| 39248_at | aquaporin 3 | AQP3 | N74607 | 3.1 |
| 34217_at | Kruppel-like factor 7 (ubiquitous) | KLF7 | AB015132 | 2.5 |
| 37377_i_at | lamin A/C | LMNA | M13452 | 2.4 |
| 40818_at | H-2K binding factor-2 | LOC51580 | D14041 | 2.4 |
| 37391_at | cathepsin L | CTSL | X12451 | 2.3* |
| 32587_at | zinc finger protein 36, C3H type-like 2 | ZFP36L2 | U07802 | 2.2* |
| 32778_at | inositol 1,4,5-triphosphate receptor, type 1 | ITPR1 | D26070 | −2.1* |
| 38006_at | CD48 antigen (B-cell membrane protein) | CD48 | M37766 | −2.2 |
| 41215_s_at | inhibitor of DNA binding 2, dominant negative helix-loop-helix protein | ID2 | D13891 | −2.2 |
| 33849_at | pre-B-cell colony-enhancing factor | PBEF | U02020 | −2.3 |
| 34801_at | KIAA0710 gene product | KIAA0710 | AB014610 | −2.4* |
| 34098_f_at | integrin cytoplasmic domain-associated protein 1 | ICAP-1A | AI799757 | −2.5 |
| 36377_at | interleukin 18 receptor 1 | IL18R1 | U43672 | −2.5 |
| 1069_at | cyclooxygenase-2 | Cox-2 | U04636 | −2.5* |
| 38122_at | solute carrier family 23 (nucleobase transporters), member 1 | SLC23A1 | D87075 | −2.6* |
| 35943_s_at | GA-binding protein transcription factor, beta subunit 1 (53 kD) | GABPB1 | D13317 | −2.8* |
| 2002_s_at | BCL2-related protein A1 | BCL2A1 | U27467 | −2.9 |
| 33809_at | guanine nucleotide binding protein (G protein), alpha inhibiting activity polypeptide 1 | GNAI1 | AL049933 | −2.9* |

48 h

TABLE 1-continued

Summary of data on target genes of IL-12 at 48 h in human CD4+ T cells (Th1-induced vs activated)

| Probe_ID | RL3 Signal Log Ratio | RL4 Signal Log Ratio | Accession | Gene name | Gene symbol | Locus | Functional group |
|---|---|---|---|---|---|---|---|
| 34965_at | 8.43 | 5.22 | | cystatin F (leukocystatin) | CST7 | | AF031824 -3.0 |
| 37544_at | 5.26 | 5 | | nuclear factor, interleukin 3 regulated | NFIL3 | | X64318 -3.0 |
| 36160_s_at | | | | protein tyrosine phosphatase, receptor type, N polypeptide 2 | PTPRN2 | | U81561 -3.1 |
| 35938_at | | | | phospholipase A2, group IVA (cytosolic, calcium-dependent) | PLA2G4A | | M72393 -4.0 |
| 40702_at | 6.07 | 3.55 | X13274 | interferon, gamma | IFNG | 12q14 | Cytokines, chemokines and other ligands |
| 1021_at | | | J00219 | interferon, gamma | IFNG | 12q14 | Cytokines, chemokines and other ligands |
| 1611_s_at | | | J00219 | interferon, gamma | IFNG | 12q14 | Cytokines, chemokines and other ligands |
| 33093_at | 2.95 | 4.22 | AF077346 | interleukin 18 receptor accessory protein | IL18RAP | 2p24.3–p24.1 | Cell surface molecule |
| 37137_at | 2.96 | 4.05 | M17016 | granzyme B (granzyme 2, cytotoxic T-lymphocyte-associated serine esterase 1) | GZMB | 14q11.2 | Enzymes and other pathway molecules |
| 32370_at | 2.59 | 2.39 | M57888 | cytotoxic T-lymphocyte-associated serine esterase 1 | CTLA1 | 14q11.2 | Enzymes and other pathway molecules |
| 35338_at | 1.68 | 2.21 | X17094 | paired basic amino acid cleaving enzyme (furin, membrane associated receptor protein) | PACE | 15q25–q26 | Enzymes and other pathway molecules |
| 38326_at | 1.65 | 1.92 | M69199 | putative lymphocyte G0/G1 switch gene | G0S2 | 1 | Enzymes and other pathway molecules |
| 38278_at | 1.47 | 2.09 | M62324 | modulator recognition factor I | MRF-1 | 2p11.1 | Transcriptional regulator |
| 33305_at | 1.62 | 1.74 | M93056 | serine (or cysteine) proteinase inhibitor, clade B (ovalbumin), member 1 | SERPINB1 | 6p25 | Enzymes and other pathway molecules |
| 1004_at | 1.75 | 1.05 | X68149 | Burkitt lymphoma receptor 1, GTP-binding protein | BLR1 | 11q23.3 | Cell surface molecule |
| 36776_at | 1.33 | 1.41 | X51985 | lymphocyte-activation gene 3 | LAG3 | 12p13.32 | Cell surface molecule |
| 40635_at | 1.16 | 1.47 | AF089750 | flotillin 1 | FLOT1 | 6p21.3 | Unclassified |
| 1534_at | 1.05 | 1.38 | U64198 | interleukin 12 receptor, beta 2 | IL12RB2 | 1p31.3–p31.2 | Cell surface molecule |
| 33513_at | 1.13 | 1.08 | U33017 | signaling lymphocytic activation molecule | SLAM | 1q22–q23 | Cell surface molecule |
| 34654_at | 1.04 | 1.04 | AJ224979 | myotubularin related protein 1 | MTMR1 | Xq28 | Enzymes and other pathway molecules |
| 38620_at | -1.11 | -1.33 | AA905543 | golgi SNAP receptor complex member 2 | GOSR2 | 17q21 | Structural and intracellular trafficing molecules |
| 37623_at | -1.64 | -1.05 | X75918 | nuclear receptor subfamily 4, group A, member 2 | NR4A2 | 2q22–q23 | Transcriptional regulator |
| 34866_at | -1.37 | -1.64 | AF055029 | glycoprotein A repetitions predominant | GARP | 11q13.5–q14 | Unclassified |
| 31856_at | -1.92 | -1.1 | Z24680 | | | | Cell surface molecule |
| 39582_at | -1.97 | -1.12 | AL050166 | | | | Unclassified |
| 38575_at | -1.83 | -1.37 | AF070528 | | | | Unclassified |
| 31496_g_at | -1.92 | -1.38 | D63789 | small inducible cytokine subfamily C, member 2 | SCYC2 | 1q23–q25 | Cytokines, chemokines and other ligands |

TABLE 1-continued

| Probe_ID | RL3_Signal Log Ratio | RL4_Signal Log Ratio | Accession | Gene name | Gene symbol | Locus | Functional group |
|---|---|---|---|---|---|---|---|
| 33541_s_at | −1.8 | −1.71 | AA133246 | leukocyte-associated Ig-like receptor 2 | LAIR2 | 19q13.4 | Cell surface molecule |
| 31540_s_at | −2.1 | −1.51 | U03397 | tumor necrosis factor receptor superfamily, member 9 | TNFRSF9 | 1p36 | Cell surface molecule |

Summary of data on target genes of IL-4 at 48 h in human CD4+ T cells (Th2-induced vs activated)

| Probe_ID | RL3_Signal Log Ratio | RL4_Signal Log Ratio | Accession | Gene name | Gene symbol | Locus | Functional group |
|---|---|---|---|---|---|---|---|
| 37137_at | 2.73 | 4.14 | M17016 | granzyme B (granzyme 2, cytotoxic T-lymphocyte-associated serine esterase 1) | GZMB | 14q11.2 | Enzymes and other pathway molecules |
| 41504_s_at | 2.82 | 3.49 | AF055376 | v-maf musculoaponeurotic fibrosarcoma (avian) oncogene homolog | MAF | 16q22-q23 | Transcriptional regulator |
| 1892_s_at | 2.90 | 3.36 | HG1437-HT1437 | neurotrophic tyrosine kinase, receptor, type 1 | Trk | 1q21-q22 | Cell surface molecule |
| 41193_at | 2.52 | 3.71 | AB013382 | dual specificity phosphatase 6 | DUSP6 | 12q22-q23 | Enzymes and other pathway molecules |
| 34439_at | 2.58 | 3.39 | AF024714 | absent in melanoma 2 | AIM2 | 1q22 | Enzymes and other pathway molecules |
| 1069_at | 4.33 | 1.11 | U04636 | cyclooxygenase-2 | Cox-2 | 1q25.2-q25.3 | Enzymes and other pathway molecules |
| 41592_at | 2.70 | 2.45 | AB000734 | JAK binding protein | SSI-1 | 16p13.13 | Enzymes and other pathway molecules |
| 37038_at | 2.63 | 2.48 | X83467 | peroxisomal membrane protein-1 | PXMP1 | 1p22-p21 | Structural and intracellular trafficking molecules |
| 41505_r_at | 2.54 | 2.56 | AF055376 | v-maf musculoaponeurotic fibrosarcoma (avian) oncogene homolog | MAF | 16q22-q23 | Transcriptional regulator |
| 35938_at | 3.70 | 1.30 | M72393 | phospholipase A2, group IVA (cytosolic, calcium-dependent) | PLA2G4A | 1q25 | Enzymes and other pathway molecules |
| 37544_at | 2.34 | 2.54 | X64318 | nuclear factor, interleukin 3 regulated | NFIL3 | 9q22 | Transcriptional regulator |
| 40511_at | 2.53 | 2.04 | X58072 | GATA-binding protein 3 | GATA3 | 10p15 | Transcriptional regulator |
| 36805_s_at | 1.58 | 2.91 | X03541 | neurotrophic tyrosine kinase, receptor, type 1 | NTRK1 | 1q21-q22 | Cell surface molecule |
| 931_at | 2.63 | 1.85 | L08177 | Epstein-Barr virus induced gene 2 (lymphocyte-specific G protein-coupled receptor) | EBI2 | 13q32.3 | Cell surface molecule |
| 41772_at | 2.16 | 1.93 | M68840 | monoamine oxidase A | MAOA | Xp11.4-p11.3 | Enzymes and other pathway molecules |
| 1368_at | 1.92 | 1.99 | M27492 | interleukin 1 receptor, type I | IL1R1 | 2q12 | Cell surface molecule |
| 34678_at | 1.81 | 1.98 | AL096713 | fer-1-like 3, myoferlin | FER1L3 | 10q24 | Unclassified |
| 37121_at | 2.47 | 1.18 | S69115 | natural killer cell group 7 sequence | NKG7 | 19q13.41 | Cell surface molecule |
| 36899_at | 1.49 | 2.02 | M97287 | special AT-rich sequence binding protein 1 (binds to nuclear matrix/scaffold-associating DNA's) | SATB1 | 3p23 | Structural and intracellular trafficking molecules |
| 39942_at | 1.37 | 2.03 | AF016898 | basic leucine zipper transcription factor, ATF-like | B-ATF | 14q24.3 | Transcriptional regulator |
| 38336_at | 1.60 | 1.71 | AB023230 | KIAA1013 protein | KIAA1013 | 3 | Unclassified |
| 41215_s_at | 1.56 | 1.34 | D13891 | inhibitor of DNA binding 2, dominant negative helix-loop-helix protein | ID2 | 2p25 | Enzymes and other pathway molecules |
| 1062_g_at | 1.70 | 1.16 | U00672 | interleukin 10 receptor, alpha | IL10RA | 11q23 | Cell surface molecule |
| 33305_at | 1.20 | 1.58 | M93056 | serine (or cysteine) proteinase inhibitor, clade B (ovalbumin), member 1 | SERPINB1 | 6p25 | Enzymes and other pathway molecules |
| 40848_g_at | 1.25 | 1.36 | AB018293 | KIAA0750 gene product | KIAA0750 | 11p15.3 | Unclassified |

TABLE 1-continued

| Probe_ID | RL3_Signal Log Ratio | RL4_Signal Log Ratio | Accession | Gene name | Gene symbol | Locus | Functional group |
|---|---|---|---|---|---|---|---|
| 37524_at | 1.09 | 1.44 | AB011421 | serine/threonine kinase 17b (apoptosis-inducing) | STK17B | 2q33.1 | Enzymes and other pathway molecules |
| 34517_at | 1.16 | 1.36 | X66435 | 3-hydroxy-3-methylglutaryl-Coenzyme A synthase 1 (soluble) | HMGCS1 | 5p14-p13 | Enzymes and other pathway molecules |
| 34348_at | 1.33 | 1.12 | U78095 | serine protease inhibitor, Kunitz type, 2 | SPINT2 | 19q13.1 | Enzymes and other pathway molecules |
| 40448_at | 1.02 | 1.26 | M92843 | zinc finger protein 36, C3H type, homolog (mouse) | ZFP36 | 19q13.1 | Enzymes and other pathway molecules |
| 37732_at | 1.11 | 1.16 | AL049940 | AU RNA-binding protein/enoyl-Coenzyme A hydratase | AUH | 9q22.1 | Unclassified |
| 37616_at | 1.16 | 1.05 | X79888 |  |  |  | Enzymes and other pathway molecules |
| 2002_s_at | 1.01 | 1.03 | U27467 | BCL2-related protein A1 | BCL2A1 | 15q24.3 | Enzymes and other pathway molecules |
| 37842_at | -1.02 | -1.01 | AF054589 | I-mfa domain-containing protein | HIC | 7q31.33 | Unclassified |
| 37536_at | -1.17 | -1.10 | Z11697 | CD83 antigen (activated B lymphocytes, immunoglobulin superfamily) | CD83 | 6p23 | Cell surface molecule |
| 35735_at | -1.18 | -1.32 | M55542 | guanylate binding protein 1, interferon-inducible, 67 kD | GBP1 | 1p22.1 | Unclassified |
| 32859_at | -1.27 | -1.29 | M97935 | signal transducer and activator of transcription 1, 91 kD | STAT1 | 2q32.2 | Transcriptional regulator |
| 33705_at | -1.43 | -1.37 | L20971 | phosphodiesterase 4B, cAMP-specific (dunce (Drosophila)-homolog phosphodiesterase E4) | PDE4B | 1p31 | Enzymes and other pathway molecules |
| 33339_g_at | -1.04 | -2.02 | M97936 | signal transducer and activator of transcription 1 | ISGF3 | 2q32.2 | Transcriptional regulator |
| 38575_at | -1.16 | -2.00 | AF070528 |  | ISGF3 | 2q32.2 | Unclassified |
| 33338_at | -1.28 | -2.07 | M97936 | signal transducer and activator of transcription 1 |  |  | Transcriptional regulator |
| 37623_at | -1.74 | -1.74 | X75918 | nuclear receptor subfamily 4, group A, member 2 | NR4A2 | 2q22-q23 | Transcriptional regulator |
| 40729_s_at | -2.36 | -1.13 | Y14768 | lymphotoxin beta (TNF superfamily, member 3) | LTB | 6p21.3 | Cytokines, chemokines and other ligands |
| 37014_at | -1.02 | -2.62 | M33882 | myxovirus (influenza) resistance 1, homolog of murine (interferon-inducible protein p78) | MX1 | 21q22.3 | Enzymes and other pathway molecules |
| 38326_at | -2.13 | -1.74 | M69199 | putative lymphocyte G0/G1 switch gene | G0S2 | 1 | Enzymes and other pathway molecules |
| 547_s_at | -2.07 | -2.34 | S77154 | nuclear receptor subfamily 4, group A, member 2 | NR4A2 | 2q22-q23 | Transcriptional regulator |

Summary of data on genes differentially expressed at 48 h when gene expression of human CD4+ T cells induced to Th1 direction is compared to gene expression of human CD4+ T cells induced to Th2 direction.

| Probe_ID | RL3_Signal Log Ratio | RL4_Signal Log Ratio | Accession | Gene name | Gene symbol | Locus | Functional group |
|---|---|---|---|---|---|---|---|
| 40702_at | 6.35 | 7.35 | X13274 | interferon, gamma | IFNG | 12q14 | Cytokines, chemokines and other ligands |
| 33093_at | 4.31 | 4.09 | AF077346 | interleukin 18 receptor accessory protein | IL18RAP | 2p24.3-p24.1 | Cell surface molecule |
| 1021_at | 6.16 | 5.06 | J00219 | interferon, gamma | IFNG | 12q14 | Cytokines, chemokines and other ligands |
| 1611_s_at | 5.03 | 3.34 | J00219 | interferon, gamma | IFNG | 12q14 | Cytokines, chemokines and other ligands |

TABLE 1-continued

| Probe | Val1 | Val2 | Accession | Description | Gene | Locus | Category |
|---|---|---|---|---|---|---|---|
| 38326_at | 3.50 | 3.31 | M69199 | putative lymphocyte G0/G1 switch gene | G0S2 | 1 | Enzymes and other pathway molecules |
| 31792_at | 3.76 | | | annexin A3 | ANXA3 | 4q13-q22 | Enzymes and other pathway molecules |
| 39264_at | 1.84 | 1.43 | M20560 | 2'-5'-oligoadenylate synthetase 2 (69–71 kD) | OAS2 | 12q24.2 | Enzymes and other pathway molecules |
| 34021_at | 1.43 | 2.15 | M87284 | interleukin 2 | IL2 | 4q26-q27 | Cytokines, chemokines and other ligands |
| 32370_at | 1.95 | 2.21 | S82692 | cytotoxic T-lymphocyte-associated serine esterase 1 | CTLA1 | 14q11.2 | Enzymes and other pathway molecules |
| 31961_r_at | 1.46 | 1.38 | M57888 | adenosine monophosphate deaminase (isoform E) | AMPD3 | 3q27.1 | Unclassified |
| 38463_s_at | 1.13 | 1.54 | AF070579 | | | 11p15 | Enzymes and other pathway molecules |
| | | 1.46 | U29926 | | | | |
| 1538_s_at | 1.36 | 4.36 | X00695 | interleukin 2 | IL2 | 4q26-q27 | Cytokines, chemokines and other ligands |
| 34607_at | 1.14 | 1.20 | AB023135 | inducible T-cell co-stimulator | ICOS | 2q33 | Cell surface molecule |
| 40396_at | 1.03 | 1.29 | U49395 | purinergic receptor P2X, ligand-gated ion channel, 5 | P2RX5 | 17p13 | Structural and intracellular rafficking molecules |
| 1004_at | 1.13 | 1.02 | X68149 | Burkitt lymphoma receptor 1, GTP-binding protein | BLR1 | 11q23.3 | Cell surface molecule |
| 441_s_at | 1.05 | 1.01 | X13967 | leukemia inhibitory factor (cholinergic differentiation factor) | LIF | 22q12.2 | Cell surface molecule |
| 34678_at | -1.01 | -1.15 | AL096713 | fer-1-like 3, myoferlin | FER1L3 | 10q24 | Unclassified |
| 35712_at | -1.00 | -1.40 | AC004142 | leucine-rich repeat protein, neuronal 3 | LRRN3 | 7q22.3 | Unclassified |
| 34091_s_at | -1.44 | -1.02 | Z19554 | vimentin | VIM | 10p13 | Structural and intracellular rafficking molecules |
| 40456_at | -1.46 | -1.00 | AL049963 | leukocyte-associated Ig-like receptor 2 | LAIR2 | 19q13.4 | Unclassified |
| 33541_s_at | -1.35 | -1.17 | AA133246 | special AT-rich sequence binding protein 1 (binds to nuclear matrix/scaffold-associating DNA's) | SATB1 | 3p23 | Cell surface molecule |
| 36899_at | -1.34 | -1.25 | M97287 | | | | Structural and intracellular rafficking molecules |
| 36926_at | -1.59 | -1.12 | X80692 | mitogen-activated protein kinase 6 | MAPK6 | 15q21 | Enzymes and other pathway molecules |
| 649_s_at | -1.47 | -1.44 | L06797 | chemokine (C—X—C motif), receptor 4 (fusin) | CXCR4 | 2q21 | Cell surface molecule |
| 38685_at | -1.81 | -1.11 | AL035306 | hypothetical protein MGC14797 | MGC14797 | Xq26 | Unclassified |
| 34348_at | -1.98 | -1.20 | U78095 | serine protease inhibitor, Kunitz type, 2 | SPINT2 | 19q13.1 | Enzymes and other pathway molecules |
| 40049_at | -1.01 | -2.18 | X76104 | death-associated protein kinase 1 | DAPK1 | 9q34.1 | Enzymes and other pathway molecules |
| 37544_at | -1.69 | -1.53 | X64318 | nuclear factor, interleukin 3 regulated | NFIL3 | 9q22 | Transcriptional regulator |
| 39331_at | -1.00 | -2.37 | X79535 | tubulin, beta polypeptide | TUBB | 6p21.3 | Structural and intracellular rafficking molecules |
| 1061_at | -1.51 | -1.02 | U00672 | interleukin 10 receptor, alpha | IL10RA | 11q23 | Cell surface molecule |
| 31856_at | -2.42 | -1.25 | Z24680 | glycoprotein A repetitions predominant | GARP | 11q13.5-q14 | Cell surface molecule |
| 931_at | -1.49 | -2.36 | L08177 | Epstein-Barr virus induced gene 2 (lymphocyte-specific G protein-coupled receptor) | EBI2 | 13q32.3 | Cell surface molecule |

TABLE 1-continued

| Probe_ID | RL3_Signal Log Ratio | MAS5RL4_Signal Log Ratio | Accession | Gene name | Gene symbol | Locus | Functional group |
|---|---|---|---|---|---|---|---|
| 41504_s_at | -1.17 | -2.86 | AF055376 | v-maf musculoaponeurotic fibrosarcoma (avian) oncogene homolog | MAF | 16q22-q23 | Transcriptional regulator |
| 41193_at | -1.13 | -2.93 | AB013382 | dual specificity phosphatase 6 | DUSP6 | 12q22-q23 | Enzymes and other pathway molecules |
| 494_at | -1.85 | -2.36 | U31120 | interleukin 13 | IL-13 | 5q31 | Cytokines, chemokines and other ligands |
| 1069_at | -1.70 | -2.80 | U04636 | cyclooxygenase-2 | Cox-2 | cyclooxygenase-2 | Enzymes and other pathway molecules |
| 33809_at | -3.40 | -1.19 | AL049933 | guanine nucleotide binding protein (G protein), alpha inhibiting activity polypeptide 1 | GNAI1 | 7q21 | Cell surface molecule |
| 1062_g_at | -2.79 | -1.98 | U00672 | interleukin 10 receptor, alpha | IL10RA | 11q23 | Cell surface molecule |
| 37038_at | -2.33 | -2.67 | X83467 | peroxisomal membrane protein-1 | PXMP1 | 1p22-p21 | Structural and intracellular rafficking molecules |
| 41592_at | -3.68 | -2.03 | AB000734 | JAK binding protein | SSI-1 | 16p13.13 | Enzymes and other pathway molecules |
| 36805_s_at | -2.85 | -3.21 | X03541 | neurotrophic tyrosine kinase, receptor, type 1 | NTRK1 | 1q21-q22 | Cell surface molecule |
| 1892_s_at | -3.26 | -3.96 | HG1437-HT1437 | neurotrophic tyrosine kinase, receptor, type 1 | Trk | 1q21-q22 | Cell surface molecule |
| 40511_at | -3.68 | -2.59 | X58072 | GATA-binding protein 3 | GATA3 | 10p15 | Transcriptional regulator |
| 35938_at | -2.99 | -3.80 | M72393 | phospholipase A2, group IVA (cytosolic, calcium-dependent) | PLA2G4A | 1q25 | Enzymes and other pathway molecules |
| 41772_at | -4.00 | -2.94 | M68840 | monoamine oxidase A | MAOA | Xp11.4-p11.3 | Enzymes and other pathway molecules |

Summary of data on genes differentially expressed at 48 h when gene expression of human CD4+ T cells induced to Th1 direction and treated with TGFb is compared to gene expression of human CD4+ T cells induced to Th1 direction.

| Probe_ID | RL3_Signal Log Ratio | MAS5RL4_Signal Log Ratio | Accession | Gene name | Gene symbol | Locus | Functional group |
|---|---|---|---|---|---|---|---|
| 1405_i_at | 3.78 | 3.35 | M21121 | small inducible cytokine A5 (RANTES) | SCYA5 | 17q11.2-q12 | Cytokines, chemokines and other ligands |
| 1403_s_at | 2.11 | 3.73 | M21121 | small inducible cytokine A5 (RANTES) | SCYA5 | 17q11.2-q12 | Cytokines, chemokines and other ligands |
| 40385_at | 2.03 | 2.55 | U64197 | small inducible cytokine subfamily A (Cys-Cys), member 20 | SCYA20 | 2q33-q37 | Cytokines, chemokines and other ligands |
| 34091_s_at | 2.61 | 1.73 | Z19554 | vimentin | VIM | 10p13 | Structural and intracellular rafficking molecules |
| 38391_at | 1.14 | 3.04 | M94345 | capping protein (actin filament), gelsolin-like | CAPG | 2cen-q24 | Structural and intracellular rafficking molecules |
| 41209_at | 1.80 | 2.30 | M15856 | lipoprotein lipase | LPL | 8p22 | Enzymes and other pathway molecules |
| 41472_at | 1.76 | 2.15 | AL078641 | phorbolin-like protein MDS019 | MDS019 | 22q | Unclassified |
| 37669_s_at | 1.62 | 2.27 | U16799 | ATPase, Na+/K+ transporting, beta 1 polypeptide | ATP1B1 | 1q22-q25 | Structural and intracellular rafficking molecules |

TABLE 1-continued

| Probe_ID | RL3_Signal Log Ratio | RL4_Signal Log Ratio | Accession | Gene name | Gene symbol | Locus | Functional group |
|---|---|---|---|---|---|---|---|
| 1788_s_at | 2.34 | 1.49 | U48807 | dual specificity phosphatase 4 | DUSP4 | 8p12-p11 | Enzymes and other pathway molecules |
| 34947_at | 1.57 | 1.87 | AA442560 | phorbolin-like protein MDS019 | MDS019 | 22q | Unclassified |
| 32607_at | 1.38 | 1.85 | AF039656 | brain abundant, membrane attached signal protein 1 | BASP1 | 5p15.1-p14 | Enzymes and other pathway molecules |
| 31540_at | 1.37 | 1.80 | U03397 | tumor necrosis factor receptor superfamily, member 9 | TNFRSF9 | 1p36 | Cell surface molecule |
| 33232_at | 1.53 | 1.33 | AI017574 | cysteine-rich protein 1 (intestinal) | CRIP1 | 7q11.23 | Unclassified |
| 40662_g_at | 1.00 | 1.70 | D78579 | nuclear receptor subfamily 4, group A, member 3 | NR4A3 | 9q22 | Unclassified |
| 2069_s_at | 1.18 | 1.46 | L23805 | catenin (cadherin-associated protein), alpha 1 (102 Kd) | CTNNA1 | 5q31 | Cell surface molecule |
| 41779_at | 1.13 | 1.51 | U70426 | regulator of G-protein rafficki 16 | RGS16 | 1q25-q31 | Cell surface molecule |
| 769_s_at | 1.28 | 1.28 | D00017 | annexin A2 | ANXA2 | 15q21-q22 | Enzymes and other pathway molecules |
| 1358_s_at | 1.02 | 1.27 | U22970 | interferon, alpha-inducible protein | G1P3 | 1p35 | Unclassified |
| 33412_at | 1.01 | 1.25 | AI535946 | lectin, galactoside-binding, soluble, 1 (galectin 1) | LGALS1 | 22q13.1 | Enzymes and other pathway molecules |
| 31444_s_at | 1.10 | 1.08 | M62895 | annexin A2 pseudogene 3 | ANXA2P3 | 10q21-q22 | Unclassified |
| 40365_at | -1.09 | -1.08 | M63904 | guanine nucleotide binding protein (G protein), alpha 15 (Gq class) | GNA15 | 19p13.3 | Cell surface molecule |
| 36545_s_at | -1.12 | -1.15 | AB011114 | KIAA0542 gene product | KIAA0542 | 22q12.2 | Unclassified |
| 37137_at | -1.53 | -1.24 | M17016 | granzyme B (granzyme 2, cytotoxic T-lymphocyte-associated serine esterase 1) | GZMB | 14q11.2 | Enzymes and other pathway molecules |
| 37544_at | -1.75 | -1.68 | X64318 | nuclear factor, interleukin 3 regulated | NFIL3 | 9q22 | Transcriptional regulator |
| 33285_i_at | -2.54 | -1.00 | W26762 | hypothetical protein FLJ21168 | FLJ21168 | 1p11.1 | Unclassified |
| 36899_at | -1.82 | -1.78 | M97287 | special AT-rich sequence binding protein 1 (binds to nuclear matrix/scaffold-associating DNA's) | SATB1 | 3p23 | Structural and intracellular rafficking molecules |
| 38944_at | -2.55 | -3.13 | U68019 | MAD (mothers against decapentaplegic, Drosophila) homolog 3 | MADH3 | 15q21-q22 | Transcriptional regulator |

Summary of data on genes differentially expressed at 48 h when gene expression of human CD4+ T cells induced to Th2 direction and treated with TGFb is compared to gene expression of human CD4+ T cells induced to Th2 direction.

| Probe_ID | RL3_Signal Log Ratio | RL4_Signal Log Ratio | Accession | Gene name | Gene symbol | Locus | Functional group |
|---|---|---|---|---|---|---|---|
| 37669_s_at | 3.04 | 4.00 | U16799 | ATPase, Na+/K+ transporting, beta 1 polypeptide | ATP1B1 | 1q22-q25 | Structural and intracellular trafficing molecules |
| 11183_at | 1.83 | 4.84 | D43767 | small inducible cytokine subfamily A (Cys-Cys), member 17 | SCYA17 | 16q13 | Cytokines, chemokines and other ligands |
| 1405_i_at | 2.26 | 3.91 | M21121 | small inducible cytokine A5 (RANTES) | SCYA5 | 17q11.2-q12 | Cytokines, chemokines and other ligands |
| 977_s_at | 3.75 | 2.28 | Z35402 | cadherin 1, type 1, E-cadherin | ECAD3 | 16q22.1 | Cell surface molecule |
| 35367_at | 1.98 | 3.13 | AB006780 | lectin, galactoside-binding, soluble, 3 (galectin 3) | LGALS3 | 14q21-q22 | Enzymes and other pathway molecules |
| 1403_s_at | 2.01 | 2.87 | M21121 | small inducible cytokine A5 (RANTES) | SCYA5 | 17q11.2-q12 | Cytokines, chemokines and other ligands |
| 32607_at | 2.09 | 2.01 | AF039656 | brain abundant, membrane attached signal protein 1 | BASP1 | 5p15.1-p14 | Enzymes and other pathway molecules |
| 34037_at | 1.91 | 1.98 | M30134 | interleukin 9 | IL9 | 5q31.1 | Cytokines, chemokines |

TABLE 1-continued

| | | | | | | |
|---|---|---|---|---|---|---|
| 35824_at | 1.74 | | AJ223321 | zinc finger protein 238 | ZNF238 | 1q44-qter | and other ligands<br>Transcriptional regulator |
| 36575_at | 2.06 | 2.04 | S59049 | regulator of G-protein signalling 1 | RGS1 | 1q31 | Cell surface molecule |
| 36117_at | 2.17 | 1.70 | L13616 | PTK2 protein tyrosine kinase 2 | PTK2 | 8q24-qter | Enzymes and other pathway molecules |
| 34739_at | 1.37 | 1.46 | W26023 | hypothetical protein FLJ20275 | FLJ20275 | 1p21.3 | Unclassified |
| 37603_at | 1.42 | 2.20 | X52015 | interleukin 1 receptor antagonist | IL1RN | 2q14.2 | Cytokines, chemokines and other ligands |
| 39248_at | 1.85 | 1.98 | N74607 | aquaporin 3 | AQP3 | 9p13 | Structural and intracellular trafficing molecules |
| 34217_at | 1.08 | 1.45 | AB015132 | Kruppel-like factor 7 (ubiquitous) | KLF7 | 2q32 | Transcriptional regulator |
| 37377_i_at | 1.22 | 1.52 | M13452 | lamin A/C | LMNA | 1q21.2-q21.3 | Structural and intracellular trafficing molecules |
| 40818_at | 1.15 | 1.35 | D14041 | H-2K binding factor-2 | LOC51580 | 9 | Transcriptional regulator |
| 37391_at | 1.07 | 1.32 | X12451 | cathepsin L | CTSL | 9q21-q22 | Unclassified |
| 32587_at | 1.18 | 1.14 | U07802 | zinc finger protein 36, C3H type-like 2 | ZFP36L2 | 2p22.3-p21 | Transcriptional regulator |
| 32778_at | −1.10 | −1.06 | D26070 | inositol 1,4,5-triphosphate receptor, type 1 | ITPR1 | 3p26-p25 | Structural and intracellular trafficing molecules |
| 38006_at | −1.15 | −1.06 | M37766 | CD48 antigen (B-cell membrane protein) | CD48 | 1q21.3-q22 | Cell surface molecule |
| 41215_s_at | −1.11 | −1.14 | D13891 | inhibitor of DNA binding 2, dominant negative helix-loop-helix protein | ID2 | 2p25 | Enzymes and other pathway molecules |
| 33849_at | −1.06 | −1.35 | U02020 | pre-B-cell colony-enhancing factor | PBEF | 7q22.1 | Cytokines, chemokines and other ligands |
| 34801_at | −1.33 | −1.25 | AB014610 | KIAA0710 gene product | KIAA0710 | 12q13.2-q13.3 | Unclassified |
| 34098_f_at | −1.38 | −1.22 | AI799757 | integrin cytoplasmic domain-associated protein 1 | ICAP-1A | 2p25.2 | Cell surface molecule |
| 36377_at | −1.44 | −1.18 | U43672 | interleukin 18 receptor 1 | IL18R1 | 2q12 | Cell surface molecule |
| 1069_at | −1.12 | −1.51 | U04636 | cyclooxygenase-2 | Cox-2 | 1q25.2-q25.3 | Enzymes and other pathway molecules |
| 38122_at | −1.49 | −1.23 | D87075 | solute carrier family 23 (nucleobase transporters), member 1 | SLC23A1 | 20p13 | Structural and intracellular trafficing molecules |
| 35943_s_at | −1.13 | −1.88 | D13317 | GA-binding protein transcription factor, beta subunit 1 (53 kD) | GABPB1 | 7q11.2 | Transcriptional regulator |
| 2002_s_at | −1.29 | −1.75 | U27467 | BCL2-related protein A1 | BCL2A1 | 15q24.3 | Cytokines, chemokines and other ligands |
| 33809_at | −1.15 | −1.97 | AL049933 | guanine nucleotide binding protein (G protein), alpha inhibiting activity polypeptide 1 | GNAI1 | 7q21 | Cell surface molecule |
| 34965_at | −1.54 | −1.59 | AF031824 | cystatin F (leukocystatin) | CST7 | 20p11.22-p11.21 | Enzymes and other pathway molecules |
| 37544_at | −1.23 | −1.95 | X64318 | nuclear factor, interleukin 3 regulated | NFIL3 | 9q22 | Transcriptional regulator |
| 36160_s_at | −1.27 | −2.04 | U81561 | protein tyrosine phosphatase, receptor type, N polypeptide 2 | PTPRN2 | 7q36 | Enzymes and other pathway molecules |
| 35938_at | −1.15 | −2.86 | M72393 | phospholipase A2, group IVA (cytosolic, calcium-dependent) | PLA2G4A | 1q25 | Enzymes and other pathway molecules |

*Gene was classified to be "not changed" by Affymetrix MAS5 software in either one or in both biological replicates.

TABLE 2

| TIME | AFFY PROBE ID | GENE NAME | SYMBOL | ACCESSION | FOLD CHANGE |
|---|---|---|---|---|---|
| | | Novel target genes of IL-12 in human CD4+ T cells (Th1-induced vs activated) | | | |
| 2 h | 32417_at | desmocollin 3 | DSC3 | D17427 | 2.8 |
| | 39718_r_at | mitochondrial ribosomal protein L33 | MRPL33 | N98607 | −4.0 |
| 48 h | 40635_at | flotillin 1 | FLOT1 | AF089750 | 2.5 |
| | 34654_at | myotubularin related protein 1 | MTMR1 | AJ224979 | 2.1 |
| | 38620_at | golgi SNAP receptor complex member 2 | GOSR2 | AA905543 | −2.3 |
| | 34866_at | | . | AF055029 | −2.8 |
| | 31856_at | glycoprotein A repetitions predominant | GARP | Z24680 | −2.9 |
| | 39582_at | | . | AL050166 | −2.9 |
| | 38575_at | | MALT1 | AF070528 | −3.0 |
| | 33541_s_at | leukocyte-associated Ig-like receptor 2 | LAIR2 | AA133246 | −3.4 |
| | | Novel target genes of IL-4 in human CD4+ T cells (Th2-induced vs activated)) | | | |
| 2 h | 38549_at | Vipirin | cig5 | AF026941 | 13.5 |
| | 34757_at | ADP-ribosyltransferase (NAD+; poly(ADP-ribose) polymerase)-like 2 | ADPRTL2 | AA595596 | 4.6 |
| | 41193_at | dual specificity phosphatase 6 | DUSP6 | AB013382 | 4.0 |
| | 39593_at | *Homo sapiens*, Similar to fibrinogen-like 2, clone MGC: 22391 IMAGE: 4616866, mRNA, complete cds | . | AI432401 | 3.9 |
| | 38149_at | KIAA0053 gene product | KIAA0053 | D29642 | 3.3 |
| | 35712_at | leucine-rich repeat protein, neuronal 3 | LRRN3 | AC004142 | 3.0 |
| | 33047_at | ESTs, Weakly similar to B34087 hypothetical protein [*H. sapiens*] | . | AI971169 | 2.9 |
| | 38051_at | mal, T-cell differentiation protein | MAL | X76220 | 2.7 |
| | 36736_f_at | phosphoserine phosphatase | PSPH | Y10275 | 2.5 |
| | 35320_at | solute carrier family 11 (proton-coupled divalent metal ion transporters), member 2 | SLC11A2 | AB004857 | 2.3 |
| | 36899_at | special AT-rich sequence binding protein 1 (binds to nuclear matrix/scaffold-associating DNA's) | SATB1 | M97287 | 2.3 |
| | 725_i_at | Chorionic Somatomammotropin Hormone Cs-5 | | HG1751–HT1768 | 2.3 |
| | 41145_at | KIAA0914 gene product | KIAA0914 | AB020721 | 2.1 |
| | 39827_at | HIF-1 responsive RTP801 | RTP801 | AA522530 | −2.1 |
| | 41475_at | ninjurin 1 | NINJ1 | U91512 | −2.3 |
| | 33997_at | *Homo sapiens* mRNA; cDNA DKFZp586B1722 (from clone DKFZp586B1722) | . | AL049449 | −2.8 |
| | 37043_at | inhibitor of DNA binding 3, dominant negative helix-loop-helix protein | ID3 | AL021154 | −2.8 |
| 6 h | 41193_at | dual specificity phosphatase 6 | DUSP6 | AB013382 | 8.6 |
| | 38549_at | Vipirin | cig5 | AF026941 | 7.7 |
| | 34348_at | serine protease inhibitor, Kunitz type, 2 | SPINT2 | U78095 | 6.7 |
| | 39330_s_at | actinin, alpha 1 | ACTN1 | M95178 | 3.9 |
| | 34173_s_at | contactin 5 | CNTN5 | AB013802 | 3.4 |
| | 34319_at | S100 calcium binding protein P | S100P | AA131149 | 3.1 |
| | 37038_at | ATP-binding cassette, sub-family D (ALD), member 3 | ABCD3 | X83467 | 3.0 |
| | 40839_at | ubiquitin-like 3 | UBL3 | AL080177 | 2.7 |
| | 33352_at | H2B histone family, member Q | H2BFQ | X57985 | 2.6 |
| | 41577_at | protein phosphatase 1, regulatory (inhibitor) subunit 16B | PPP1R16B | AB020630 | 2.5 |
| | 38051_at | mal, T-cell differentiation protein | MAL | X76220 | 2.2 |
| | 34256_at | sialyltransferase 9 (CMP-NeuAc: lactosylceramide alpha-2,3-sialyltransferase; GM3 synthase) | SIAT9 | AB018356 | −2.1 |
| | 41209_at | lipoprotein lipase | LPL | M15856 | −2.3 |
| | 41744_at | Optineurin | OPTN | AF070533 | −2.6 |
| | 32649_at | transcription factor 7 (T-cell specific, HMG-box) | TCF7 | X59871 | −2.6 |
| | 36239_at | POU domain, class 2, associating factor 1 | POU2AF1 | Z49194 | −2.9 |
| | 37043_at | inhibitor of DNA binding 3, dominant negative helix-loop-helix protein | ID3 | AL021154 | −4.4 |
| | 33540_at | *Homo sapiens* mRNA; cDNA DKFZp564A023 (from clone DKFZp564A023) | | AL049233 | −4.6 |
| | 39586_at | Desmoglein 1 | DSG1 | AF097935 | −4.6 |
| 48 h | 41193_at | dual specificity phosphatase 6 | DUSP6 | AB013382 | 8.7 |
| | 34439_at | absent in melanoma 2 | AIM2 | AF024714 | 7.9 |
| | 37038_at | peroxisomal membrane protein-1 | ABCD3 | X83467 | 5.9 |
| | 34678_at | fer-1-like 3, myoferlin | FER1L3 | AL096713 | 3.7 |
| | 36899_at | special AT-rich sequence binding protein 1 (binds to nuclear matrix/scaffold-associating DNA's) | SATB1 | M97287 | 3.4 |
| | 38336_at | KIAA1013 protein | KIAA1013 | AB023230 | 3.2 |
| | 41215_s_at | inhibitor of DNA binding 2, dominant negative helix-loop-helix protein | ID2 | D13891 | 2.7 |
| | 40848_g_at | KIAA0750 gene product | KIAA0750 | AB018293 | 2.5 |
| | 37524_at | serine/threonine kinase 17b (apoptosis-inducing) | STK17B | AB011421 | 2.4 |
| | 34517_at | 3-hydroxy-3-methylglutaryl-Coenzyme A synthase 1 (soluble) | HMGCS1 | X66435 | 2.4 |
| | 34348_at | serine protease inhibitor, Kunitz type, 2 | SPINT2 | U78095 | 2.3 |
| | 40448_at | zinc finger protein 36, C3H type, homolog (mouse) | ZFP36 | M92843 | 2.2 |
| | 37732_at | | RYBP | AL049940 | 2.2 |

TABLE 2-continued

| TIME | AFFY PROBE ID | GENE NAME | SYMBOL | ACCESSION | FOLD CHANGE |
|---|---|---|---|---|---|
| | 37616_at | AU RNA-binding protein/enoyl-Coenzyme A hydratase | AUH | X79888 | 2.2 |
| | 37842_at | I-mfa domain-containing protein | . | AF054589 | −2.0 |
| | 33339_g_at | CD83 antigen (activated B lymphocytes, immunoglobulin superfamily) | CD83 | Z11697 | −2.2 |
| | 38575_at | | MALT1 | AF070528 | −3.0 |
| | colspan="5" | Novel data on genes differentially expressed at 48 h when gene expression of human CD4+ T cells induced to Th1 direction is compared to gene expression of human CD4+ T cells induced to Th2 direction. | | | |
| 2 h | 37043_at | inhibitor of DNA binding 3, dominant negative helix-loop-helix protein | ID3 | AL021154 | 2.6 |
| | 37909_at | laminin, alpha 3 (nicein (150 kD), kalinin (165 kD), BM600 (150 kD), epilegrin) | LAMA3 | L34155 | 2.4 |
| | 36160_s_at | protein tyrosine phosphatase, receptor type, N polypeptide 2 | PTPRN2 | U81561 | 2.3 |
| | 39827_at | HIF-1 responsive RTP801 | RTP801 | AA522530 | 2.1 |
| | 41475_at | ninjurin 1 | NINJ1 | U91512 | 2.0 |
| | 35320_at | solute carrier family 11 (proton-coupled divalent metal ion transporters), member 2 | SLC11A2 | AB004857 | −2.1 |
| | 37524_at | serine/threonine kinase 17b (apoptosis-inducing) | STK17B | AB011421 | −2.2 |
| | 32919_at | Homo sapiens, clone IMAGE: 3625286, mRNA, partial cds | . | AC004010 | −2.3 |
| | 39549_at | hypothetical protein FLJ23138 | FLJ23138 | AI743090 | −2.3 |
| | 33352_at | H2B histone family, member Q | H2BFQ | X57985 | −2.4 |
| | 36899_at | special AT-rich sequence binding protein 1 (binds to nuclear matrix/scaffold-associating DNA's) | SATB1 | M97287 | −2.5 |
| | 38051_at | mal, T-cell differentiation protein | MAL | X76220 | −2.6 |
| | 34348_at | serine protease inhibitor, Kunitz type, 2 | SPINT2 | U78095 | −2.6 |
| | 35712_at | leucine-rich repeat protein, neuronal 3 | LRRN3 | AC004142 | −2.6 |
| | 38149_at | KIAA0053 gene product | KIAA0053 | D29642 | −2.9 |
| | 36435_at | protein phosphatase 1A (formerly 2C), magnesium-dependent, alpha isoform | PPM1A | AF070670 | −3.0 |
| | 32058_at | HNK-1 sulfotransferase | HNK-1ST | AF070594 | −3.0 |
| | 36148_at | amyloid beta (A4) precursor-like protein 1 | APLP1 | U48437 | −3.5 |
| | 41193_at | dual specificity phosphatase 6 | DUSP6 | AB013382 | −3.7 |
| | 33047_at | ESTs, Weakly similar to B34087 hypothetical protein [H. sapiens] | . | AI971169 | −4.0 |
| | 32148_at | FERM, RhoGEF (ARHGEF) and pleckstrin domain protein 1 (chondrocyte-derived) | FARP1 | AI701049 | −4.3 |
| | 39593_at | Homo sapiens, Similar to fibrinogen-like 2, clone MGC: 22391 IMAGE: 4616866, mRNA, complete cds | . | AI432401 | −9.2 |
| | 38549_at | Vipirin | cig5 | AF026941 | −35.5 |
| 6 h | 40757_at | granzyme A (granzyme 1, cytotoxic T-lymphocyte-associated serine esterase 3) | GZMA | M18737 | 3.6 |
| | 32041_r_at | CDC5 cell division cycle 5-like (S. pombe) | CDC5L | AB007892 | 3.5 |
| | 36705_at | protein kinase, AMP-activated, beta 2 non-catalytic subunit | PRKAB2 | AJ224538 | 3.1 |
| | 32649_at | transcription factor 7 (T-cell specific, HMG-box) | TCF7 | X59871 | 2.9 |
| | 36239_at | POU domain, class 2, associating factor 1 | POU2AF1 | Z49194 | 2.7 |
| | 34252_at | hypothetical protein FLJ10342 | FLJ10342 | W28545 | 2.6 |
| | 37485_at | fatty-acid-Coenzyme A ligase, very long-chain 1 | FACVL1 | D88308 | 2.2 |
| | 40698_at | C-type (calcium dependent, carbohydrate-recognition domain) lectin, superfamily member 2 (activation-induced) | CLECSF2 | X96719 | 2.2 |
| | 34256_at | sialyltransferase 9 (CMP-NeuAc: lactosylceramide alpha-2,3-sialyltransferase; GM3 synthase) | SIAT9 | AB018356 | 2.0 |
| | 37025_at | LPS-induced TNF-alpha factor | PIG7 | AL120815 | 2.0 |
| | 38051_at | mal, T-cell differentiation protein | MAL | X76220 | −2.1 |
| | 34319_at | S100 calcium binding protein P | S100P | AA131149 | −2.2 |
| | 37038_at | ATP-binding cassette, sub-family D (ALD), member 3 | ABCD3 | X83467 | −2.4 |
| | 40839_at | ubiquitin-like 3 | UBL3 | AL080177 | −2.4 |
| | 35794_at | KIAA0942 protein | KIAA0942 | AB023159 | −2.5 |
| | 39330_s_at | actinin, alpha 1 | ACTN1 | M95178 | −2.6 |
| | 35422_at | microtubule-associated protein 2 | MAP2 | U01828 | −3.6 |
| | 34990_at | SET binding protein 1 | SETBP1 | AB022660 | −4.4 |
| | 34348_at | serine protease inhibitor, Kunitz type, 2 | SPINT2 | U78095 | −5.9 |
| | 38549_at | Vipirin | cig5 | AF026941 | −6.1 |
| | 41193_at | dual specificity phosphatase 6 | DUSP6 | AB013382 | −6.7 |
| 48 h | 39264_at | 2'-5'-oligoadenylate synthetase 2 (69–71 kD) | OAS2 | M87284 | 4.0 |
| | 31961_r_at | | . | AF070579 | 2.8 |
| | 34678_at | fer-1-like 3, myoferlin | FER1L3 | AL096713 | −2.1 |
| | 35712_at | leucine-rich repeat protein, neuronal 3 | LRRN3 | AC004142 | −2.3 |
| | 33541_s_at | leukocyte-associated Ig-like receptor 2 | LAIR2 | AA133246 | −2.4 |
| | 36899_at | special AT-rich sequence binding protein 1 (binds to nuclear matrix/scaffold-associating DNA's) | SATB1 | M97287 | −2.5 |
| | 38685_at | hypothetical protein MGC14797 | MGC14797 | AL035306 | −2.8 |
| | 34348_at | serine protease inhibitor, Kunitz type, 2 | SPINT2 | U78095 | −3.0 |

TABLE 2-continued

| TIME | AFFY PROBE ID | GENE NAME | SYMBOL | ACCESSION | FOLD CHANGE |
|---|---|---|---|---|---|
| | 40049_at | death-associated protein kinase 1 | DAPK1 | X76104 | −3.0 |
| | 31856_at | glycoprotein A repetitions predominant | GARP | Z24680 | −3.6 |
| | 41193_at | dual specificity phosphatase 6 | DUSP6 | AB013382 | −4.1 |
| | 37038_at | peroxisomal membrane protein-1 | ABCD3 | X83467 | −5.7 |

TABLE 3

| TIME | AFFY PROBE ID | GENE NAME | SYMBOL | ACCESSION | FOLD CHANGE |
|---|---|---|---|---|---|
| | | Target genes of IL-4 in murine CD4+ T cells (Th2-induced vs activated) | | | |
| 2 h | 103841_at | zinc finger protein 64 | Zfp64 | U49046 | −3.5 |
| | 96623_at | UDP-glucose ceramide glucosyltransferase-like | Ugcgl | AI853172 | −2.3 |
| | 102281_at | tumor necrosis factor receptor superfamily, member 7 | Tnfrsf7 | L24495 | −2.4 |
| | 160273_at | zinc finger protein 36, C3H type-like 2 | Zfp36l2 | AA960603 | −2.3 |
| | 92368_at | receptor (calcitonin) activity modifying protein 3 | Ramp3 | AJ250491 | −2.2 |
| | 98478_at | cyclin G2 | Ccng2 | U95826 | −2.1 |
| | 98072_r_at | deoxycytidine kinase | Dck | X77731 | −2.0 |
| | 104371_at | diacylglycerol O-acyltransferase 1 | Dgat1 | AF078752 | −1.9 |
| | 102797_at | retinal short-chain dehydrogenase/reductase 1 | Rsdr1-pending | X95281 | 2.0 |
| | 160439_at | polymerase, gamma | Polg | U53584 | 2.0 |
| | 96515_at | interleukin-four induced gene 1 | FIG. 1 | U70430 | 1.9 |
| | 104400_at | prenylated SNARE protein | Ykt6-pending | AF076956 | 2.3 |
| | 100606_at | prion protein | Prnp | M18070 | 2.3 |
| | 104449_at | glycine receptor, beta subunit | Glrb | X81202 | 2.2 |
| | 99021_at | paired related homeobox 1 | Prrx1 | U03873 | 2.5 |
| | 102021_at | interleukin 4 receptor, alpha | Il4ra | M27960 | 2.5 |
| | 104155_f_at | activating transcription factor 3 | Atf3 | U19118 | 2.5 |
| | 100022_at | cytokine inducible SH2-containing protein | Cish | D89613 | 2.5 |
| | 99917_at | enhancer of zeste homolog 2 (*Drosophila*) | Ezh2 | U52951 | 2.5 |
| | 97523_i_at | amylase 2, pancreatic | Amy2 | X02578 | 2.6 |
| | 104156_r_at | activating transcription factor 3 | Atf3 | U19118 | 2.8 |
| | 160948_at | protein phosphatase 3, catalytic subunit, gamma isoform | Ppp3cc | M81475 | 2.8 |
| | 98869_g_at | B-cell leukemia/lymphoma 2 | Bcl2 | L31532 | 3.5 |
| | 98868_at | B-cell leukemia/lymphoma 2 | Bcl2 | L31532 | 3.7 |
| | 161411_i_at | lipase, hormone sensitive | Lipe | AV315398 | 8.1 |
| | 161491_r_at | f-box only protein 3 | Fbxo3 | AV083174 | 10.5 |
| | 101920_at | DNA polymerase epsilon, subunit 2 | Pole2 | AF036898 | 15.1 |
| 6 h | 100131_at | secretory granule neuroendocrine protein 1, 7B2 protein | Sgne1 | X15830 | −6.0 |
| | 102157_f_at | immunoglobulin kappa chain variable 28 (V28) | Igk-V28 | M15520 | −4.7 |
| | 161997_f_at | aldehyde dehydrogenase 2, mitochondrial | Aldh2 | AV329607 | −2.9 |
| | 92280_at | actinin, alpha 1 | Actn1 | AA867778 | −2.2 |
| | 92608_at | cysteine rich protein | Csrp | D88793 | −2.1 |
| | 101965_at | ring finger protein 13 | Rnf13 | AF037205 | −2.0 |
| | 92614_at | inhibitor of DNA binding 3 | Idb3 | M60523 | −2.0 |
| | 100022_at | cytokine inducible SH2-containing protein | Cish | D89613 | 2.0 |
| | 96515_at | interleukin-four induced gene 1 | FIG. 1 | U70430 | 2.0 |
| | 98869_g_at | B-cell leukemia/lymphoma 2 | Bcl2 | L31532 | 2.0 |
| | 100924_at | GATA binding protein 3 | Gata3 | X55123 | 2.2 |
| | 104156_r_at | activating transcription factor 3 | Atf3 | U19118 | 2.2 |
| | 102021_at | interleukin 4 receptor, alpha | Il4ra | M27960 | 2.3 |
| | 104155_f_at | activating transcription factor 3 | Atf3 | U19118 | 2.4 |
| | 98868_at | B-cell leukemia/lymphoma 2 | Bcl2 | L31532 | 2.5 |
| | 101913_at | hairy/enhancer-of-split related with YRPW motif 1 | Hey1 | AW214298 | 2.6 |
| | 161051_at | hairy and enhancer of split 5, (*Drosophila*) | Hes5 | D32132 | 2.6 |
| | 160886_i_at | fatty acid binding protein 6, ileal (gastrotropin) | Fabp6 | AV063979 | 3.9 |
| | 100127_at | cellular retinoic acid binding protein II | Crabp2 | M35523 | 5.1 |
| | 104728_at | protein S (alpha) | Pros1 | L27439 | 5.7 |
| 24 h | 160726_at | Quaking | qk | U44940 | −11.4 |
| | 161293_r_at | proteasome (prosome, macropain) 28 subunit, alpha | Psme1 | AV306568 | −10.1 |
| | 94774_at | interferon activated gene 202A | Ifi202a | M31418 | −2.9 |
| | 102424_at | small inducible cytokine A3 | Scya3 | J04491 | −2.6 |
| | 99334_at | interferon gamma | Ifng | K00083 | −2.6 |
| | 161609_at | regulator of G-protein signaling 16 | Rgs16 | AV349152 | −2.5 |
| | 94224_s_at | interferon activated gene 205 | Ifi205 | M74123 | −2.3 |
| | 96060_at | serine (or cysteine) proteinase inhibitor, clade B (ovalbumin), member 6 | Serpinb6 | U25844 | −2.3 |
| | 96592_at | phosphatidylinositol 3-kinase, regulatory subunit, polypeptide 1 (p85 alpha) | Pik3r1 | U50413 | −2.2 |

TABLE 3-continued

| TIME | AFFY PROBE ID | GENE NAME | SYMBOL | ACCESSION | FOLD CHANGE |
|---|---|---|---|---|---|
| | 101851_at | antigen identified by monoclonal antibody MRC OX-2 | Mox2 | AF029215 | −2.1 |
| | 93321_at | interferon activated gene 203 | Ifi203 | AF022371 | −2.1 |
| | 103279_at | SH2 domain protein 1A | Sh2d1a | AF097632 | −2.1 |
| | 161948_f_at | myosin Va | Myo5a | AV214912 | −2.0 |
| | 102630_s_at | lymphotoxin A | Lta | M16819 | −2.0 |
| | 94146_at | small inducible cytokine A4 | Scya4 | X62502 | −2.0 |
| | 102921_s_at | tumor necrosis factor receptor superfamily, member 6 | Tnfrsf6 | M83649 | −2.0 |
| | 102638_at | cystatin F (leukocystatin) | Cst7 | AB015224 | 2.0 |
| | 93871_at | interleukin 1 receptor antagonist | Il1rn | L32838 | 2.0 |
| | 92234_at | retinoid X receptor alpha | Rxra | X66223 | 2.0 |
| | 98282_at | inducible T-cell co-stimulator | Icos | AB023132 | 2.0 |
| | 93092_at | histocompatibility 2, class II, locus DMa | H2-DMa | U35323 | 2.1 |
| | 161012_at | immunoglobulin-associated beta | Igb | J03857 | 2.1 |
| | AFFX-MurIL4_at | interleukin 4 | Il4 | M25892 | 2.1 |
| | 92286_g_at | interleukin 4 | Il4 | AA967539 | 2.1 |
| | 99895_at | chemokine (C—C) receptor 8 | Cmkbr8 | AF001277 | 2.2 |
| | 96515_at | interleukin-four induced gene 1 | FIG. 1 | U70430 | 2.2 |
| | 102995_s_at | granzyme A | Gzma | M13226 | 2.3 |
| | 93444_at | basic leucine zipper transcription factor, ATF-like | Batf | AF017021 | 2.3 |
| | 101902_at | recombining binding protein suppressor of hairless (*Drosophila*) | Rbpsuh | X17459 | 2.5 |
| | 102021_at | interleukin 4 receptor, alpha | Il4ra | M27960 | 3.2 |
| | 93750_at | Gelsolin | Gsn | J04953 | 3.9 |
| | 100924_at | GATA binding protein 3 | Gata3 | X55123 | 4.0 |
| | 103833_at | homeodomain interacting protein kinase 2 | Hipk2 | AF077659 | 4.2 |
| | 94458_at | caspase 6 | Casp6 | Y13087 | 5.2 |
| | 92382_at | myosin VI | Myo6 | U49739 | 5.3 |
| | 104728_at | protein S (alpha) | Pros1 | L27439 | 6.4 |
| 48 h | 93321_at | interferon activated gene 203 | Ifi203 | AF022371 | −6.8 |
| | 104669_at | interferon regulatory factor 7 | Irf7 | U73037 | −5.5 |
| | 103432_at | interferon-stimulated protein (20 kDa) | Isg20 | AW122677 | −5.4 |
| | 93880_at | eomesodermin homolog (*Xenopus laevis*) | Eomes | AB031037 | −5.1 |
| | 100981_at | interferon-induced protein with tetratricopeptide repeats 1 | Ifit1 | U43084 | −4.9 |
| | 94224_s_at | interferon activated gene 205 | Ifi205 | M74123 | −4.9 |
| | 97113_at | tumor necrosis factor (ligand) superfamily, member 6 | Tnfsf6 | U06948 | −4.4 |
| | 103554_at | a disintegrin and metalloproteinase domain 19 (meltrin beta) | Adam19 | AA726223 | −4.3 |
| | 160878_at | block of proliferation 1 | Bop1 | AF061503 | −4.2 |
| | 96060_at | serine (or cysteine) proteinase inhibitor, clade B (ovalbumin), member 6 | Serpinb6 | U25844 | −4.2 |
| | 99334_at | interferon gamma | Ifng | K00083 | −3.9 |
| | 102906_at | T-cell specific GTPase | Tgtp | L38444 | −3.8 |
| | 101144_at | interleukin 18 receptor 1 | Il18r1 | U43673 | −3.6 |
| | 99461_at | hematopoietic cell specific Lyn substrate 1 | Hcls1 | X84797 | −3.5 |
| | 98446_s_at | Eph receptor B4 | Ephb4 | U06834 | −3.4 |
| | 98465_f_at | interferon activated gene 204 | Ifi204 | M31419 | −3.4 |
| | 102635_at | vesicle transport through interaction with t-SNAREs 1 homolog | Vti1-pending | AF035823 | −3.3 |
| | 96764_at | interferon-inducible GTPase | ligp-pending | AJ007971 | −3.2 |
| | 94855_at | Prohibitin | Phb | X78682 | −3.2 |
| | 98822_at | interferon-stimulated protein (15 kDa) | Isg15 | X56602 | −3.2 |
| | 104093_at | lymphocyte specific 1 | Lsp1 | D49691 | −3.1 |
| | 101571_g_at | insulin-like growth factor binding protein 4 | Igfbp4 | X76066 | −3.1 |
| | 103367_at | UDP-N-acetyl-alpha-D-galactosamine:(N-acetylneuraminyl)-galactosylglucosylceramide-beta-1,4-N-acetylgalactosaminyltransferase | Galgt1 | U18975 | −2.9 |
| | 96046_at | histone deacetylase 1 | Hdac1 | X98207 | −2.9 |
| | 93290_at | purine-nucleoside phosphorylase | Pnp | U35374 | −2.9 |
| | 160503_at | Fibrillarin | Fbl | Z22593 | −2.9 |
| | 97507_at | peptidylprolyl isomerase C-associated protein | Ppicap | X67809 | −2.9 |
| | 96297_at | EBNA1 binding protein 2 | Ebp2 | AI845934 | −2.8 |
| | 93218_at | SWAP complex protein, 70 kDa | Swap70 | AF053974 | −2.8 |
| | 92220_s_at | myc box dependent interacting protein 1 | Bin1 | U60884 | −2.8 |
| | 93924_f_at | tubulin, alpha 7 | Tuba7 | M13443 | −2.7 |
| | 98589_at | adipose differentiation related protein | Adfp | M93275 | −2.6 |
| | 100154_at | TAP binding protein | Tapbp | AI836367 | −2.6 |
| | 97875_at | adhesion regulating molecule 1 | Adrm1 | AW123694 | −2.6 |
| | 93518_at | ribonucleic acid binding protein S1 | Rnps1 | X70067 | −2.5 |
| | 160944_at | plakophilin 3 | Pkp3 | AW120906 | −2.4 |
| | 95733_at | solute carrier family 29 (nucleoside transporters), member 1 | Slc29a1 | AI838274 | −2.4 |
| | 92879_at | protein phosphatase 1G (formerly 2C), magnesium-dependent, gamma isoform | Ppm1g | U42383 | −2.4 |

TABLE 3-continued

| TIME | AFFY PROBE ID | GENE NAME | SYMBOL | ACCESSION | FOLD CHANGE |
|---|---|---|---|---|---|
| | 161585_at | glycoprotein 5 (platelet) | Gp5 | AV318587 | −2.4 |
| | 103823_at | topoisomerase (DNA) III beta | Top3b | AB013603 | −2.4 |
| | 160318_at | STIP1 homology and U-Box containing protein 1 | Stub1 | AI844511 | −2.4 |
| | 99486_at | centromere autoantigen B | Cenpb | X55038 | −2.4 |
| | 94815_at | 2,3-bisphosphoglycerate mutase | Bpgm | X13586 | −2.4 |
| | 97251_at | mitochondrial ribosomal protein S10 | Mrps10 | AI842124 | −2.4 |
| | 101486_at | proteasome (prosome, macropain) subunit, beta type 10 | Psmb10 | Y10875 | −2.4 |
| | 104275_g_at | transformation related protein 53 | Trp53 | AB021961 | −2.4 |
| | 100632_at | protein kinase, AMP-activated, gamma 1 non-catalytic subunit | Prkag1 | AF036535 | −2.3 |
| | 94168_at | interleukin 13 | Il13 | M23504 | −2.3 |
| | 104025_at | thimet oligopeptidase 1 | Thop1 | AW047185 | −2.3 |
| | 160106_at | capping protein (actin filament), gelsolin-like | Capg | X54511 | −2.3 |
| | 99639_at | ubiquintin c-terminal hydrolase related polypeptide | Uchrp | D84096 | −2.3 |
| | 92204_at | CD6 antigen | Cd6 | U12434 | −2.3 |
| | 92637_at | phosphofructokinase, liver, B-type | Pfkl | J03928 | −2.3 |
| | 93364_at | Catenin alpha 1 | Catna1 | X59990 | −2.2 |
| | 93892_at | CUG triplet repeat, RNA binding protein 2 | Cugbp2 | Y18298 | −2.2 |
| | 103025_at | Moloney leukemia virus 10 | Mov10 | X52574 | −2.2 |
| | 100962_at | Ngfi-A binding protein 2 | Nab2 | U47543 | −2.2 |
| | 99669_at | lectin, galactose binding, soluble 1 | Lgals1 | X15986 | −2.2 |
| | 104653_at | core binding factor beta | Cbfb | AA864065 | −2.2 |
| | 101989_at | ubiquinol-cytochrome c reductase core protein 1 | Uqcrc1 | AW125380 | −2.1 |
| | 97532_at | Protein phosphatase 5, catalytic subunit | Ppp5c | AF018262 | −2.1 |
| | 98030_at | tripartite motif protein 30 | Trim30 | J03776 | −2.1 |
| | 98339_at | synaptotagmin 11 | Syt11 | AB026808 | −2.1 |
| | 100101_at | small nuclear ribonucleoprotein polypeptide A | Snrpa | L15447 | −2.1 |
| | 101510_at | proteasome (prosome, macropain) 28 subunit, alpha | Psme1 | AB007136 | −2.1 |
| | 92540_f_at | spermidine synthase | Srm | Z67748 | −2.1 |
| | 98153_at | chaperonin subunit 3 (gamma) | Cct3 | L20509 | −2.1 |
| | 102877_at | granzyme B | Gzmb | M12302 | −2.1 |
| | 160290_at | insulin degrading enzyme | Ide | AI574278 | −2.1 |
| | 99323_at | interleukin 12 receptor, beta 2 | Il12rb2 | U64199 | −2.1 |
| | 97867_at | hydroxysteroid 11-beta dehydrogenase 1 | Hsd11b1 | X83202 | −2.1 |
| | 92688_at | acid phosphatase 2, lysosomal | Acp2 | X57199 | −2.1 |
| | 104712_at | myelocytomatosis oncogene | Myc | L00039 | −2.0 |
| | 160521_at | Nucleolin | Ncl | U01139 | −2.0 |
| | 102791_at | proteasome (prosome, macropain) subunit, beta type 8 (large multifunctional protease 7) | Psmb8 | U22033 | −2.0 |
| | 99169_at | coactivator-associated arginine methyltransferase 1 | Carm1-pending | AW122165 | −2.0 |
| | 101492_at | protein (peptidyl-prolyl cis/trans isomerase) NIMA-interacting 1 | Pin1 | AW047032 | −2.0 |
| | 96883_at | eukaryotic translation initiation factor 3, subunit 4 (delta, 44 kDa) | Eif3s4 | U70733 | −2.0 |
| | 102257_at | Pbx/knotted 1 homeobox | Pknox1 | AF061270 | −2.0 |
| | 93500_at | aminolevulinic acid synthase 1 | Alas1 | M63245 | −2.0 |
| | 103683_at | dihydroorotate dehydrogenase | Dhodh | AF029667 | −2.0 |
| | 99478_at | protein tyrosine phosphatase, receptor type, C polypeptide-associated protein | Ptprcap | X97268 | −2.0 |
| | 103946_at | proline-serine-threonine phosphatase-interacting protein 1 | Pstpip1 | U87814 | −2.0 |
| | 102940_at | lymphotoxin B | Ltb | U16985 | −2.0 |
| | 104137_at | ATP-binding cassette, sub-family A (ABC1), member 2 | Abca2 | X75927 | −2.0 |
| | 100156_at | mini chromosome maintenance deficient 5 (S. cerevisiae) | Mcmd5 | D26090 | −2.0 |
| | 104102_at | protease, serine, 25 | Prss25 | AW047978 | −2.0 |
| | 94138_s_at | Fucosyltransferase 7 | Fut7 | U45980 | −2.0 |
| | 102778_at | immunoglobulin-associated alpha | Iga | X13450 | −2.0 |
| | 92203_s_at | CD6 antigen | Cd6 | U37543 | −1.9 |
| | 94850_at | acyl-Coenzyme A thioesterase 3, mitochondrial | Acate3-pending | AJ238894 | −1.9 |
| | 98500_at | interleukin 1 receptor-like 1 | Il1rl1 | D13695 | 2.0 |
| | 160439_at | polymerase, gamma | Polg | U53584 | 2.0 |
| | 103518_at | cytotoxic T lymphocyte-associated protein 2 beta | Ctla2b | X15592 | 2.0 |
| | 103259_at | Growth factor independent 1 | Gfi1 | U58972 | 2.0 |
| | 100606_at | prion protein | Prnp | M18070 | 2.0 |
| | 99143_at | trans-golgi network protein 2 | Tgoln2 | AA614914 | 2.2 |
| | 96912_s_at | cytotoxic T lymphocyte-associated protein 2 alpha | Ctla2a | X15591 | 2.2 |
| | 162172_f_at | neural precursor cell expressed, developmentally down-regulated gene 4a | Nedd4a | AV365271 | 2.2 |
| | 102955_at | nuclear factor, interleukin 3, regulated | Nfil3 | U83148 | 2.4 |
| | 96336_at | glycine amidinotransferase (L-arginine:glycine amidinotransferase) | Gatm | AI844626 | 2.5 |
| | 92217_s_at | glycoprotein 49 B | Gp49b | U05265 | 2.5 |
| | 92480_f_at | Zinc finger protein 118 | Zfp118 | AB024004 | 2.5 |

TABLE 3-continued

| TIME | AFFY PROBE ID | GENE NAME | SYMBOL | ACCESSION | FOLD CHANGE |
|---|---|---|---|---|---|
| | 94458_at | caspase 6 | Casp6 | Y13087 | 2.6 |
| | 93497_at | complement component 3 | C3 | K02782 | 2.8 |
| | 99178_at | glycoprotein m6b | Gpm6b | AI845652 | 2.9 |
| | 161281_f_at | immediate early response 3 | Ier3 | AV292869 | 3.0 |
| | 97157_at | NK-3 transcription factor, locus 1 (*Drosophila*) | Nkx3-1 | U88542 | 3.1 |
| | 104580_at | phospholipase C, delta | Plcd | U85711 | 3.2 |
| | 100325_at | glycoprotein 49 A | Gp49a | M65027 | 3.2 |
| | 100398_at | Kinesin family member 3a | Kif3a | D12645 | 3.2 |
| | 104728_at | Protein S (alpha) | Pros1 | L27439 | 3.4 |
| | 100924_at | GATA binding protein 3 | Gata3 | X55123 | 3.5 |
| | 92285_at | interleukin 4 | Il4 | AA967539 | 3.6 |
| | 103833_at | homeodomain interacting protein kinase 2 | Hipk2 | AF077659 | 4.1 |
| | 160374_r_at | polypyrimidine tract binding protein 2 | Ptbp2 | AI119718 | 4.2 |
| | 160495_at | aryl-hydrocarbon receptor | Ahr | M94623 | 5.3 |
| | | Target genes of Stat6 in murine CD4+ T cells (Th2 Stat6−/− vs Th2 Stat6+/+) | | | |
| 2 h | 161903_f_at | molecule possessing ankyrin-repeats induced by lipopolysaccharide | Mail-pending | AV374591 | −8.0 |
| | 99126_at | inactive X specific transcripts | Xist | L04961 | −6.0 |
| | 101920_at | DNA polymerase epsilon, subunit 2 | Pole2 | AF036898 | −5.9 |
| | 101462_r_at | praja1, RING-H2 motif containing | Pja1 | U06944 | −4.3 |
| | 160948_at | protein phosphatase 3, catalytic subunit, gamma isoform | Ppp3cc | M81475 | −4.3 |
| | 103389_at | lysine oxoglutarate reductase, saccharopine dehydrogenase | Lorsdh | AJ224761 | −3.4 |
| | 100606_at | prion protein | Prnp | M18070 | −3.0 |
| | 162490_f_at | programmed cell death 6 | Pdcd6 | AV138382 | −2.6 |
| | 104663_at | phosphatidylinositol-4-phosphate 5-kinase, type 1 beta | Pip5k1b | D86177 | −2.5 |
| | 162313_f_at | UDP-N-acetyl-alpha-D-galactosamine:polypeptide N-acetylgalactosaminyltransferase 3 | Galnt3 | AV055653 | −2.2 |
| | 160662_r_at | GATA binding protein 6 | Gata6 | AA667100 | −2.2 |
| | 94018_at | ubiquitin-like 3 | Ubl3 | AW120725 | −2.2 |
| | 94321_at | keratin complex 1, acidic, gene 10 | Krt1-10 | V00830 | −2.2 |
| | 98853_at | phospholipase A2, group IB, pancreas, receptor | Pla2g1br | D30779 | −2.1 |
| | 92283_s_at | interleukin 4 | Il4 | X03532 | −2.1 |
| | 160399_r_at | H2A histone family, member Y | H2afy | AA646966 | −2.1 |
| | 96515_at | interleukin-four induced gene 1 | Fig1 | U70430 | −2.1 |
| | 102024_at | nuclear receptor coactivator 3 | Ncoa3 | AF000581 | −2.1 |
| | AFFX-MurIL4_at | interleukin 4 | Il4 | M25892 | −2.1 |
| | 96013_r_at | matrin 3 | Matr3 | AI835367 | −2.1 |
| | 95511_at | integrin alpha 6 | Itga6 | X69902 | −2.0 |
| | 102021_at | interleukin 4 receptor, alpha | Il4ra | M27960 | −2.0 |
| | 92286_g_at | interleukin 4 | Il4 | AA967539 | −2.0 |
| | 99630_at | mitochondrial ribosomal protein L54 | Mrpl54 | AW060257 | −2.0 |
| | 162379_r_at | vimentin | Vim | AV245272 | −1.9 |
| | 100277_at | inhibin beta-A | Inhba | X69619 | −1.9 |
| | 99917_at | enhancer of zeste homolog 2 (*Drosophila*) | Ezh2 | U52951 | −1.9 |
| | 103021_r_at | mitogen activated protein kinase kinase kinase 1 | Map3k1 | AI317205 | −1.9 |
| | 95784_at | paired-Ig-like receptor A1 | Pira1 | U96682 | 2.1 |
| | 104371_at | diacylglycerol O-acyltransferase 1 | Dgat1 | AF078752 | 2.3 |
| | 92368_at | receptor (calcitonin) activity modifying protein 3 | Ramp3 | AJ250491 | 2.3 |
| | 98525_f_at | erythroid differentiation regulator | edr | AJ007909 | 2.4 |
| | 94755_at | interleukin 1 alpha | Il1a | M14639 | 2.5 |
| | 95738_at | pyrroline-5-carboxylate synthetase (glutamate gamma-semialdehyde synthetase) | Pycs | AW124889 | 2.5 |
| | 92330_r_at | NADH dehydrogenase (ubiquinone) 1 alpha subcomplex, 1 | Ndufa1 | AA517665 | 2.6 |
| | 95546_g_at | insulin-like growth factor 1 | Igf1 | X04480 | 3.9 |
| | 160502_at | cellular repressor of E1A-stimulated genes | Creg | AF084524 | 5.0 |
| | 93638_s_at | immunoglobulin lambda chain, variable 1 | Igl-V1 | J00579 | 13.4 |
| | 162172_f_at | neural precursor cell expressed, developmentally down-regulated gene 4a | Nedd4a | AV365271 | 13.9 |
| 6 h | 104728_at | protein S (alpha) | Pros1 | L27439 | −15.3 |
| | 94458_at | caspase 6 | Casp6 | Y13087 | −11.3 |
| | 104228_at | CD84 antigen | Cd84 | AA607237 | −4.8 |
| | 102021_at | interleukin 4 receptor, alpha | Il4ra | M27960 | −2.9 |
| | 94331_at | signal transducer and activator of transcription 6 | Stat6 | L47650 | −2.6 |
| | 98868_at | B-cell leukemia/lymphoma 2 | Bcl2 | L31532 | −2.2 |
| | 92638_at | protein phosphatase 2a, catalytic subunit, alpha isoform | Ppp2ca | Z67745 | −2.1 |
| | 96515_at | interleukin-four induced gene 1 | Fig1 | U70430 | −2.1 |
| | 160948_at | protein phosphatase 3, catalytic subunit, gamma isoform | Ppp3cc | M81475 | −2.0 |
| | 96533_at | ATP-dependant interferon responsive | Adir | AI508931 | 1.9 |
| | 96498_at | disrupted meiotic cDNA 1 homolog | Dmc1h | D64107 | 1.9 |

TABLE 3-continued

| TIME | AFFY PROBE ID | GENE NAME | SYMBOL | ACCESSION | FOLD CHANGE |
|---|---|---|---|---|---|
| | 94781_at | hemoglobin alpha, adult chain 1 | Hba-a1 | V00714 | 2.0 |
| | 101144_at | interleukin 18 receptor 1 | Il18r1 | U43673 | 2.0 |
| | 99107_at | growth hormone receptor | Ghr | M31680 | 2.0 |
| | 93078_at | lymphocyte antigen 6 complex, locus A | Ly6a | X04653 | 2.0 |
| | 162457_f_at | hemoglobin, beta adult major chain | Hbb-b1 | AV003378 | 2.1 |
| | 103534_at | hemoglobin, beta adult minor chain | Hbb-b2 | V00722 | 2.1 |
| | 161894_r_at | zinc finger protein 162 | Zfp162 | AV103574 | 2.2 |
| | 92441_at | fibroblast activation protein | Fap | Y10007 | 2.2 |
| | 94774_at | interferon activated gene 202A | Ifi202a | M31418 | 2.3 |
| | 97890_at | serum/glucocorticoid regulated kinase | Sgk | AW046181 | 2.3 |
| | 93858_at | small inducible cytokine B subfamily (Cys-X-Cys), member 10 | Scyb10 | M33266 | 2.4 |
| | 103486_at | interleukin 1 beta | Il1b | M15131 | 2.5 |
| | 97949_at | fibrinogen-like protein 2 | Fgl2 | M16238 | 2.9 |
| | 102621_at | cell adhesion molecule-related/down-regulated by oncogenes | Cdon | AF090866 | 3.5 |
| | 92369_at | transforming growth factor alpha | Tgfa | M92420 | 5.8 |
| | 161035_at | kinesin 9 | Kif9 | AA122519 | 12.4 |
| 24 h | 99895_at | chemokine (C—C) receptor 8 | Cmkbr8 | AF001277 | −14.5 |
| | 92382_at | myosin VI | Myo6 | U49739 | −14.4 |
| | 103639_at | interferon-induced protein with tetratricopeptide repeats 2 | Ifit2 | U43085 | −12.9 |
| | 104728_at | protein S (alpha) | Pros1 | L27439 | −6.2 |
| | 94458_at | caspase 6 | Casp6 | Y13087 | −6.0 |
| | 100924_at | GATA binding protein 3 | Gata3 | X55123 | −5.9 |
| | 93750_at | gelsolin | Gsn | J04953 | −5.4 |
| | 93214_at | calcium/calmodulin-dependent protein kinase II, delta | Camk2d | AF059029 | −5.2 |
| | 94331_at | signal transducer and activator of transcription 6 | Stat6 | L47650 | −4.9 |
| | 103833_at | homeodomain interacting protein kinase 2 | Hipk2 | AF077659 | −4.2 |
| | 102021_at | interleukin 4 receptor, alpha | Il4ra | M27960 | −3.2 |
| | 104155_f_at | activating transcription factor 3 | Atf3 | U19118 | −3.1 |
| | 102955_at | nuclear factor, interleukin 3, regulated | Nfil3 | U83148 | −3.0 |
| | 100127_at | cellular retinoic acid binding protein II | Crabp2 | M35523 | −2.9 |
| | 101902_at | recombining binding protein suppressor of hairless (Drosophila) | Rbpsuh | X17459 | −2.8 |
| | 160948_at | protein phosphatase 3, catalytic subunit, gamma isoform | Ppp3cc | M81475 | −2.6 |
| | AFFX-MurIL4_at | interleukin 4 | Il4 | M25892 | −2.5 |
| | 92250_s_at | papillary renal cell carcinoma (translocation-associated) | Prcc | AA089181 | −2.4 |
| | 92283_s_at | interleukin 4 | Il4 | X03532 | −2.4 |
| | 92286_g_at | interleukin 4 | Il4 | AA967539 | −2.4 |
| | 94821_at | X-box binding protein 1 | Xbp1 | AW123880 | −2.2 |
| | 101945_g_at | lysophospholipase 1 | Lypla1 | U89352 | −2.1 |
| | 104156_r_at | activating transcription factor 3 | Atf3 | U19118 | −2.1 |
| | 103516_at | cadherin EGF LAG seven-pass G-type receptor 1 | Celsr1 | AF031572 | −2.1 |
| | 98282_at | inducible T-cell co-stimulator | Icos | AB023132 | −2.1 |
| | 100606_at | prion protein | Prnp | M18070 | −2.1 |
| | 103259_at | growth factor independent 1 | Gfi1 | U58972 | −2.1 |
| | 101947_at | neighbor of A-kinase anchoring protein 95 | Nakap95-pending | AB028921 | −2.1 |
| | 92234_at | retinoid X receptor alpha | Rxra | X66223 | −2.1 |
| | 98038_at | high mobility group box 3 | Hmgb3 | AF022465 | −2.0 |
| | 93444_at | basic leucine zipper transcription factor, ATF-like | Batf | AF017021 | −2.0 |
| | 92480_f_at | Zinc finger protein 118 | Zfp118 | AB024004 | −2.0 |
| | 99334_at | interferon gamma | Ifng | K00083 | 1.9 |
| | 102629_at | tumor necrosis factor | Tnf | D84196 | 2.0 |
| | 98002_at | interferon concensus sequence binding protein | Icsbp | M32489 | 2.0 |
| | 160906_i_at | ectodermal-neural cortex 1 | Enc1 | AA184423 | 2.0 |
| | 94781_at | hemoglobin alpha, adult chain 1 | Hba-a1 | V00714 | 2.1 |
| | 94028_f_at | CD84 antigen | Cd84 | AI642245 | 2.1 |
| | 161528_r_at | DNA polymerase delta 1, catalytic domain | Pold1 | AV227261 | 2.1 |
| | 92614_at | inhibitor of DNA binding 3 | Idb3 | M60523 | 2.1 |
| | 161167_r_at | uridine monophosphate kinase | Umpk | AV223645 | 2.1 |
| | 94027_at | CD84 antigen | Cd84 | AA815831 | 2.1 |
| | 101869_s_at | hemoglobin, beta adult major chain | Hbb-b1 | J00413 | 2.2 |
| | 97426_at | epithelial membrane protein 1 | Emp1 | X98471 | 2.2 |
| | 103279_at | SH2 domain protein 1A | Sh2d1a | AF097632 | 2.2 |
| | 162409_r_at | nuclear protein 220 | Np220 | AV315224 | 2.3 |

TABLE 3-continued

| TIME | AFFY PROBE ID | GENE NAME | SYMBOL | ACCESSION | FOLD CHANGE |
|---|---|---|---|---|---|
| | 96764_at | interferon-inducible GTPase | Iigp-pending | AJ007971 | 2.3 |
| | 161884_r_at | fragile X mental retardation gene 1, autosomal homolog | Fxr1h | AV368725 | 2.3 |
| | 103534_at | hemoglobin, beta adult minor chain | Hbb-b2 | V00722 | 2.3 |
| | 94378_at | regulator of G-protein signaling 16 | Rgs16 | U94828 | 2.3 |
| | 94774_at | interferon activated gene 202A | Ifi202a | M31418 | 2.3 |
| | 98577_f_at | prefoldin 5 | Pfdn5 | Y12713 | 2.4 |
| | 97185_at | aryl hydrocarbon receptor nuclear translocator | Arnt | AI451564 | 2.5 |
| | 102424_at | small inducible cytokine A3 | Scya3 | J04491 | 2.5 |
| | 98782_at | complexin 2 | Cplx2 | D38613 | 2.7 |
| | 161609_at | regulator of G-protein signaling 16 | Rgs16 | AV349152 | 2.7 |
| | 101571_g_at | insulin-like growth factor binding protein 4 | Igfbp4 | X76066 | 2.9 |
| | 94146_at | small inducible cytokine A4 | Scya4 | X62502 | 3.0 |
| | 93321_at | interferon activated gene 203 | Ifi203 | AF022371 | 3.1 |
| | 101313_r_at | Mus musculus endogenous provirus Imposon1 envelope gene, partial cds, and 3' long terminal repeat, complete sequence | | U95783 | 3.4 |
| | 103389_at | lysine oxoglutarate reductase, saccharopine dehydrogenase | Lorsdh | AJ224761 | 3.4 |
| | 101144_at | interleukin 18 receptor 1 | Il18r1 | U43673 | 4.4 |
| | 161968_f_at | chemokine (C—C) receptor 5 | Cmkbr5 | AV370035 | 7.9 |
| | 160726_at | quaking | qk | U44940 | 11.5 |
| | 102958_at | early B-cell factor 2 | Ebf2 | U82441 | 14.8 |
| | 161417_r_at | neuroblastoma myc-related oncogene 1 | Nmyc1 | AV320040 | 16.4 |
| | 162451_r_at | f-box only protein 3 | Fbxo3 | AV027999 | 33.6 |
| 48 h | 92382_at | myosin VI | Myo6 | U49739 | −8.6 |
| | 104728_at | Protein S (alpha) | Pros1 | L27439 | −4.6 |
| | 103833_at | homeodomain-interacting protein kinase 2(HIPK2) | Hipk2 | AF077659 | −4.6 |
| | 94331_at | signal transducer and activator of transcription 6 | Stat6 | L47650 | −3.5 |
| | 92286_g_at | Interleukin 4 | Il4 | AA967539 | −3.5 |
| | 100924_at | GATA3 | Gata3 | X55123 | −3.2 |
| | 100325_at | Glycoprotein 49 A (Gp49a) | Gp49a | M65027 | −3.2 |
| | AFFX-MurIL4_at | Interleukin 4 | Il4 | M25892 | −3.2 |
| | 101926_at | protein-serine/threonine kinase (pim-2) | Pim2 | L41495 | −2.8 |
| | 99178_at | glycoprotein m6b | Gpm6b | AI845652 | −2.6 |
| | 100596_at | selenium binding protein 1 | Selenbp1 | M32032 | −2.6 |
| | 93574_at | serine (or cysteine) proteinase inhibitor, clade F (alpha-2 antiplasmin, pigment epithelium derived factor), member 1 | Serpinf1 | AF036164 | −2.5 |
| | 100606_at | Prion Protein | Prnp | M18070 | −2.0 |
| | 102779_at | growth arrest and DNA-damage-inducible 45 beta | Gadd45b | X54149 | −2.0 |
| | 160948_at | protein phosphatase 3, catalytic subunit, gamma isoform | Ppp3cc | M81475 | −2.0 |
| | 92480_f_at | Zinc finger protein 118 | Zfp118 | AB024004 | −2.0 |
| | 102955_at | NFIL3/E4BP4 transcription factor | Nfil3 | U83148 | −2.0 |
| | 93865_s_at | histocompatibility 2, T region locus 22 | H2-T22 | M35244 | 2.0 |
| | 103025_at | Moloney leukemia virus 10 | Mov10 | X52574 | 2.0 |
| | 98600_at | S100 calcium binding protein A11 | S100a11 | U41341 | 2.0 |
| | 97507_at | peptidylprolyl isomerase C-associated protein | Ppicap | X67809 | 2.1 |
| | 104679_at | TXK tyrosine kinase | Txk | D43963 | 2.1 |
| | 98525_f_at | erythroid differentiation regulator | edr | AJ007909 | 2.1 |
| | 98030_at | tripartite motif protein 30 | Trim30 | J03776 | 2.3 |
| | 98822_at | interferon-stimulated protein (15 kDa) | Isg15 | X56602 | 2.5 |
| | 92644_s_at | myb proto-oncogene | Myb | M12848 | 2.5 |
| | 93078_at | lymphocyte antigen 6 complex | Ly6a | X04653 | 2.5 |
| | 102877_at | granzyme B (Gzmb) | Gzmb | M12302 | 2.6 |
| | 92214_at | cathepsin W | Ctsw | AF014941 | 2.6 |
| | 102906_at | T-cell specific GTPase | Tgtp | L38444 | 2.8 |
| | 96060_at | serine (or cysteine) proteinase inhibitor, clade B (ovalbumin), member 6 | Serpinb6 | U25844 | 2.8 |
| | 93321_at | interferon activated gene 203 | Ifi203 | AF022371 | 3.5 |
| | 103554_at | a disintegrin and metalloproteinase domain 19 (meltrin beta) | Adam19 | AA726223 | 4.0 |
| | 161968_f_at | chemokine (C—C) receptor 5 | Cmkbr5 | AV370035 | 4.3 |
| | 94224_s_at | interferon activated gene 205 | Ifi205 | M74123 | 4.6 |
| | 101144_at | interleukin 18 receptor 1 | Il18r1 | U43673 | 4.9 |
| | 103432_at | interferon-stimulated protein (20 kDa) | Isg20 | AW122677 | 5.7 |

TABLE IV

The human oligos used for quantitative Real-Time RT-PCR.

| ACCESSION | GENE | 1) 5'-6(FAM)-PROBE-(TAMRA)-3'<br>2) 5'-PRIMER 1-3'<br>3) 5'-PRIMER 2-3' |
|---|---|---|
| AB013602, AB013382 | DUSP6 (short & long) | 1) 5'-CTCTACGACGAGAGCAGCAGCGACTG-3' SEQ ID NO:16 |
| | | 2) 5'-GCTGTGGCACCGACACAGT-3' SEQ ID NO:17 |
| | | 3) 5'-ACTCGCCGCCCGTATTCT-3' SEQ ID NO:18 |
| AB013382 | DUSP6 (long) | 1) 5'-CTCTACGACGAGAGCAGCAGCGACTG-3' SEQ ID NO:19 |
| | | 2) 5'-GCTGTGGCACCGACACAGT-3' SEQ ID NO:20 |
| | | 3) 5'-GAACTCGGCTTGGAACTTACTGAA-3' SEQ ID NO:21 |
| X64318 | E4BP4 (NFIL3) | 1) 5'-TCCTCAGTAGAACACACGCAGGAGAGCTC-3' SEQ ID NO:22 |
| | | 2) 5'-AGCTCGCTGTCCGATGTTTC-3' SEQ ID NO:23 |
| | | 3) 5'-CTTCTGCAGCTTCCCTGCAC-3 SEQ ID NO:24 |
| J04617 | EF1α | 1) 5'-AGCGCCGGCTATGCCCCTG-3' SEQ ID NO:25 |
| | | 2) 5'-CTGAACCATCCAGGCCAAAT-3' SEQ ID NO:26 |
| | | 3) 5'-GCCGTGTGGCAATCCAAT-3' SEQ ID NO:27 |
| AF078077 | GADD45β | 1) 3'-TGGCCACCTCCACCAAGCCG-5' SEQ ID NO:28 |
| | (Myd118) | 2) 3'-CCGGCTTTCTTCGCAGTAG-5' SEQ ID NO:29 |
| | | 3) 5'-CACGGACGCCTGGAAGA-3' SEQ ID NO:30 |

TABLE IV-continued

The human oligos used for quantitative Real-Time RT-PCR.

| ACCESSION | GENE | 1) 5'-6(FAM)-PROBE-(TAMRA)-3'<br>2) 5'-PRIMER 1-3'<br>3) 5'-PRIMER 2-3' |
|---|---|---|
| X55122 | GATA-3 | 1) 5'-TGCCGGAGGAGGTGGATGTGCT-3' SEQ ID NO:31 |
| | | 2) 5'-GGACGCGGCGCAGTAC-3' SEQ ID NO:32 |
| | | 3) 5'-TGCCTTGACCGTCGATGTTA-3' SEQ ID NO:33 |
| M37265 | IFNγ | 1) 5'-TGCTGGCGACAGTTCAGCCATCAC-3' SEQ ID NO:34 |
| | | 2) 5'-CTCGAAACAGCATCTGACTCCTT-3' SEQ ID NO:35 |
| | | 3) 5'-TGTCCAACGCAAAGCAATACA-3' SEQ ID NO:36 |
| m97287 | SATB1 | 1) 5'-AACGAGCAGGAATCTCCCAGGCG-3' SEQ ID NO:37 |
| | | 2) 5'-ACCAGTGGGTACGCGATGA-3' SEQ ID NO:38 |
| | | 3) 5'-TGTTAAAAGCCACACGTGCAA-3' SEQ ID NO:39 |
| AF241243 | T-bet | 1) 5'-TCAGCATGAAGCCTGCATTCTTGCC-3' SEQ ID NO:40 |
| | | 2) 5'-ACAGCTATGAGGCTGAGTTTCGA-3' SEQ ID NO:41 |
| | | 3) 5'-GGCCTCGGTAGTAGGACATGG T-3' SEQ ID NO:42 |
| AB000734 | TIP3 (SSI-1, SOCS-1, JAB) | 1) 5'-TTCGCACGCCGATTACCGGC-'3 SEQ ID NO:43 |
| | | 2) 5'-ACACGCACTTCCGCACATT-3' SEQ ID NO:44 |
| | | 3) 5'-CTGGCGCGCGTGATG-'3 SEQ ID NO:45 |

TABLE V

The murine oligos used for quantitative Real-Time RT-PCR.

| | Forward Primer | Reverse Primer | Probe |
|---|---|---|---|
| Hipk2 | CAGTGAAGTGTTGGTAGAATGTGACA | GCTGGAGGACTTGGACTTGAAG | CCAGCGATCAGTGCCAGTCACCATT |
| Nfil3 | CATCACAAAGAACTGAGCAGCAA | AACCTTATAGCCACCGTCTTTGAC | TCCACCACACCTGTTTTGAAGCTACTCTGAG |
| Zfp118 | GAACAAAGAGACCTGGAAGATGGA | GAAGAATAATGAATAGCTGGCTTGTG | TCCTGGATCCTTAGCTACTGCCTCCTGTCT |
| Atf3 | GGCGGCGAGAAAGAAATAAA | GCAGGCACTCTGTCTTCTCCTT | TCTTGTTTCGACACTTGGCAGCAGCA |
| Ifi203 | TCAGCTGGCGGACTGGAT | TGCTCACACACTTTTATCAGTTTGTC | AGGACAAGTTCCCCAAAGATGCTGGACT |

TABLE 6

| TIME | AFFY PROBE ID | GENE NAME | SYMBOL | ACCESSION | FOLD CHANGE |
|---|---|---|---|---|---|
| | | Novel target genes of IL-4 in murine CD4+ T cells (Th2-induced vs activated) | | | |
| 2 h | 103841_at | zinc finger protein 64 | Zfp64 | U49046 | −3.5 |
| | 160273_at | zinc finger protein 36, C3H type-like 2 | Zfp36l2 | AA960603 | −2.3 |
| | 96623_at | UDP-glucose ceramide glucosyltransferase-like | Ugcgl | AI853172 | −2.3 |
| | 92368_at | receptor (calcitonin) activity modifying protein 3 | Ramp3 | AJ250491 | −2.2 |
| | 98478_at | cyclin G2 | Ccng2 | U95826 | −2.1 |
| | 98072_r_at | deoxycytidine kinase | Dck | X77731 | −2.0 |
| | 104371_at | diacylglycerol O-acyltransferase 1 | Dgat1 | AF078752 | −1.9 |
| | 160439_at | polymerase, gamma | Polg | U53584 | 2.0 |
| | 102797_at | retinal short-chain dehydrogenase/reductase 1 | Rsdr1-pending | X95281 | 2.0 |
| | 104449_at | glycine receptor, beta subunit | Glrb | X81202 | 2.2 |
| | 104400_at | prenylated SNARE protein | Ykt6-pending | AF076956 | 2.3 |
| | 100606_at | prion protein | Prnp | M18070 | 2.3 |
| | 99021_at | paired related homeobox 1 | Prrx1 | U03873 | 2.5 |
| | 100022_at | cytokine inducible SH2-containing protein | Cish | D89613 | 2.5 |
| | 99917_at | enhancer of zeste homolog 2 (*Drosophila*) | Ezh2 | U52951 | 2.5 |
| | 97523_i_at | amylase 2, pancreatic | Amy2 | X02578 | 2.6 |
| | 160948_at | protein phosphatase 3, catalytic subunit, gamma isoform | Ppp3cc | M81475 | 2.8 |
| | 161411_i_at | lipase, hormone sensitive | Lipe | AV315398 | 8.1 |
| | 161491_r_at | f-box only protein 3 | Fbxo3 | AV083174 | 10.5 |
| | 101920_at | DNA polymerase epsilon, subunit 2 | Pole2 | AF036898 | 15.1 |
| 6 h | 100131_at | secretory granule neuroendocrine protein 1, 7B2 protein | Sgne1 | X15830 | −6.0 |
| | 102157_f_at | immunoglobulin kappa chain variable 28 (V28) | Igk-V28 | M15520 | −4.7 |
| | 161997_f_at | aldehyde dehydrogenase 2, mitochondrial | Aldh2 | AV329607 | −2.9 |
| | 92280_at | actinin, alpha 1 | Actn1 | AA867778 | −2.2 |
| | 92608_at | cysteine rich protein | Csrp | D88793 | −2.1 |
| | 101965_at | ring finger protein 13 | Rnf13 | AF037205 | −2.0 |
| | 92614_at | inhibitor of DNA binding 3 | Idb3 | M60523 | −2.0 |
| | 100022_at | cytokine inducible SH2-containing protein | Cish | D89613 | 2.0 |
| | 101913_at | hairy/enhancer-of-split related with YRPW motif 1 | Hey1 | AW214298 | 2.6 |
| | 161051_at | hairy and enhancer of split 5, (*Drosophila*) | Hes5 | D32132 | 2.6 |
| | 160886_i_at | fatty acid binding protein 6, ileal (gastrotropin) | Fabp6 | AV063979 | 3.9 |
| | 100127_at | cellular retinoic acid binding protein II | Crabp2 | M35523 | 5.1 |
| 24 h | 160726_at | Quaking | qk | U44940 | −11.4 |
| | 161609_at | regulator of G-protein signaling 16 | Rgs16 | AV349152 | −2.5 |
| | 96060_at | serine (or cysteine) proteinase inhibitor, clade B (ovalbumin), member 6 | Serpinb6 | U25844 | −2.3 |
| | 161948_f_at | myosin Va | Myo5a | AV214912 | −2.0 |
| | 102638_at | Cystatin F (leukocystatin) | Cst7 | AB015224 | 2.0 |
| | 92234_at | Retinoid X receptor alpha | Rxra | X66223 | 2.0 |
| | 161012_at | immunoglobulin-associated beta | Igb | J03857 | 2.1 |
| | 93444_at | basic leucine zipper transcription factor, ATF-like | Batf | AF017021 | 2.3 |
| | 101902_at | recombining binding protein suppressor of hairless (*Drosophila*) | Rbpsuh | X17459 | 2.5 |
| | 93750_at | Gelsolin | Gsn | J04953 | 3.9 |
| | 92382_at | myosin VI | Myo6 | U49739 | 5.3 |
| 48 h | 93880_at | eomesodermin homolog (*Xenopus laevis*) | Eomes | AB031037 | −5.1 |
| | 103554_at | a disintegrin and metalloproteinase domain 19 (meltrin beta) | Adam19 | AA726223 | −4.3 |
| | 160878_at | block of proliferation 1 | Bop1 | AF061503 | −4.2 |
| | 96060_at | serine (or cysteine) proteinase inhibitor, clade B (ovalbumin), member 6 | Serpinb6 | U25844 | −4.2 |
| | 99461_at | hematopoietic cell specific Lyn substrate 1 | Hcls1 | X84797 | −3.5 |
| | 98446_s_at | Eph receptor B4 | Ephb4 | U06834 | −3.4 |
| | 102635_at | vesicle transport through interaction with t-SNAREs 1 homolog | Vti1-pending | AF035823 | −3.3 |
| | 94855_at | prohibitin | Phb | X78682 | −3.2 |
| | 104093_at | lymphocyte specific 1 | Lsp1 | D49691 | −3.1 |
| | 103367_at | UDP-N-acetyl-alpha-D-galactosamine: (N-acetylneuraminyl)-galactosylglucosylceramide-beta-1,4-N-acetylgalactosaminyltransferase | Galgt1 | U18975 | −2.9 |
| | 96046_at | histone deacetylase 1 | Hdac1 | X98207 | −2.9 |
| | 97507_at | peptidylprolyl isomerase C-associated protein | Ppicap | X67809 | −2.9 |
| | 96297_at | EBNA1 binding protein 2 | Ebp2 | AI845934 | −2.8 |
| | 93218_at | SWAP complex protein, 70 kDa | Swap70 | AF053974 | −2.8 |
| | 92220_s_at | myc box dependent interacting protein 1 | Bin1 | U60884 | −2.8 |
| | 98589_at | Adipose differentiation related protein | Adfp | M93275 | −2.6 |
| | 97875_at | adhesion regulating molecule 1 | Adrm1 | AW123694 | −2.6 |
| | 93518_at | ribonucleic acid binding protein S1 | Rnps1 | X70067 | −2.5 |
| | 160944_at | plakophilin 3 | Pkp3 | AW120906 | −2.4 |
| | 95733_at | solute carrier family 29 (nucleoside transporters), member 1 | Slc29a1 | AI838274 | −2.4 |

TABLE 6-continued

| TIME | AFFY PROBE ID | GENE NAME | SYMBOL | ACCESSION | FOLD CHANGE |
|---|---|---|---|---|---|
| | 92879_at | protein phosphatase 1G (formerly 2C), magnesium-dependent, gamma isoform | Ppm1g | U42383 | −2.4 |
| | 161585_at | glycoprotein 5 (platelet) | Gp5 | AV318587 | −2.4 |
| | 160318_at | STIP1 homology and U-Box containing protein 1 | Stub1 | AI844511 | −2.4 |
| | 103823_at | topoisomerase (DNA) III beta | Top3b | AB013603 | −2.4 |
| | 99486_at | centromere autoantigen B | Cenpb | X55038 | −2.4 |
| | 94815_at | 2,3-bisphosphoglycerate mutase | Bpgm | X13586 | −2.4 |
| | 97251_at | mitochondrial ribosomal protein S10 | Mrps10 | AI842124 | −2.4 |
| | 104275_g_at | transformation related protein 53 | Trp53 | AB021961 | −2.4 |
| | 100632_at | protein kinase, AMP-activated, gamma 1 non-catalytic subunit | Prkag1 | AF036535 | −2.3 |
| | 160106_at | Capping protein (actin filament), gelsolin-like | Capg | X54511 | −2.3 |
| | 104025_at | thimet oligopeptidase 1 | Thop1 | AW047185 | −2.3 |
| | 99639_at | ubiquintin c-terminal hydrolase related polypeptide | Uchrp | D84096 | −2.3 |
| | 92637_at | phosphofructokinase, liver, B-type | Pfkl | J03928 | −2.3 |
| | 93364_at | catenin alpha 1 | Catna1 | X59990 | −2.2 |
| | 93892_at | CUG triplet repeat, RNA binding protein 2 | Cugbp2 | Y18298 | −2.2 |
| | 103025_at | Moloney leukemia virus 10 | Mov10 | X52574 | −2.2 |
| | 99669_at | lectin, galactose binding, soluble 1 | Lgals1 | X15986 | −2.2 |
| | 104653_at | core binding factor beta | Cbfb | AA864065 | −2.2 |
| | 97532_at | protein phosphatase 5, catalytic subunit | Ppp5c | AF018262 | −2.1 |
| | 101989_at | ubiquinol-cytochrome c reductase core protein 1 | Uqcrc1 | AW125380 | −2.1 |
| | 98030_at | Tripartite motif protein 30 | Trim30 | J03776 | −2.1 |
| | 98339_at | synaptotagmin 11 | Syt11 | AB026808 | −2.1 |
| | 100101_at | small nuclear ribonucleoprotein polypeptide A | Snrpa | L15447 | −2.1 |
| | 92540_f_at | spermidine synthase | Srm | Z67748 | −2.1 |
| | 98153_at | chaperonin subunit 3 (gamma) | Cct3 | L20509 | −2.1 |
| | 160290_at | insulin degrading enzyme | Ide | AI574278 | −2.1 |
| | 97867_at | hydroxysteroid 11-beta dehydrogenase 1 | Hsd11b1 | X83202 | −2.1 |
| | 99169_at | coactivator-associated arginine methyltransferase 1 | Carm1-pending | AW122165 | −2.0 |
| | 96883_at | eukaryotic translation initiation factor 3, subunit 4 (delta, 44 kDa) | Eif3s4 | U70733 | −2.0 |
| | 101492_at | protein (peptidyl-prolyl cis/trans isomerase) NIMA-interacting 1 | Pin1 | AW047032 | −2.0 |
| | 102257_at | Pbx/knotted 1 homeobox | Pknox1 | AF061270 | −2.0 |
| | 93500_at | aminolevulinic acid synthase 1 | Alas1 | M63245 | −2.0 |
| | 103683_at | dihydroorotate dehydrogenase | Dhadh | AF029667 | −2.0 |
| | 99478_at | protein tyrosine phosphatase, receptor type, C polypeptide-associated protein | Ptprcap | X97268 | −2.0 |
| | 103946_at | proline-serine-threonine phosphatase-interacting protein 1 | Pstpip1 | U87814 | −2.0 |
| | 104137_at | ATP-binding cassette, sub-family A (ABC1), member 2 | Abca2 | X75927 | −2.0 |
| | 100156_at | mini chromosome maintenance deficient 5 (*S. cerevisiae*) | Mcmd5 | D26090 | −2.0 |
| | 104102_at | protease, serine, 25 | Prss25 | AW047978 | −2.0 |
| | 94138_s_at | fucosyltransferase 7 | Fut7 | U45980 | −2.0 |
| | 94850_at | acyl-Coenzyme A thioesterase 3, mitochondrial | Acate3-pending | AJ238894 | −1.9 |
| | 103518_at | cytotoxic T lymphocyte-associated protein 2 beta | Ctla2b | X15592 | 2.0 |
| | 160439_at | polymerase, gamma | Polg | U53584 | 2.0 |
| | 100606_at | prion protein | Prnp | M18070 | 2.0 |
| | 99143_at | trans-golgi network protein 2 | Tgoln2 | AA614914 | 2.2 |
| | 96912_s_at | cytotoxic T lymphocyte-associated protein 2 alpha | Ctla2a | X15591 | 2.2 |
| | 162172_f_at | neural precursor cell expressed, developmentally down-regulated gene 4a | Nedd4a | AV365271 | 2.2 |
| | 96336_at | glycine amidinotransferase (L-arginine: glycine amidinotransferase) | Gatm | AI844626 | 2.5 |
| | 92217_s_at | glycoprotein 49 B | Gp49b | U05265 | 2.5 |
| | 92480_f_at | Zinc finger protein 118 | Zfp118 | AB024004 | 2.5 |
| | 99178_at | glycoprotein m6b | Gpm6b | AI845652 | 2.9 |
| | 161281_f_at | immediate early response 3 | Ier3 | AV292869 | 3.0 |
| | 97157_at | NK-3 transcription factor, locus 1 (*Drosophila*) | Nkx3-1 | U88542 | 3.1 |
| | 100325_at | glycoprotein 49 A | Gp49a | M65027 | 3.2 |
| | 160374_r_at | polypyrimidine tract binding protein 2 | Ptbp2 | AI119718 | 4.2 |
| | 160495_at | aryl-hydrocarbon receptor | Ahr | M94623 | 5.3 |
| | Novel target genes of Stat6 in murine CD4+ T cells (Th2-induced Stat6−/− cells vs Th2-induced Stat6+/+ cells) | | | | |
| 2 h | 161903_f_at | molecule possessing ankyrin-repeats induced by lipopolysaccharide | Mail-pending | AV374591 | −8.0 |
| | 99126_at | inactive X specific transcripts | Xist | L04961 | −6.0 |
| | 101920_at | DNA polymerase epsilon, subunit 2 | Pole2 | AF036898 | −5.9 |
| | 101462_r_at | praja1, RING-H2 motif containing | Pja1 | U06944 | −4.3 |
| | 160948_at | protein phosphatase 3, catalytic subunit, gamma isoform | Ppp3cc | M81475 | −4.3 |
| | 103389_at | lysine oxoglutarate reductase, saccharopine dehydrogenase | Lorsdh | AJ224761 | −3.4 |
| | 100606_at | prion protein | Prnp | M18070 | −3.0 |

TABLE 6-continued

| TIME | AFFY PROBE ID | GENE NAME | SYMBOL | ACCESSION | FOLD CHANGE |
|---|---|---|---|---|---|
| | 162490_f_at | programmed cell death 6 | Pdcd6 | AV138382 | −2.6 |
| | 104663_at | phosphatidylinositol-4-phosphate 5-kinase, type 1 beta | Pip5k1b | D86177 | −2.5 |
| | 162313_f_at | UDP-N-acetyl-alpha-D-galactosamine: polypeptide N-acetylgalactosaminyltransferase 3 | Galnt3 | AV055653 | −2.2 |
| | 160662_r_at | GATA binding protein 6 | Gata6 | AA667100 | −2.2 |
| | 94018_at | ubiquitin-like 3 | Ubl3 | AW120725 | −2.2 |
| | 94321_at | keratin complex 1, acidic, gene 10 | Krt1-10 | V00830 | −2.2 |
| | 98853_at | phospholipase A2, group IB, pancreas, receptor | Pla2g1br | D30779 | −2.1 |
| | 160399_r_at | H2A histone family, member Y | H2afy | AA646966 | −2.1 |
| | 102024_at | nuclear receptor coactivator 3 | Ncoa3 | AF000581 | −2.1 |
| | 96013_r_at | matrin 3 | Matr3 | AI835367 | −2.1 |
| | 95511_at | integrin alpha 6 | Itga6 | X69902 | −2.0 |
| | 99630_at | mitochondrial ribosomal protein L54 | Mrpl54 | AW060257 | −2.0 |
| | 162379_r_at | vimentin | Vim | AV245272 | −1.9 |
| | 99917_at | enhancer of zeste homolog 2 (Drosophila) | Ezh2 | U52951 | −1.9 |
| | 100277_at | inhibin beta-A | Inhba | X69619 | −1.9 |
| | 103021_r_at | mitogen activated protein kinase kinase kinase 1 | Map3k1 | AI317205 | −1.9 |
| | 95784_at | paired-Ig-like receptor A1 | Pira1 | U96682 | 2.1 |
| | 104371_at | diacylglycerol O-acyltransferase 1 | Dgat1 | AF078752 | 2.3 |
| | 92368_at | receptor (calcitonin) activity modifying protein 3 | Ramp3 | AJ250491 | 2.3 |
| | 94755_at | interleukin 1 alpha | Il1a | M14639 | 2.5 |
| | 95738_at | pyrroline-5-carboxylate synthetase (glutamate gamma-semialdehyde synthetase) | Pycs | AW124889 | 2.5 |
| | 92330_r_at | NADH dehydrogenase (ubiquinone) 1 alpha subcomplex, 1 | Ndufa1 | AA517665 | 2.6 |
| | 160502_at | cellular repressor of E1A-stimulated genes | Creg | AF084524 | 5.0 |
| | 93638_s_at | immunoglobulin lambda chain, variable 1 | Igl-V1 | J00579 | 13.4 |
| | 162172_f_at | neural precursor cell expressed, developmentally down-regulated gene 4a | Nedd4a | AV365271 | 13.9 |
| 6 h | 104228_at | CD84 antigen | Cd84 | AA607237 | −4.8 |
| | 92638_at | protein phosphatase 2a, catalytic subunit, alpha isoform | Ppp2ca | Z67745 | −2.1 |
| | 160948_at | protein phosphatase 3, catalytic subunit, gamma isoform | Ppp3cc | M81475 | −2.0 |
| | 96533_at | ATP-dependant interferon responsive | Adir | AI508931 | 1.9 |
| | 96498_at | disrupted meiotic cDNA 1 homolog | Dmc1h | D64107 | 1.9 |
| | 94781_at | hemoglobin alpha, adult chain 1 | Hba-a1 | V00714 | 2.0 |
| | 99107_at | growth hormone receptor | Ghr | M31680 | 2.0 |
| | 162457_f_at | hemoglobin, beta adult major chain | Hbb-b1 | AV003378 | 2.1 |
| | 103534_at | hemoglobin, beta adult minor chain | Hbb-b2 | V00722 | 2.1 |
| | 161894_r_at | zinc finger protein 162 | Zfp162 | AV103574 | 2.2 |
| | 92441_at | fibroblast activation protein | Fap | Y10007 | 2.2 |
| | 97890_at | serum/glucocorticoid regulated kinase | Sgk | AW046181 | 2.3 |
| | 102621_at | cell adhesion molecule-related/down-regulated by oncogenes | Cdon | AF090866 | 3.5 |
| | 92369_at | transforming growth factor alpha | Tgfa | M92420 | 5.8 |
| | 161035_at | kinesin 9 | Kif9 | AA122519 | 12.4 |
| 24 h | 92382_at | myosin VI | Myo6 | U49739 | −14.9 |
| | 93750_at | gelsolin | Gsn | J04953 | −5.4 |
| | 93214_at | calcium/calmodulin-dependent protein kinase II, delta | Camk2d | AF059029 | −5.2 |
| | 100127_at | cellular retinoic acid binding protein II | Crabp2 | M35523 | −2.9 |
| | 101902_at | recombining binding protein suppressor of hairless (Drosophila) | Rbpsuh | X17459 | −2.8 |
| | 160948_at | protein phosphatase 3, catalytic subunit, gamma isoform | Ppp3cc | M81475 | −2.6 |
| | 92250_s_at | papillary renal cell carcinoma (translocation-associated) | Prcc | AA089181 | −2.4 |
| | 94821_at | X-box binding protein 1 | Xbp1 | AW123880 | −2.2 |
| | 101945_g_at | lysophospholipase 1 | Lypla1 | U89352 | −2.1 |
| | 103516_at | cadherin EGF LAG seven-pass G-type receptor 1 | Celsr1 | AF031572 | −2.1 |
| | 101947_at | neighbor of A-kinase anchoring protein 95 | Nakap95-pending | AB028921 | −2.1 |
| | 100606_at | prion protein | Prnp | M18070 | −2.1 |
| | 92234_at | retinoid X receptor alpha | Rxra | X66223 | −2.1 |
| | 98038_at | high mobility group box 3 | Hmgb3 | AF022465 | −2.0 |
| | 93444_at | basic leucine zipper transcription factor, ATF-like | Batf | AF017021 | −2.0 |
| | 92480_f_at | Zinc finger protein 118 | Zfp118 | AB024004 | −2.0 |
| | 160906_i_at | ectodermal-neural cortex 1 | Enc1 | AA184423 | 2.0 |
| | 94781_at | hemoglobin alpha, adult chain 1 | Hba-a1 | V00714 | 2.1 |
| | 94028_f_at | CD84 antigen | Cd84 | AI642245 | 2.1 |
| | 161528_r_at | DNA polymerase delta 1, catalytic domain | Pold1 | AV227261 | 2.1 |
| | 161167_r_at | uridine monophosphate kinase | Umpk | AV223645 | 2.1 |
| | 94027_at | CD84 antigen | Cd84 | AA815831 | 2.1 |
| | 92614_at | inhibitor of DNA binding 3 | Idb3 | M60523 | 2.1 |
| | 97426_at | epithelial membrane protein 1 | Emp1 | X98471 | 2.2 |

TABLE 6-continued

| TIME | AFFY PROBE ID | GENE NAME | SYMBOL | ACCESSION | FOLD CHANGE |
|---|---|---|---|---|---|
| | 101869_s_at | hemoglobin, beta adult major chain | Hbb-b1 | J00413 | 2.2 |
| | 162409_r_at | nuclear protein 220 | Np220 | AV315224 | 2.3 |
| | 161884_r_at | fragile X mental retardation gene 1, autosomal homolog | Fxr1h | AV368725 | 2.3 |
| | 103534_at | hemoglobin, beta adult minor chain | Hbb-b2 | V00722 | 2.3 |
| | 94378_at | regulator of G-protein signaling 16 | Rgs16 | U94828 | 2.3 |
| | 98577_f_at | prefoldin 5 | Pfdn5 | Y12713 | 2.4 |
| | 97185_at | aryl hydrocarbon receptor nuclear translocator | Arnt | AI451564 | 2.5 |
| | 98782_at | complexin 2 | Cplx2 | D38613 | 2.7 |
| | 161609_at | regulator of G-protein signaling 16 | Rgs16 | AV349152 | 2.7 |
| | 103389_at | lysine oxoglutarate reductase, saccharopine dehydrogenase | Lorsdh | AJ224761 | 3.4 |
| | 101313_r_at | *Mus musculus* endogenous provirus Imposon1 envelope gene, partial cds, and 3' long terminal repeat, complete sequence | | U95783 | 3.4 |
| | 160726_at | quaking | qk | U44940 | 11.5 |
| | 102958_at | early B-cell factor 2 | Ebf2 | U82441 | 14.8 |
| | 162451_r_at | f-box only protein 3 | Fbxo3 | AV027999 | 33.6 |
| 48 h | 92382_at | myosin VI | Myo6 | U49739 | −8.6 |
| | 100325_at | Glycoprotein 49 A (Gp49a) | Gp49a | M65027 | −3.2 |
| | 101926_at | protein-serine/threonine kinase (pim-2) | Pim2 | L41495 | −2.8 |
| | 100596_at | selenium binding protein 1 | Selenbp1 | M32032 | −2.6 |
| | 99178_at | glycoprotein m6b | Gpm6b | AI845652 | −2.6 |
| | 93574_at | serine (or cysteine) proteinase inhibitor, clade F (alpha-2 antiplasmin, pigment epithelium derived factor), member 1 | Serpinf1 | AF036164 | −2.5 |
| | 160948_at | protein phosphatase 3, catalytic subunit, gamma isoform | Ppp3cc | M81475 | −2.0 |
| | 100606_at | Prion Protein | Prnp | M18070 | −2.0 |
| | 92480_f_at | Zinc finger protein 118 | Zfp118 | AB024004 | −2.0 |
| | 102779_at | growth arrest and DNA-damage-inducible 45 beta | Gadd45b | X54149 | −2.0 |
| | 103025_at | Moloney leukemia virus 10 | Mov10 | X52574 | 2.0 |
| | 98600_at | S100 calcium binding protein A11 | S100a11 | U41341 | 2.0 |
| | 97507_at | peptidylprolyl isomerase C-associated protein | Ppicap | X67809 | 2.1 |
| | 98030_at | tripartite motif protein 30 | Trim30 | J03776 | 2.3 |
| | 92644_s_at | myb proto-oncogene | Myb | M12848 | 2.5 |
| | 92214_at | cathepsin W | Ctsw | AF014941 | 2.6 |
| | 96060_at | serine (or cysteine) proteinase inhibitor, clade B (ovalbumin), member 6 | Serpinb6 | U25844 | 2.8 |
| | 103554_at | a disintegrin and metalloproteinase domain 19 (meltrin beta) | Adam19 | AA726223 | 4.0 |

REFERENCES

1. Umetsu, D. T., and R. H. DeKruyff. 1997. Th1 and Th2 CD4+ cells in the pathogenesis of allergic diseases. *Proc Soc Exp Biol Med* 215, no. 1:11.
2. Romagnani, S. 1996. Th1 and Th2 in human diseases. *Clin Immunol Immunopathol* 80, no. 3 Pt 1:225.
3. Nicholson, L. B., and V. K. Kuchroo. 1996. Manipulation of the Th1/Th2 balance in autoimmune disease. *Curr Opin Immunol* 8, no. 6:837.
4. Mosmann, T. R., H. Cherwinski, M. W. Bond, M. A. Giedlin, and R. L. Coffman. 1986. Two types of murine helper T cell clone. I. Definition according to profiles of lymphokine activities and secreted proteins. *J Immunol* 136, no. 7:2348.
5. Murphy, K. M., W. Ouyang, J. D. Farrar, J. Yang, S. Ranganath, H. Asnagli, M. Afkarian, and T. L. Murphy. 2000. Signaling and transcription in T helper development. *Annu Rev Immunol* 18:451.
6. Bacon, C. M., E. F. Petricoin, 3rd, J. R. Ortaldo, R. C. Rees, A. C. Larner, J. A. Johnston, and J. J. O'Shea. 1995. Interleukin 12 induces tyrosine phosphorylation and activation of STAT4 in human lymphocytes. *Proc Natl Acad Sci USA* 92, no. 16:7307.
7. Jacobson, N. G., S. J. Szabo, R. M. Weber-Nordt, Z. Zhong, R. D. Schreiber, J. E. Darnell, Jr., and K. M. Murphy. 1995. Interleukin 12 signaling in T helper type 1 (Th1) cells involves tyrosine phosphorylation of signal transducer and activator of transcription (Stat)3 and Stat4. *J Exp Med* 181, no. 5:1755.
8. Kaplan, M. H., Y. L. Sun, T. Hoey, and M. J. Grusby. 1996. Impaired IL-12 responses and enhanced development of Th2 cells in Stat4- deficient mice. *Nature* 382, no. 6587:174.
9. Hou, J., U. Schindler, W. J. Henzel, T. C. Ho, M. Brasseur, and S. L. McKnight. 1994. An interleukin-4-induced transcription factor: IL-4 Stat. *Science* 265, no. 5179:1701.
10. Kaplan, M. H., U. Schindler, S. T. Smiley, and M. J. Grusby. 1996. Stat6 is required for mediating responses to IL-4 and for development of Th2 cells. *Immunity* 4, no. 3:313.
11. Afkarian, M., J. R. Sedy, J. Yang, N. G. Jacobson, N. Cereb, S. Y. Yang, T. L. Murphy, and K. M. Murphy. 2002. T-bet is a STAT1-induced regulator of IL-12R expression in naive CD4+ T cells. *Nat Immunol* 3, no. 6:549.
12. Lighvani, A. A., D. M. Frucht, D. Jankovic, H. Yamane, J. Aliberti, B. D. Hissong, B. V. Nguyen, M. Gadina, A. Sher, W. E. Paul, and J. J. O'Shea. 2001. T-bet is rapidly induced by interferon-gamma in lymphoid and myeloid cells. *Proc Natl Acad Sci USA* 98, no. 26:15137.

13. Szabo, S. J., S. T. Kim, G. L. Costa, X. Zhang, C. G. Fathman, and L. H. Glimcher. 2000. A novel transcription factor, T-bet, directs Th1 lineage commitment. *Cell* 100, no. 6:655.

14. Zhang, D. H., L. Cohn, P. Ray, K. Bottomly, and A. Ray. 1997. Transcription factor GATA-3 is differentially expressed in murine Th1 and Th2 cells and controls Th2-specific expression of the interleukin-5 gene. *J Biol Chem* 272, no. 34:21597.

15. Zheng, W., and R. A. Flavell. 1997. The transcription factor GATA-3 is necessary and to sufficient for Th2 cytokine gene expression in CD4 T cells. *Cell* 89, no. 4:587.

16. Ho, I. C., M. R. Hodge, J. W. Rooney, and L. H. Glimcher. 1996. The proto-oncogene c-maf is responsible for tissue-specific expression of interleukin-4. *Cell* 85, no. 7:973.

17. Gorelik, L., and R. A. Flavell. 2002. Transforming growth factor-beta in T-cell biology. *Nature Rev Immunol* 2, no. 1:46.

18. Hamalainen, H., S. Meissner, and R. Lahesmaa. 2000. Signaling lymphocytic activation molecule (SLAM) is differentially expressed in human Th1 and Th2 cells. *J Immunol Methods* 242, no. 1-2:9.

19. Hamalainen, H. K., J. C. Tubman, S. Vikman, T. Kyrola, E. Ylikoski, J. A. Warrington, and R. Lahesmaa. 2001. Validation of endogenous reference genes for profiling of lymphocyte differentiation by quantitative real-time RT-PCR. *Anal Biochem* 299, no. 1:63.

20. Yang, L. P., D. G. Byun, C. E. Demeure, N. Vezzio, and G. Delespesse. 1995. Default development of cloned human naive CD4 T cells into interleukin- 4- and interleukin-5-producing effector cells. *Eur J Immunol* 25, no. 12:3517.

21. Rogge, L., E. Bianchi, M. Biffi, E. Bono, S. Y. Chang, H. Alexander, C. Santini, G. Ferrari, L. Sinigaglia, M. Seiler, M. Neeb, J. Mous, F. Sinigaglia, and U. Certa. 2000. Transcript imaging of the development of human T helper cells using oligonucleotide arrays [In Process Citation]. *Nat Genet* 25, no. 1:96.

22. Chtanova, T., R. A. Kemp, A. P. Sutherland, F. Ronchese, and C. R. Mackay. 2001. Gene microarrays reveal extensive differential gene expression in both cd4(+) and cd8(+) type 1 and type 2 t cells. *J Immunol* 167, no. 6:3057.

23. Sareneva, T., I. Julkunen, and S. Matikainen. 2000. IFN-alfa and IL-12 induce IL-18 receptor gene expression in human NK and T cells. *The Journal of Immunology* 165: 1933.

24. Bonecchi, R., G. Bianchi, P. P. Bordignon, D. D'Ambrosio, R. Lang, A. Borsatti, S. Sozzani, P. Allavena, P. A. Gray, A. Mantovani, and F. Sinigaglia. 1998. Differential expression of chemokine receptors and chemotactic responsiveness of type 1 T helper cells (Th1s) and Th2s. *J Exp Med* 187, no. 1:129.

25. Tanaka, H., C. E. Demeure, M. Rubio, G. Delespesse, and M. Sarfati. 2000. Human monocyte-derived dendritic cells induce naive T cell differentiation into T helper cell type 2 (Th2) or Th1/Th2 effectors. Role of stimulator/responder ratio. *J Exp Med* 192, no. 3:405.

26. Ehrhard, P. B., P. Erb, U. Graumann, and U. Otten. 1993. Expression of nerve growth factor and nerve growth factor receptor tyrosine kinase Trk in activated CD4-positive T-cell clones. *Proc Natl Acad Sci USA* 90, no. 23:10984.

27. Lu, B., H. Yu, C. Chow, B. Li, W. Zheng, R. J. Davis, and R. A. Flavell. 2001. GADD45gamma mediates the activation of the p38 and JNK MAP kinase pathways and cytokine production in effector TH1 cells. *Immunity* 14, no. 5:583.

28. Yang, J., H. Zhu, T. L. Murphy, W. Ouyang, and K. M. Murphy. 2001. IL-18-stimulated GADD45 beta required in cytokine-induced, but not TCR-induced, IFN-gamma production. *Nat Immunol* 2, no. 2:157.

29. Schroder A J, Pavlidis P, Arimura A, Capece D, Rothman P B. Cutting edge: STAT6 serves as a positive and negative regulator of gene expression in IL-4-stimulated B lymphocytes. J Immunol. 2002 Feb. 1;168(3):996-1000.

30. Ohmori Y, Hamilton T A. IL-4-induced STAT6 suppresses IFN-gamma-stimulated STAT1-dependent transcription in mouse macrophages. J Immunol. 1997 Dec. 1;159(11): 5474-82.

31. Goenka S, Youn J, Dzurek L M, Schindler U, Yu-Lee L Y, Boothby M. Paired Stat6 C-terminal transcription activation domains required both for inhibition of an IFN-responsive promoter and trans-activation. J Immunol. 1999 Nov. 1;163(9):4663-72.

32. Ohmori Y, Hamilton T A. Interleukin-4/STAT6 represses STAT1 and NF-kappa B-dependent transcription through distinct mechanisms. J Biol Chem. 2000 Dec. 1;275(48): 38095-103.

33. Nelms K, Keegan A D, Zamorano J, Ryan J J, Paul W E. The IL-4 receptor: signaling mechanisms and biologic functions. Annu Rev Immunol. 1999;17:701-38.

34. Teague, T. K., D. Hildeman, R. M. Kedl, T. Mitchell, W. Rees, B. C. Schaefer, J. Bender, J. Kappler, and P. Marrack. 1999. Activation changes the spectrum but not the diversity of genes expressed by T cells. *Proc Natl Acad Sci USA* 96, no. 22:12691.

35. Zhao, Y., and Z. Y. Zhang. 2001. The mechanism of dephosphorylation of extracellular signal-regulated kinase 2 by mitogen-activated protein kinase phosphatase 3. *J Biol Chem* 276, no. 34:32382.

36. Ikushima, S., T. Inukai, T. Inaba, S. D. Nimer, J. L. Cleveland, and A. T. Look. 1997. Pivotal role for the NFIL3/E4BP4 transcription factor in interleukin 3-mediated survival of pro-B lymphocytes. *Proc Natl Acad Sci USA* 94, no. 6:2609.

37. Kuribara, R., T. Kinoshita, A. Miyajima, T. Shinjyo, T. Yoshihara, T. Inukai, K. Ozawa, A. T. Look, and T. Inaba. 1999. Two distinct interleukin-3-mediated signal pathways, Ras-NFIL3 (E4BP4) and Bcl-xL, regulate the survival of murine pro-B lymphocytes. *Mol Cell Biol* 19, no. 4:2754.

38. Alvarez, J. D., D. H. Yasui, H. Niida, T. Joh, D. Y. Loh, and T. Kohwi-Shigematsu. 2000. The MAR-binding protein SATB1 orchestrates temporal and spatial expression of multiple genes during T-cell development. *Genes Dev* 14, no. 5:521.

39. Galande, S., L. A. Dickinson, I. S. Mian, M. Sikorska, and T. Kohwi-Shigematsu. 2001. SATB1 cleavage by caspase 6 disrupts PDZ domain-mediated dimerization, causing detachment from chromatin early in T-cell apoptosis. *Mol Cell Biol* 21, no. 16:5591.

40. Diehl, S., J. Anguita, A. Hoffmeyer, T. Zapton, J. N. Ihle, E. Fikrig, and M. Rincon. 2000. Inhibition of Th1 differentiation by IL-6 is mediated by SOCS 1. *Immunity* 13, no. 6:805.

41. Egwuagu, C. E., C. R. Yu, M. Zhang, R. M. Mahdi, S. J. Kim, and I. Gery. 2002. Suppressors of cytokine signaling proteins are differentially expressed in Th1 and Th2 cells: implications for Th cell lineage commitment and maintenance. *J Immunol* 168, no. 7:3181.

42. Swain, S. L., G. Huston, S. Tonkonogy, and A. Weinberg. 1991. Transforming growth factor-beta and IL-4 cause helper T cell precursors to develop into distinct effector helper cells that differ in lymphokine secretion pattern and cell surface phenotype. *J Immunol* 147, no. 9:2991.

43. Sad, S., and T. R. Mosmann. 1994. Single IL-2-secreting precursor CD4 T cell can develop into either Th1 or Th2 cytokine secretion phenotype. *J Immunol* 153, no. 8:3514.

44. Gorelik, L., P. E. Fields, and R. A. Flavell. 2000. Cutting edge: TGF-beta inhibits Th type 2 development through inhibition of GATA-3 expression [In Process Citation]. *J Immunol* 165, no. 9:4773.

45. Heath, V. L., E. E. Murphy, C. Crain, M. G. Tomlinson, and A. O'Garra. 2000. TGF-beta1 down-regulates Th2 development and results in decreased IL4-induced STAT6 activation and GATA-3 expression. *Eur J Immunol* 30, no. 9:2639.

46. Gorelik, L., S. Constant, and R. A. Flavell. 2002. Mechanism of transforming growth factor beta-induced inhibition of T helper type 1 differentiation. *J Exp Med* 195, no. 11:1499.

47. Cerwenka, A., and S. L. Swain. 1999. TGF-beta1: immunosuppressant and viability factor for T lymphocytes. *Microbes Infect* 1, no. 15:1291.

48. Hansen, G., J. J. McIntire, V. P. Yeung, G. Berry, G. J. Thorbecke, L. Chen, R. H. DeKruyff, and D. T. Umetsu. 2000. CD4(+) T helper cells engineered to produce latent TGF-beta1 reverse allergen-induced airway hyperreactivity and inflammation. *J Clin Invest* 105, no. 1:61.

49. Nakao, A., S. Miike, M. Hatano, K. Okumura, T. Tokuhisa, C. Ra, and I. Iwamoto. 2000. Blockade of transforming growth factor beta/Smad signaling in T cells by overexpression of Smad7 enhances antigen-induced airway inflammation and airway reactivity. *J Exp Med* 192, no. 2:151.

50. Guan, K. L., and E. Butch. 1995. Isolation and characterization of a novel dual specific phosphatase, HVH2, which selectively dephosphorylates the mitogen-activated protein kinase. *J Biol Chem* 270, no. 13:7197.

51. Hirsch, D. D., and P. J. Stork. 1997. Mitogen-activated protein kinase phosphatases inactivate stress-activated protein kinase pathways in vivo. *J Biol Chem* 272, no. 7:4568.

52. Yang, D. D., D. Conze, A. J. Whitmarsh, T. Barrett, R. J. Davis, M. Rincon, and R. A. Flavell. 1998. Differentiation of CD4+ T cells to Th1 cells requires MAP kinase JNK2. *Immunity* 9, no. 4:575.

53. Dong, C., D. D. Yang, M. Wysk, A. J. Whitmarsh, R. J. Davis, and R.A. Flavell. 1998. Defective T cell differentiation in the absence of Jnk1. *Science* 282, no. 5396:2092.

54. Mao, X. Q., M. Kawai, T. Yamashita, T. Enomoto, Y. Dake, S. Sasaki, Y. Kataoka, T. Fukuzumi, K. Endo, H. Sano, T. Aoki, F. Kurimoto, C. N. Adra, T. Shirakawa, and J. M. Hopkin. 2000. Imbalance production between interleukin-1beta (IL-1beta) and IL-1 receptor antagonist (IL-1Ra) in bronchial asthma. *Biochem Biophys Res Commun* 276, no. 2:607.

55. Blakemore, A. I., A. Cox, A. M. Gonzalez, J. K. Maskil, M. E. Hughes, R. M. Wilson, J. D. Ward, and G. W. Duff. 1996. Interleukin-1 receptor antagonist allele (IL1RN*2) associated with nephropathy in diabetes mellitus. *Hum Genet* 97, no. 3:369.

56. Nicolaides, N. C., K. J. Holroyd, S. L. Ewart, S. M. Eleff, M. B. Kiser, C. R. Dragwa, C. D. Sullivan, L. Grasso, L. Y. Zhang, C. J. Messler, T. Zhou, S. R. Kleeberger, K. H. Buetow, and R. C. Levitt. 1997. Interleukin 9: a candidate gene for asthma. *Proc Natl Acad Sci USA* 94, no. 24:13175.

57. Zhou, Y., M. McLane, and R. C. Levitt. 2001. Th2 cytokines and asthma. Interleukin-9 as a therapeutic target for asthma. *Respir Res* 2, no. 2:80.

58. Del Pozo, V., M. Rojo, M. L. Rubio, I. Cortegano, B. Cardaba, S. Gallardo, M. Ortega, E. Civantos, E. Lopez, C. Martin-Mosquero, G. Peces-Barba, P. Palomino, N. Gonzalez-Mangado, and C. Lahoz. 2002. Gene Therapy with Galectin-3 Inhibits Bronchial Obstruction and Inflammation in Antigen-challenged Rats through Interleukin-5 Gene Downregulation. *Am J Respir Crit Care Med* 166, no. 5:732.

59. Cortegano, I., V. del Pozo, B. Cardaba, B. de Andres, S. Gallardo, A. del Amo, I. Arrieta, A. Jurado, P. Palomino, F. T. Liu, and C. Lahoz. 1998. Galectin-3 down-regulates IL-5 gene expression on different cell types. *J Immunol* 161, no. 1:385.

The invention claimed is:

1. A method of identifying a compound capable of modulating the polarization of CD4+ lymphocytes, the method comprising:
   (a) contacting said compound with naïve CD4+ lymphocytes;
   (b) inducing Th1 or Th2 polarization of the lymphocytes by contacting said lymphocytes with IL-4;
   (c) preparing a gene expression profile from the lymphocytes; and
   (d) comparing the lymphocyte gene expression profile obtained from step (c) to a gene expression profile, obtained from similarly polarized CD4+ lymphocytes not contacted with the compound
   wherein said gene expression profiles of steps (c) and (d) comprise the expression of STK17B
   and wherein a (difference between the expression profiles of step (c) and (d) identifies a compound capable of modulating the polarization of CD4+ lymphocytes.

2. The method according to claim 1, wherein the gene expression profile also comprises one or more genes selected from the group consisting of: SATB1, KIAA0053, MAL or UBL3.

3. The method according to claim 1, wherein the gene expression profile comprises the expression of one or more genes selected from the group consisting of: cig5 IL10RA, MAP3K14, ADPRTL2, NFIL3, DUSP6, a gene having accession number AI432401, EDG1, KIAA0053, RASA2, SSI-1, LRRN3, RIPK2, a gene having accession number AI971169, GNAI1, MAL, PTGER2, LOC64116, RASGRP1, PSPH, CD47, SOS1, SLC11A2, SATB1, a gene having accession numbers HG1751-HT1768, GATA3, TP53BP2, KIAA0914, MAF, CXCR4, RTP801, NINJ1, a gene having accession number AL049449, ID3, SPINT2, ACTN1, NKG7, CNTN5, S100P, ABCD3, EBI2, UBL3, H2BFQ, ANXA1, CD8B1, FLT3LG, PPP1R16B, ZYX, SCYC1, a gene having accession numbers HG2639-HT2735, IL1RN, SIAT9, SPP1, SCYA20, LPL, SCYA2, OPTN, TCF7, POU2AF1, TNFRSF7, a gene having accession number AL049233, DSG1, GZMB, Trk, AIM2, Cox-2, PLA2G4A, GATA3, NTRK1, MAOA, FER1L3, B-ATF, KIAA1013, ID2, SERPINB1, KIAA0750, HMGCS1, ZFP36, RYBP, AUH, BCL2A1, a gene having accession number AF054589, CD83, GBP1, STAT1, PDE4B, ISGF3, MALT1, ISGF3, NR4A2, LTB, MX1, G0S2, and/or NR4A2.

4. The method according to claim 1 wherein the gene expression profile also comprises the expression of one or more genes selected from the group consisting of: DSC3, GATA2, MRPL33, HTR6, IFNG, a gene having the accession number x13274, IFNG, a gene having the accession number J00219, IL18RAP, GZMB, CTLA1, PACE, G0S2, MRF-1, SERPINB1, BLR1, LAG3, FLOT1, IL12RB2, SLAM, MTMR1, GOSR2, NR4A2, a gene having accession number AF055029, GARP, a gene having accession number AL050166, SCYC2, LAIR2, and/or TNFRSF9.

5. The method according to claim 3, wherein a difference in the expression profiles identifies a potential drug compound.

* * * * *